(12) United States Patent
Grassano et al.

(10) Patent No.: US 10,449,547 B2
(45) Date of Patent: Oct. 22, 2019

(54) PREPARATION OF A POWDERY PHARMACEUTICAL COMPOSITION BY MEANS OF CRYO-MILLING

(71) Applicant: GRÜNENTHAL GMBH, Aachen (DE)

(72) Inventors: Alessandro Grassano, Monza (IT);
Anna Perachiotti, Cornaredo (IT);
Matteo Minelli, Gualdo Tadino (IT);
Daniele Volpi, Caronno Pertusella (IT)

(73) Assignee: GRÜNENTHAL GMBH, Aachen (DE)

( * ) Notice: Subject to any disclaimer, the term of this patent is extended or adjusted under 35 U.S.C. 154(b) by 618 days.

(21) Appl. No.: 15/164,326

(22) Filed: May 25, 2016

(65) Prior Publication Data

US 2016/0263032 A1     Sep. 15, 2016

Related U.S. Application Data

(63) Continuation of application No. PCT/EP2014/075618, filed on Nov. 26, 2014.

(30) Foreign Application Priority Data

Nov. 26, 2013 (EP) .................................... 13425151

(51) Int. Cl.
*B02C 19/00* (2006.01)
*B02C 19/18* (2006.01)
(Continued)

(52) U.S. Cl.
CPC ............ *B02C 19/186* (2013.01); *A61K 9/145* (2013.01); *A61K 9/146* (2013.01); *A61K 45/06* (2013.01);
(Continued)

(58) Field of Classification Search
CPC ......... B02C 23/08; B02C 19/186; B02C 7/17; A61K 9/146
(Continued)

(56) References Cited

U.S. PATENT DOCUMENTS 2,524,855 A    10/1950   Schnider et al.
2,806,033 A     9/1957   Lewenstein et al.
(Continued)

FOREIGN PATENT DOCUMENTS

AR           046994 A1    12/2004
AR           045353 A1    10/2005
(Continued)

OTHER PUBLICATIONS 2.9 Methoden der pharmazeutischen Technologie, European Pharmacopeia, 143-144, 1997. (Full English translation attached).
(Continued)

*Primary Examiner* — Faye Francis
(74) *Attorney, Agent, or Firm* — Norris McLaughlin P.A.

(57) ABSTRACT

A method for the preparation of a powdery pharmaceutical composition composed of a pharmaceutical excipient and a pharmaceutical component, among other possible ingredients, wherein the pharmaceutical excipient is a polyalkylene glycol, the method involving grinding a mixture of the pharmaceutical excipient and the pharmaceutical component at a temperature below ambient temperature.

12 Claims, 8 Drawing Sheets

(51) Int. Cl.
  *A61K 9/14* (2006.01)
  *A61K 45/06* (2006.01)
  *B02C 7/17* (2006.01)
  *B02C 17/18* (2006.01)
  *B02C 23/08* (2006.01)
  *B29B 7/20* (2006.01)
  *B29B 9/10* (2006.01)
  *B29B 9/12* (2006.01)
  *B29B 9/16* (2006.01)
  *B29K 71/00* (2006.01)

(52) U.S. Cl.
  CPC ............ *B02C 7/17* (2013.01); *B02C 17/1815* (2013.01); *B02C 23/08* (2013.01); *B29B 7/20* (2013.01); *B29B 9/10* (2013.01); *B29B 9/12* (2013.01); *B29B 9/16* (2013.01); *B29B 2009/125* (2013.01); *B29K 2071/00* (2013.01)

(58) Field of Classification Search
  USPC ...................................... 241/DIG. 37, 23, 65
  See application file for complete search history.

(56) References Cited

U.S. PATENT DOCUMENTS

| | | |
|---|---|---|
| 2,987,445 A | 6/1961 | Levesque |
| 3,332,950 A | 7/1967 | Blumberg et al. |
| 3,370,035 A | 2/1968 | Ogura et al. |
| 3,652,589 A | 3/1972 | Flick et al. |
| 3,658,259 A * | 4/1972 | Ledergerber .......... B02C 19/186 241/23 |
| 3,806,603 A | 4/1974 | Gaunt et al. |
| 3,865,108 A | 2/1975 | Hartop |
| 3,941,865 A | 3/1976 | Miller et al. |
| 3,966,747 A | 6/1976 | Monkovic et al. |
| 3,980,766 A | 9/1976 | Shaw et al. |
| 4,002,173 A | 1/1977 | Manning et al. |
| 4,014,965 A | 3/1977 | Stube et al. |
| 4,070,494 A | 1/1978 | Hoffmeister et al. |
| 4,070,497 A | 1/1978 | Wismer et al. |
| 4,175,119 A | 11/1979 | Porter |
| 4,200,704 A | 4/1980 | Stanley et al. |
| 4,207,893 A | 6/1980 | Michaels |
| 4,262,017 A | 4/1981 | Kuipers et al. |
| 4,343,789 A | 8/1982 | Kawata et al. |
| 4,353,887 A | 10/1982 | Hess et al. |
| 4,404,183 A | 9/1983 | Kawata et al. |
| 4,427,681 A | 1/1984 | Munshi et al. |
| 4,427,778 A | 1/1984 | Zabriskie |
| 4,457,933 A | 7/1984 | Gordon et al. |
| 4,462,941 A | 7/1984 | Lee et al. |
| 4,473,640 A | 9/1984 | Combie et al. |
| 4,483,847 A | 11/1984 | Augart |
| 4,485,211 A | 11/1984 | Okamoto |
| 4,529,583 A | 7/1985 | Porter |
| 4,599,342 A | 7/1986 | La Hann |
| 4,603,143 A | 7/1986 | Schmidt |
| 4,612,008 A | 9/1986 | Wong et al. |
| 4,629,621 A | 12/1986 | Snipes |
| 4,667,013 A | 5/1987 | Reichle |
| 4,690,822 A | 9/1987 | Uemura |
| 4,711,894 A | 12/1987 | Wenzel et al. |
| 4,713,243 A | 12/1987 | Schiraldi et al. |
| 4,744,976 A | 5/1988 | Snipes et al. |
| 4,764,378 A | 8/1988 | Keitn et al. |
| 4,765,989 A | 8/1988 | Wong et al. |
| 4,774,074 A | 9/1988 | Snipes |
| 4,774,092 A | 9/1988 | Hamilton |
| 4,783,337 A | 11/1988 | Wong et al. |
| 4,806,337 A | 2/1989 | Snipes et al. |
| RE33,093 E | 10/1989 | Schiraldi et al. |
| 4,880,585 A | 11/1989 | Klimesch et al. |
| 4,892,778 A | 1/1990 | Theeuwes et al. |
| 4,892,889 A | 1/1990 | Kirk |
| 4,940,556 A | 7/1990 | MacFarlane et al. |
| 4,954,346 A | 9/1990 | Sparta et al. |
| 4,957,668 A | 9/1990 | Plackard et al. |
| 4,957,681 A | 9/1990 | Klimesch et al. |
| 4,960,814 A | 10/1990 | Wu et al. |
| 4,992,278 A | 2/1991 | Khanna |
| 4,992,279 A | 2/1991 | Palmer et al. |
| 5,004,601 A | 4/1991 | Snipes |
| 5,051,261 A | 9/1991 | McGinty |
| 5,073,379 A | 12/1991 | Klimesch et al. |
| 5,082,668 A | 1/1992 | Wong et al. |
| 5,126,151 A | 6/1992 | Bodor et al. |
| 5,139,790 A | 8/1992 | Snipes |
| 5,145,944 A | 9/1992 | Steinmann |
| 5,149,538 A | 9/1992 | Granger et al. |
| 5,169,645 A | 12/1992 | Shukla et al. |
| 5,190,760 A | 3/1993 | Baker |
| 5,198,226 A | 3/1993 | MacFarlane et al. |
| 5,200,194 A | 4/1993 | Edgren et al. |
| 5,200,197 A | 4/1993 | Wright et al. |
| 5,211,892 A | 5/1993 | Gueret |
| 5,225,417 A | 7/1993 | Dappen |
| 5,227,157 A | 7/1993 | McGinity et al. |
| 5,229,164 A | 7/1993 | Pins et al. |
| 5,273,758 A | 12/1993 | Royce |
| 5,326,852 A | 7/1994 | Fujikake |
| 5,350,741 A | 9/1994 | Takada |
| 5,378,462 A | 1/1995 | Boedecker et al. |
| 5,387,420 A | 2/1995 | Mitchell |
| 5,427,798 A | 6/1995 | Ludwig et al. |
| RE34,990 E | 7/1995 | Khanna et al. |
| 5,458,887 A | 10/1995 | Chen et al. |
| 5,460,826 A | 10/1995 | Merrill et al. |
| 5,472,943 A | 12/1995 | Crain et al. |
| 5,508,042 A | 4/1996 | Oshlack et al. |
| 5,552,159 A | 9/1996 | Mueller et al. |
| 5,556,640 A | 9/1996 | Ito et al. |
| 5,562,920 A | 10/1996 | Demmer et al. |
| 5,591,452 A | 1/1997 | Miller et al. |
| 5,593,694 A | 1/1997 | Hayashida et al. |
| 5,601,842 A | 2/1997 | Bartholomaeus |
| 5,620,697 A | 4/1997 | Tormala et al. |
| 5,679,685 A | 10/1997 | Cincotta et al. |
| 5,681,517 A | 10/1997 | Metzger |
| 5,707,636 A | 1/1998 | Rodriguez et al. |
| 5,741,519 A | 4/1998 | Rosenberg et al. |
| 5,792,474 A | 8/1998 | Rauchfuss |
| 5,801,201 A | 9/1998 | Gradums et al. |
| 5,811,126 A | 9/1998 | Krishanamurthy |
| 5,849,240 A | 12/1998 | Miller et al. |
| 5,866,164 A | 2/1999 | Kuczynski et al. |
| 5,900,425 A | 5/1999 | Kanikanti et al. |
| 5,908,850 A | 6/1999 | Zeitlin et al. |
| 5,914,132 A | 6/1999 | Kelm et al. |
| 5,916,584 A | 6/1999 | O'Donoghue et al. |
| 5,928,739 A | 7/1999 | Pophusen et al. |
| 5,939,099 A | 8/1999 | Grabowski et al. |
| 5,945,125 A | 8/1999 | Kim |
| 5,948,787 A | 9/1999 | Merill et al. |
| 5,962,488 A | 10/1999 | Lang |
| 5,965,161 A | 10/1999 | Oshlack et al. |
| 5,968,925 A | 10/1999 | Knidlberger |
| 6,001,391 A | 12/1999 | Zeidler et al. |
| 6,009,390 A | 12/1999 | Gupta et al. |
| 6,009,690 A | 1/2000 | Rosenberg et al. |
| 6,051,253 A | 4/2000 | Zettler et al. |
| 6,071,970 A | 6/2000 | Mueller et al. |
| 6,077,538 A | 6/2000 | Merrill et al. |
| 6,090,411 A | 7/2000 | Pillay et al. |
| 6,093,420 A | 7/2000 | Baichwal |
| 6,096,339 A | 8/2000 | Ayer et al. |
| 6,117,453 A | 9/2000 | Seth et al. |
| 6,120,802 A | 9/2000 | Breitenbach et al. |
| 6,133,241 A | 10/2000 | Bok et al. |
| 6,183,781 B1 | 2/2001 | Burke |
| 6,235,825 B1 | 2/2001 | Yoshida et al. |
| 6,228,863 B1 | 5/2001 | Palermo et al. |
| 6,238,697 B1 | 5/2001 | Kumar et al. |
| 6,245,357 B1 | 6/2001 | Edgren et al. |

(56) References Cited

U.S. PATENT DOCUMENTS

| | | |
|---|---|---|
| 6,248,737 B1 | 6/2001 | Buschmann et al. |
| 6,251,430 B1 | 6/2001 | Zhang et al. |
| 6,254,887 B1 | 7/2001 | Miller et al. |
| 6,261,599 B1 | 7/2001 | Oshlack |
| 6,290,990 B1 | 9/2001 | Grabowski et al. |
| 6,306,438 B1 | 10/2001 | Oshlack et al. |
| 6,309,668 B1 | 10/2001 | Bastin et al. |
| 6,318,650 B1 | 11/2001 | Breitenbach et al. |
| 6,322,811 B1 | 11/2001 | Verma et al. |
| 6,322,819 B1 | 11/2001 | Burnside et al. |
| 6,326,027 B1 | 12/2001 | Miller et al. |
| 6,335,035 B1 | 1/2002 | Drizen et al. |
| 6,337,319 B1 | 1/2002 | Wang |
| 6,340,475 B2 | 1/2002 | Shell et al. |
| 6,344,215 B1 | 2/2002 | Bettman et al. |
| 6,344,535 B1 | 2/2002 | Timmermann et al. |
| 6,348,469 B1 | 2/2002 | Seth |
| 6,355,656 B1 | 3/2002 | Zeitlin et al. |
| 6,375,957 B1 | 4/2002 | Kaiko et al. |
| 6,375,963 B1 | 4/2002 | Repka et al. |
| 6,384,020 B1 | 5/2002 | Flanner et al. |
| 6,387,995 B1 | 5/2002 | Sojka |
| 6,399,100 B1 | 6/2002 | Clancy et al. |
| 6,419,954 B1 | 7/2002 | Chu et al. |
| 6,436,441 B1 | 8/2002 | Sako et al. |
| 6,455,052 B1 | 9/2002 | Marcussen et al. |
| 6,461,644 B1 | 10/2002 | Jackson et al. |
| 6,488,939 B1 | 12/2002 | Zeidler et al. |
| 6,488,962 B1 | 12/2002 | Berner et al. |
| 6,488,963 B1 | 12/2002 | McGinity et al. |
| 6,534,089 B1 | 3/2003 | Ayer et al. |
| 6,547,977 B1 | 4/2003 | Yan et al. |
| 6,547,997 B1 | 4/2003 | Breithenbach et al. |
| 6,562,375 B1 | 5/2003 | Sako et al. |
| 6,569,506 B1 | 5/2003 | Jerdee et al. |
| 6,572,889 B1 | 6/2003 | Guo |
| 6,592,901 B2 | 7/2003 | Durig et al. |
| 6,623,754 B2 | 9/2003 | Guo et al. |
| 6,635,280 B2 | 10/2003 | Shell et al. |
| 6,696,088 B2 | 2/2004 | Oshlack et al. |
| 6,699,503 B1 | 3/2004 | Sako et al. |
| 6,723,340 B2 | 4/2004 | Gusler et al. |
| 6,723,343 B2 | 4/2004 | Kugelmann |
| 6,733,783 B2 | 5/2004 | Oshlack et al. |
| 6,753,009 B2 | 6/2004 | Luber et al. |
| 6,821,588 B1 | 11/2004 | Hammer et al. |
| 6,979,722 B2 | 12/2005 | Hamamoto et al. |
| 7,074,430 B2 | 7/2006 | Miller et al. |
| 7,129,248 B2 | 10/2006 | Chapman et al. |
| 7,141,250 B2 | 11/2006 | Oshlack et al. |
| 7,157,103 B2 | 1/2007 | Sackler |
| 7,176,251 B1 | 2/2007 | Bastioli et al. |
| RE39,593 E | 4/2007 | Buschmann et al. |
| 7,201,920 B2 | 4/2007 | Kumar et al. |
| 7,214,385 B2 | 5/2007 | Gruber |
| 7,230,005 B2 | 6/2007 | Shafer et al. |
| 7,300,668 B2 | 11/2007 | Pryce et al. |
| 7,332,182 B2 | 2/2008 | Sackler |
| 7,388,068 B2 | 6/2008 | Falk et al. |
| 7,399,488 B2 | 7/2008 | Hirsh et al. |
| 7,510,726 B2 | 3/2009 | Kumar et al. |
| 7,674,799 B2 | 3/2010 | Chapman et al. |
| 7,674,800 B2 | 3/2010 | Chapman et al. |
| 7,683,072 B2 | 3/2010 | Chapman et al. |
| 7,776,314 B2 | 8/2010 | Bartholomaus et al. |
| 7,842,307 B2 | 11/2010 | Oshlack et al. |
| 7,851,482 B2 | 12/2010 | Dung et al. |
| 7,932,258 B2 | 4/2011 | Petereit et al. |
| 7,939,543 B2 | 5/2011 | Kupper |
| 7,968,119 B2 | 6/2011 | Farrell |
| 7,994,364 B2 | 8/2011 | Fischer et al. |
| 8,075,872 B2 | 12/2011 | Arkenau-Maric et al. |
| 8,101,630 B2 | 1/2012 | Kumar et al. |
| 8,114,383 B2 | 2/2012 | Bartholomaeus et al. |
| 8,114,384 B2 | 2/2012 | Arkenau et al. |
| 8,114,838 B2 | 2/2012 | Marchionni |
| 8,192,722 B2 | 6/2012 | Arkenau-Maric et al. |
| 8,202,542 B1 | 6/2012 | Mehta et al. |
| 8,309,060 B2 | 11/2012 | Bartholomaeus et al. |
| 8,309,122 B2 | 11/2012 | Kao et al. |
| 8,323,889 B2 | 12/2012 | Arkenau-Maric et al. |
| 8,329,216 B2 | 12/2012 | Kao et al. |
| 8,337,888 B2 | 12/2012 | Wright et al. |
| 8,383,152 B2 | 2/2013 | Jans et al. |
| 8,420,056 B2 | 4/2013 | Arkenau-Maric et al. |
| 8,445,023 B2 | 5/2013 | Guimberteau et al. |
| 8,722,086 B2 | 5/2014 | Arkenau-Maric et al. |
| 8,858,963 B1 | 10/2014 | Devarakonda et al. |
| 8,901,113 B2 | 12/2014 | Leech et al. |
| 9,044,758 B2 | 6/2015 | Niwa et al. |
| 9,192,578 B2 | 11/2015 | McGinity et al. |
| 9,463,165 B2 | 10/2016 | Shimatani et al. |
| 9,629,807 B2 | 4/2017 | Arkenau-Maric et al. |
| 9,737,490 B2 | 8/2017 | Barnscheid et al. |
| 9,750,701 B2 | 9/2017 | Jans et al. |
| 9,855,263 B2 | 1/2018 | Wening et al. |
| 9,884,022 B2 | 2/2018 | Deshmukh et al. |
| 9,925,146 B2 | 3/2018 | Barnscheid et al. |
| 2001/0038852 A1 | 11/2001 | Kolter et al. |
| 2002/0012701 A1 | 1/2002 | Kolter et al. |
| 2002/0015730 A1 | 2/2002 | Hoffmann et al. |
| 2002/0187192 A1 | 2/2002 | Joshi et al. |
| 2002/0051820 A1 | 5/2002 | Shell et al. |
| 2002/0114838 A1 | 8/2002 | Ayer et al. |
| 2002/0132359 A1 | 9/2002 | Waterman |
| 2002/0132395 A1 | 9/2002 | Iyer et al. |
| 2002/0176888 A1 | 11/2002 | Bartholomaeus et al. |
| 2002/0192277 A1 | 12/2002 | Oshlack et al. |
| 2003/0008409 A1 | 1/2003 | Spearman et al. |
| 2003/0015814 A1 | 1/2003 | Krull et al. |
| 2003/0017532 A1 | 1/2003 | Biswas et al. |
| 2003/0021546 A1 | 1/2003 | Sato |
| 2003/0044458 A1 | 3/2003 | Wright et al. |
| 2003/0044464 A1 | 3/2003 | Ziegler et al. |
| 2003/0059397 A1 | 3/2003 | Hughes |
| 2003/0064099 A1 | 4/2003 | Oshlack et al. |
| 2003/0068276 A1 | 4/2003 | Hughes et al. |
| 2003/0068370 A1 | 4/2003 | Sackler et al. |
| 2003/0068371 A1 | 4/2003 | Oshlack et al. |
| 2003/0068375 A1 | 4/2003 | Wright et al. |
| 2003/0068392 A1 | 4/2003 | Sackler |
| 2003/0069263 A1 | 4/2003 | Breder et al. |
| 2003/0077297 A1 | 4/2003 | Chen et al. |
| 2003/0077327 A1 | 4/2003 | Durig et al. |
| 2003/0091630 A1 | 5/2003 | Louie-Helm et al. |
| 2003/0092724 A1 | 5/2003 | Huaihung et al. |
| 2003/0104052 A1 | 6/2003 | Berner et al. |
| 2003/0104053 A1 | 6/2003 | Gusler et al. |
| 2003/0118641 A1 | 6/2003 | Maloney et al. |
| 2003/0124185 A1 | 7/2003 | Oshlack et al. |
| 2003/0125347 A1 | 7/2003 | Anderson et al. |
| 2003/0129230 A1 | 7/2003 | Baichwal et al. |
| 2003/0133985 A1 | 7/2003 | Louie-Helm et al. |
| 2003/0143269 A1 | 7/2003 | Oshlack et al. |
| 2003/0152622 A1 | 8/2003 | Louie-Helm et al. |
| 2003/0158242 A1 | 8/2003 | Kugelmann |
| 2003/0158265 A1 | 8/2003 | Radhakrishnan et al. |
| 2003/0175326 A1 | 9/2003 | Thombre |
| 2003/0198677 A1 | 10/2003 | Pryce Lewis et al. |
| 2003/0215508 A1 | 11/2003 | Davis et al. |
| 2003/0224051 A1 | 12/2003 | Fink et al. |
| 2003/0232895 A1 | 12/2003 | Omidian et al. |
| 2004/0010000 A1 | 1/2004 | Ayer et al. |
| 2004/0011806 A1 | 1/2004 | Luciano et al. |
| 2004/0049079 A1 | 3/2004 | Murray et al. |
| 2004/0052731 A1 | 3/2004 | Hirsh et al. |
| 2004/0052844 A1 | 3/2004 | Hsiao et al. |
| 2004/0081694 A1 | 4/2004 | Oshlack et al. |
| 2004/0091528 A1 | 5/2004 | Rogers et al. |
| 2004/0126428 A1 | 7/2004 | Hughes et al. |
| 2004/0131671 A1 | 7/2004 | Zhang et al. |
| 2004/0156899 A1 | 8/2004 | Louie-Helm et al. |
| 2004/0170567 A1 | 9/2004 | Sackler |
| 2004/0170680 A1 | 9/2004 | Oshlack et al. |

(56) References Cited

U.S. PATENT DOCUMENTS

| | | |
|---|---|---|
| 2004/0185105 A1 | 9/2004 | Berner et al. |
| 2004/0213845 A1 | 10/2004 | Sugihara |
| 2004/0213848 A1 | 10/2004 | Li et al. |
| 2004/0253310 A1 | 12/2004 | Fischer et al. |
| 2005/0015730 A1 | 1/2005 | Gunturi et al. |
| 2005/0031546 A1 | 2/2005 | Bartholomaus et al. |
| 2005/0058706 A1 | 3/2005 | Bartholomaeus et al. |
| 2005/0063214 A1 | 3/2005 | Takashima |
| 2005/0079138 A1* | 4/2005 | Chickering, III ...... A61K 9/145 424/46 |
| 2005/0089475 A1 | 4/2005 | Gruber |
| 2005/0089569 A1 | 4/2005 | Bar-Shalom |
| 2005/0095291 A1 | 5/2005 | Oshlack et al. |
| 2005/0106249 A1 | 5/2005 | Hwang et al. |
| 2005/0112067 A1 | 5/2005 | Kumar et al. |
| 2005/0127555 A1 | 6/2005 | Gusik et al. |
| 2005/0152843 A1 | 7/2005 | Bartholomaus et al. |
| 2005/0181046 A1 | 8/2005 | Oshlack et al. |
| 2005/0186139 A1 | 8/2005 | Bartholomaus et al. |
| 2005/0191244 A1 | 9/2005 | Bartholomaus et al. |
| 2005/0191352 A1 | 9/2005 | Hayes |
| 2005/0192333 A1 | 9/2005 | Hinze et al. |
| 2005/0214223 A1 | 9/2005 | Bartholomaeus et al. |
| 2005/0220877 A1 | 10/2005 | Patel |
| 2005/0222188 A1 | 10/2005 | Chapman et al. |
| 2005/0236741 A1 | 10/2005 | Arkenau et al. |
| 2005/0245556 A1 | 11/2005 | Brogman et al. |
| 2005/0266084 A1 | 12/2005 | Li et al. |
| 2005/0271594 A1 | 12/2005 | Groenewoud |
| 2006/0002859 A1 | 1/2006 | Arkenau et al. |
| 2006/0002860 A1 | 1/2006 | Bartholomaus et al. |
| 2006/0004034 A1 | 1/2006 | Hinze et al. |
| 2006/0009478 A1 | 1/2006 | Friedman et al. |
| 2006/0017916 A1 | 1/2006 | Clarke et al. |
| 2006/0039864 A1 | 2/2006 | Bartholomaus et al. |
| 2006/0073102 A1 | 4/2006 | Huaihung et al. |
| 2006/0099250 A1 | 5/2006 | Tian et al. |
| 2006/0104909 A1 | 5/2006 | Vaghefi |
| 2006/0182801 A1 | 8/2006 | Breder et al. |
| 2006/0188447 A1 | 8/2006 | Arkenau-Maric et al. |
| 2006/0193782 A1 | 8/2006 | Bartholomaus et al. |
| 2006/0193914 A1 | 8/2006 | Ashworth et al. |
| 2006/0194759 A1 | 8/2006 | Eidelson |
| 2006/0194826 A1 | 8/2006 | Oshlack et al. |
| 2006/0204575 A1 | 9/2006 | Feng et al. |
| 2006/0240105 A1 | 10/2006 | Devane et al. |
| 2006/0240110 A1 | 10/2006 | Kiick et al. |
| 2006/0269603 A1 | 11/2006 | Brown Miller et al. |
| 2007/0003616 A1 | 1/2007 | Arkenau-Maric et al. |
| 2007/0003617 A1 | 1/2007 | Fischer et al. |
| 2007/0020188 A1 | 1/2007 | Sackler |
| 2007/0020335 A1 | 1/2007 | Chen et al. |
| 2007/0042044 A1 | 2/2007 | Fischer et al. |
| 2007/0048228 A1 | 3/2007 | Arkenau-Maric et al. |
| 2007/0048373 A1* | 3/2007 | Chastain ............ A61K 9/1623 424/464 |
| 2007/0065365 A1 | 3/2007 | Kugelmann et al. |
| 2007/0092573 A1 | 4/2007 | Joshi et al. |
| 2007/0183979 A1 | 8/2007 | Arkenau-Maric et al. |
| 2007/0183980 A1 | 8/2007 | Arkenau-Maric et al. |
| 2007/0184117 A1 | 8/2007 | Gregory et al. |
| 2007/0190142 A1 | 8/2007 | Breitenbach et al. |
| 2007/0196396 A1 | 8/2007 | Pilgaonkar et al. |
| 2007/0196481 A1 | 8/2007 | Amidon et al. |
| 2007/0224129 A1 | 9/2007 | Guimberteau et al. |
| 2007/0231268 A1 | 10/2007 | Emigh et al. |
| 2007/0259045 A1 | 11/2007 | Mannion et al. |
| 2007/0264326 A1 | 11/2007 | Guimberteau et al. |
| 2007/0264327 A1 | 11/2007 | Kumar et al. |
| 2007/0269505 A1 | 11/2007 | Flath et al. |
| 2007/0292508 A1 | 12/2007 | Szamosi et al. |
| 2008/0014228 A1 | 1/2008 | Darmuzey et al. |
| 2008/0020032 A1 | 1/2008 | Crowley et al. |
| 2008/0063725 A1 | 3/2008 | Guimberteau et al. |
| 2008/0069871 A1 | 3/2008 | Vaughn et al. |
| 2008/0075669 A1 | 3/2008 | Soscia et al. |
| 2008/0075768 A1 | 3/2008 | Vaughn et al. |
| 2008/0081290 A1 | 3/2008 | Wada et al. |
| 2008/0085304 A1 | 4/2008 | Baichwal et al. |
| 2008/0131503 A1 | 6/2008 | Holm et al. |
| 2008/0145429 A1 | 6/2008 | Leyenecker et al. |
| 2008/0152595 A1 | 6/2008 | Emigh et al. |
| 2008/0181932 A1 | 7/2008 | Bortz et al. |
| 2008/0207757 A1 | 8/2008 | Mickle |
| 2008/0220079 A1 | 9/2008 | Chen et al. |
| 2008/0233178 A1 | 9/2008 | Reidenberg et al. |
| 2008/0234352 A1 | 9/2008 | Fischer et al. |
| 2008/0247959 A1 | 10/2008 | Bartholomaus et al. |
| 2008/0248113 A1 | 10/2008 | Bartholomaus et al. |
| 2008/0260836 A1 | 10/2008 | Boyd |
| 2008/0280975 A1 | 11/2008 | Badul |
| 2008/0311049 A1 | 12/2008 | Arkenau-Maric et al. |
| 2008/0311187 A1 | 12/2008 | Ashworth et al. |
| 2008/0311197 A1 | 12/2008 | Arkenau-Maric et al. |
| 2008/0311205 A1 | 12/2008 | Habib et al. |
| 2008/0312264 A1 | 12/2008 | Arkenau-Maric et al. |
| 2008/0317695 A1 | 12/2008 | Everaert et al. |
| 2008/0317854 A1 | 12/2008 | Arkenau et al. |
| 2009/0004267 A1 | 1/2009 | Arkenau-Maric et al. |
| 2009/0005408 A1 | 1/2009 | Arkenau-Maric et al. |
| 2009/0011016 A1 | 1/2009 | Cailly-Dufestel et al. |
| 2009/0017121 A1 | 1/2009 | Berner et al. |
| 2009/0022798 A1 | 1/2009 | Rosenberg et al. |
| 2009/0081287 A1 | 3/2009 | Wright et al. |
| 2009/0081290 A1 | 3/2009 | McKenna et al. |
| 2009/0087486 A1 | 4/2009 | Krumme |
| 2009/0117191 A1 | 5/2009 | Brown Miller et al. |
| 2009/0143478 A1* | 6/2009 | Richardson ............ A01N 25/12 514/646 |
| 2009/0202634 A1 | 8/2009 | Jans et al. |
| 2009/0215808 A1 | 8/2009 | Yum et al. |
| 2009/0232887 A1 | 9/2009 | Odidi et al. |
| 2009/0253730 A1 | 10/2009 | Kumar et al. |
| 2009/0258066 A1 | 10/2009 | Venkatesh et al. |
| 2009/0317355 A1 | 12/2009 | Roth et al. |
| 2009/0318395 A1 | 12/2009 | Schramm et al. |
| 2010/0015223 A1 | 1/2010 | Cailly-Deufestel et al. |
| 2010/0035886 A1 | 2/2010 | Cincotta et al. |
| 2010/0047345 A1 | 2/2010 | Crowley et al. |
| 2010/0092553 A1 | 4/2010 | Guimberteau et al. |
| 2010/0098758 A1 | 4/2010 | Bartholomaus et al. |
| 2010/0099696 A1 | 4/2010 | Soscia et al. |
| 2010/0104638 A1 | 4/2010 | Dai et al. |
| 2010/0151028 A1 | 6/2010 | Ashworth et al. |
| 2010/0168148 A1 | 7/2010 | Wright et al. |
| 2010/0172989 A1 | 7/2010 | Roth et al. |
| 2010/0203129 A1 | 8/2010 | Anderson et al. |
| 2010/0221322 A1 | 9/2010 | Bartholomaus et al. |
| 2010/0239667 A1 | 9/2010 | Hemmingsen et al. |
| 2010/0249045 A1 | 9/2010 | Babul |
| 2010/0260833 A1 | 10/2010 | Bartholomaus et al. |
| 2010/0280047 A1 | 11/2010 | Kolter et al. |
| 2010/0291205 A1 | 11/2010 | Downie et al. |
| 2010/0297229 A1 | 11/2010 | Sesha |
| 2010/0316712 A1 | 12/2010 | Nangia et al. |
| 2011/0020451 A1 | 1/2011 | Bartholomaus et al. |
| 2011/0020454 A1 | 1/2011 | Lamarca Casado |
| 2011/0038930 A1 | 2/2011 | Barnscheid et al. |
| 2011/0077238 A1 | 3/2011 | Leech et al. |
| 2011/0082214 A1 | 4/2011 | Faure et al. |
| 2011/0092515 A1 | 4/2011 | Qiu et al. |
| 2011/0097404 A1 | 4/2011 | Oshlack et al. |
| 2011/0129535 A1 | 6/2011 | Mantelle |
| 2011/0159100 A1 | 6/2011 | Anderson et al. |
| 2011/0187017 A1 | 8/2011 | Haupts |
| 2011/0223244 A1 | 9/2011 | Liversidge et al. |
| 2011/0245783 A1 | 10/2011 | Stinchcomb |
| 2011/0262496 A1 | 10/2011 | Desai |
| 2012/0034171 A1 | 2/2012 | Arkenau-Maric et al. |
| 2012/0059065 A1 | 3/2012 | Barnscheid et al. |
| 2012/0065220 A1 | 3/2012 | Barnscheid et al. |
| 2012/0077879 A1 | 3/2012 | Vasanthavada et al. |
| 2012/0107250 A1 | 5/2012 | Bartholomaus et al. |
| 2012/0108622 A1 | 5/2012 | Wright et al. |

(56) References Cited

U.S. PATENT DOCUMENTS

| | | | |
|---|---|---|---|
| 2012/0135071 A1 | 5/2012 | Bartholomaus et al. |
| 2012/0136021 A1 | 5/2012 | Barnscheid et al. |
| 2012/0141583 A1 | 6/2012 | Mannion et al. |
| 2012/0202838 A1 | 8/2012 | Ghosh et al. |
| 2012/0225901 A1 | 9/2012 | Leyendecker et al. |
| 2012/0231083 A1 | 9/2012 | Carley et al. |
| 2012/0251637 A1 | 10/2012 | Bartholomaus et al. |
| 2012/0277319 A1 | 11/2012 | Steigerwald et al. |
| 2012/0321716 A1 | 12/2012 | Vachon et al. |
| 2013/0017262 A1 | 1/2013 | Mullen et al. |
| 2013/0028970 A1 | 1/2013 | Schwier et al. |
| 2013/0028972 A1 | 1/2013 | Schwier et al. |
| 2013/0059010 A1 | 3/2013 | Herry et al. |
| 2013/0090349 A1 | 4/2013 | GeiLer et al. |
| 2013/0129825 A1 | 5/2013 | Billoet et al. |
| 2013/0129826 A1 | 5/2013 | GeiLer et al. |
| 2013/0171075 A1 | 7/2013 | Arkenau-Maric et al. |
| 2013/0209557 A1 | 8/2013 | Barnscheid |
| 2013/0225625 A1 | 8/2013 | Barnscheid et al. |
| 2013/0251643 A1 | 9/2013 | Bartholomäus et al. |
| 2013/0289062 A1 | 10/2013 | Kumar et al. |
| 2013/0303623 A1 | 11/2013 | Barnscheid et al. |
| 2013/0330409 A1 | 12/2013 | Mohammad |
| 2014/0010874 A1 | 1/2014 | Sackler |
| 2014/0034885 A1 | 2/2014 | Leech |
| 2014/0079780 A1 | 3/2014 | Arkenau Maric et al. |
| 2014/0080858 A1 | 3/2014 | Bartholomäus et al. |
| 2014/0080915 A1 | 3/2014 | Bartholomäus et al. |
| 2014/0094481 A1 | 4/2014 | Fleischer et al. |
| 2014/0112984 A1 | 4/2014 | Arkenau Maric et al. |
| 2014/0112989 A1 | 4/2014 | Bartholomäus et al. |
| 2014/0170079 A1 | 6/2014 | Arkenau Maric et al. |
| 2014/0186440 A1 | 7/2014 | Han et al. |
| 2014/0275143 A1 | 9/2014 | Devarakonda et al. |
| 2014/0356426 A1 | 12/2014 | Barnscheid et al. |
| 2014/0356428 A1 | 12/2014 | Barnscheid et al. |
| 2014/0378498 A1 | 12/2014 | Devarakonda et al. |
| 2015/0017250 A1 | 1/2015 | Wening et al. |
| 2015/0030677 A1 | 1/2015 | Adjei et al. |
| 2015/0064250 A1 | 3/2015 | Ghebre-Sellassie et al. |
| 2015/0079150 A1 | 3/2015 | Fischer et al. |
| 2015/0118300 A1 | 4/2015 | Haswani et al. |
| 2015/0118302 A1 | 4/2015 | Haswani et al. |
| 2015/0118303 A1 | 4/2015 | Haswani et al. |
| 2015/0190348 A1 | 7/2015 | Haksar et al. |
| 2015/0374630 A1 | 12/2015 | Arkenau Maric et al. |
| 2016/0089439 A1 | 3/2016 | Rajagopalan |
| 2016/0175256 A1 | 6/2016 | Bartholomaeus et al. |
| 2016/0184297 A1 | 6/2016 | Arkenau-Maric et al. |
| 2016/0256456 A1 | 9/2016 | Caruso et al. |
| 2016/0263037 A1 | 9/2016 | Arkenau-Maric et al. |
| 2016/0361308 A1 | 12/2016 | Bartholomaeus et al. |
| 2016/0367549 A1 | 12/2016 | Bartholomaeus et al. |
| 2017/0027886 A1 | 2/2017 | Bartholomaeus et al. |

FOREIGN PATENT DOCUMENTS

| | | |
|---|---|---|
| AR | 049562 A1 | 8/2006 |
| AR | 049839 A1 | 9/2006 |
| AR | 053304 A1 | 5/2007 |
| AR | 054222 A1 | 6/2007 |
| AR | 054328 A1 | 6/2007 |
| AU | 769807 B2 | 3/2001 |
| AU | 2003237944 A1 | 12/2003 |
| AU | 2003274071 A1 | 5/2004 |
| AU | 2003278133 A1 | 5/2004 |
| AU | 2003279317 A1 | 5/2004 |
| AU | 2004264666 B2 | 2/2005 |
| AU | 2004264667 A1 | 2/2005 |
| AU | 2004308653 B2 | 4/2005 |
| AU | 2005259476 B2 | 1/2006 |
| AU | 2005259478 B2 | 1/2006 |
| AU | 2006210145 A1 | 8/2006 |
| AU | 2006210145 B2 | 8/2006 |
| AU | 2009207796 A1 | 7/2009 |
| AU | 2009243681 A1 | 11/2009 |
| AU | 2009299810 B2 | 4/2010 |
| AU | 2006311116 B2 | 1/2013 |
| BR | P10413318 A | 10/2006 |
| BR | P10413361 A | 10/2006 |
| BR | P10513300 A | 5/2008 |
| BR | P10606145 A2 | 2/2009 |
| CA | 0722109 A | 11/1965 |
| CA | 2082573 C | 5/1993 |
| CA | 2577233 A1 | 10/1997 |
| CA | 2650637 A1 | 10/1997 |
| CA | 2229621 A1 | 3/1998 |
| CA | 2317747 A1 | 7/1999 |
| CA | 2343234 A1 | 3/2000 |
| CA | 2352874 A1 | 6/2000 |
| CA | 2414349 A1 | 1/2002 |
| CA | 2456322 A1 | 2/2003 |
| CA | 2502965 A1 | 5/2004 |
| CA | 2503155 A1 | 5/2004 |
| CA | 2534925 A1 | 2/2005 |
| CA | 2534932 A1 | 2/2005 |
| CA | 2489855 A1 | 4/2005 |
| CA | 2551231 A1 | 7/2005 |
| CA | 2572352 A1 | 1/2006 |
| CA | 2572491 A1 | 1/2006 |
| CA | 2595954 A1 | 7/2006 |
| CA | 2229650 C | 8/2006 |
| CA | 2594713 A1 | 8/2006 |
| CA | 2595979 A1 | 8/2006 |
| CA | 2625055 A1 | 4/2007 |
| CA | 2713128 A1 | 7/2009 |
| CA | 2723438 A1 | 11/2009 |
| CA | 2595954 C | 1/2011 |
| CH | 689109 A5 | 10/1998 |
| CL | 20162004 | 5/2005 |
| CL | 201742004 | 5/2005 |
| CL | 200403308 A1 | 9/2005 |
| CL | 200500952 | 11/2005 |
| CL | 200501624 | 12/2005 |
| CL | 200501625 | 6/2006 |
| CL | 424-2013 | 3/2012 |
| CL | 437-2013 | 3/2012 |
| CN | 87102755 A | 10/1987 |
| CN | 1135175 A | 11/1996 |
| CN | 1473562 A | 2/2004 |
| CN | 1980643 A | 4/2005 |
| CN | 101010071 A | 6/2005 |
| CN | 1671475 A | 9/2005 |
| CN | 101022787 A | 1/2006 |
| CN | 1863513 A | 11/2006 |
| CN | 1863514 A | 11/2006 |
| CN | 1917862 A | 2/2007 |
| CN | 1942174 A | 4/2007 |
| CN | 101011395 A | 8/2007 |
| CN | 101027044 A | 8/2007 |
| CN | 101057849 A | 10/2007 |
| CN | 101484135 A | 11/2007 |
| CN | 101091721 A | 12/2007 |
| CN | 101111232 A | 1/2008 |
| CN | 101175482 A | 2/2008 |
| CN | 101370485 A | 2/2009 |
| CN | 101394839 A | 3/2009 |
| CN | 101578096 A | 11/2009 |
| CN | 101652128 A | 2/2010 |
| CN | 102413835 A | 4/2012 |
| CN | 102821757 A | 12/2012 |
| DE | 2530563 A1 | 1/1977 |
| DE | 4229085 A1 | 3/1994 |
| DE | 4309528 A1 | 9/1994 |
| DE | 4446470 A1 | 6/1996 |
| DE | 69400215 T2 | 10/1996 |
| DE | 19522899 C1 | 12/1996 |
| DE | 2808505 A1 | 1/1997 |
| DE | 19753534 A1 | 6/1999 |
| DE | 19800689 C1 | 7/1999 |
| DE | 19800698 A1 | 7/1999 |
| DE | 19822979 A1 | 12/1999 |
| DE | 69229881 T2 | 12/1999 |
| DE | 19855440 A1 | 6/2000 |

(56) References Cited

FOREIGN PATENT DOCUMENTS

| | | |
|---|---|---|
| DE | 19856147 A1 | 6/2000 |
| DE | 19940740 A1 | 3/2001 |
| DE | 19960494 A1 | 6/2001 |
| DE | 10036400 A1 | 6/2002 |
| DE | 69429710 T2 | 8/2002 |
| DE | 10250083 A1 | 12/2003 |
| DE | 10250084 A1 | 5/2004 |
| DE | 10250087 A1 | 5/2004 |
| DE | 10250088 A1 | 5/2004 |
| DE | 10336400 A1 | 3/2005 |
| DE | 10361596 A1 | 9/2005 |
| DE | 102004019916 A1 | 11/2005 |
| DE | 102004020220 A1 | 11/2005 |
| DE | 102004032049 A1 | 1/2006 |
| DE | 102004032051 A1 | 1/2006 |
| DE | 102004032103 A1 | 1/2006 |
| DE | 102005005446 A1 | 8/2006 |
| DE | 102005005449 A1 | 8/2006 |
| DE | 102007011485 A1 | 9/2008 |
| DK | 1658055 T3 | 7/2007 |
| DK | 1658054 T3 | 10/2007 |
| DK | 1515702 T3 | 1/2009 |
| EC | SP066345 A | 8/2006 |
| EP | 0008131 A1 | 2/1980 |
| EP | 0043254 A1 | 1/1982 |
| EP | 0008131 B1 | 12/1982 |
| EP | 0177893 A2 | 4/1986 |
| EP | 0216453 A2 | 4/1987 |
| EP | 0226061 A2 | 6/1987 |
| EP | 0228417 A1 | 7/1987 |
| EP | 0229652 A2 | 7/1987 |
| EP | 0232877 A2 | 8/1987 |
| EP | 0239973 A2 | 10/1987 |
| EP | 0240906 A2 | 10/1987 |
| EP | 0261616 A2 | 3/1988 |
| EP | 0261616 A3 | 3/1988 |
| EP | 0270954 A1 | 6/1988 |
| EP | 0277289 A1 | 8/1988 |
| EP | 0293066 A2 | 11/1988 |
| EP | 0328775 A1 | 8/1989 |
| EP | 0358105 A1 | 3/1990 |
| EP | 0228417 B1 | 9/1990 |
| EP | 0229652 B1 | 10/1991 |
| EP | 0477135 A1 | 3/1992 |
| EP | 0277289 B1 | 4/1992 |
| EP | 0293066 B1 | 4/1993 |
| EP | 0270954 B1 | 5/1993 |
| EP | 0544144 A1 | 6/1993 |
| EP | 0583726 A2 | 2/1994 |
| EP | 0598606 A1 | 5/1994 |
| EP | 0636370 A1 | 2/1995 |
| EP | 0641195 A1 | 3/1995 |
| EP | 0647448 A1 | 4/1995 |
| EP | 0654263 A1 | 5/1995 |
| EP | 0661045 A1 | 7/1995 |
| EP | 0675710 A1 | 10/1995 |
| EP | 0682945 A2 | 11/1995 |
| EP | 0693475 A1 | 1/1996 |
| EP | 0820693 A1 | 1/1996 |
| EP | 0696598 A1 | 2/1996 |
| EP | 0216453 B1 | 3/1996 |
| EP | 0583726 B1 | 11/1996 |
| EP | 0756480 A1 | 2/1997 |
| EP | 0760654 A1 | 3/1997 |
| EP | 0761211 A1 | 3/1997 |
| EP | 0780369 A1 | 6/1997 |
| EP | 0785775 A1 | 7/1997 |
| EP | 0809488 A1 | 12/1997 |
| EP | 0820698 A1 | 1/1998 |
| EP | 0820753 A2 | 1/1998 |
| EP | 0857062 A2 | 8/1998 |
| EP | 0864324 A1 | 9/1998 |
| EP | 0864326 A2 | 9/1998 |
| EP | 0598606 B1 | 6/1999 |
| EP | 0675710 B1 | 8/1999 |
| EP | 0980894 A1 | 2/2000 |
| EP | 0988106 A1 | 3/2000 |
| EP | 1014941 A1 | 7/2000 |
| EP | 1070504 A1 | 1/2001 |
| EP | 1127871 A1 | 8/2001 |
| EP | 1138321 A2 | 10/2001 |
| EP | 1152026 A1 | 11/2001 |
| EP | 1138321 A3 | 1/2002 |
| EP | 1166776 A2 | 1/2002 |
| EP | 1201233 A1 | 5/2002 |
| EP | 0661045 B1 | 7/2002 |
| EP | 1250045 A2 | 10/2002 |
| EP | 1251120 A1 | 10/2002 |
| EP | 1293127 A2 | 3/2003 |
| EP | 1293195 A1 | 3/2003 |
| EP | 1293196 A2 | 3/2003 |
| EP | 1127871 B1 | 9/2003 |
| EP | 1201233 B1 | 12/2004 |
| EP | 1251120 B1 | 12/2004 |
| EP | 1492506 B1 | 1/2005 |
| EP | 1166776 B1 | 2/2005 |
| EP | 1502592 A1 | 2/2005 |
| EP | 1658054 A1 | 2/2005 |
| EP | 1658055 A1 | 2/2005 |
| EP | 1515702 B1 | 3/2005 |
| EP | 1527775 A1 | 4/2005 |
| EP | 1558221 A1 | 8/2005 |
| EP | 1558257 A1 | 8/2005 |
| EP | 1560585 B1 | 8/2005 |
| EP | 1611880 A2 | 1/2006 |
| EP | 1658054 B1 | 5/2006 |
| EP | 1138321 B1 | 1/2007 |
| EP | 1740161 A2 | 1/2007 |
| EP | 1658055 B1 | 3/2007 |
| EP | 1765303 A1 | 3/2007 |
| EP | 1786403 A1 | 5/2007 |
| EP | 1558221 B1 | 6/2007 |
| EP | 1813276 A1 | 8/2007 |
| EP | 1842533 A2 | 10/2007 |
| EP | 1845955 A1 | 10/2007 |
| EP | 1845956 A1 | 10/2007 |
| EP | 1859789 A1 | 11/2007 |
| EP | 1980245 A1 | 10/2008 |
| EP | 1897545 A1 | 12/2008 |
| EP | 2131830 A2 | 12/2009 |
| EP | 2246063 A1 | 11/2010 |
| EP | 2249811 A1 | 11/2010 |
| EP | 2273983 A1 | 1/2011 |
| EP | 2402004 A2 | 1/2012 |
| ES | 2336571 T3 | 12/2004 |
| ES | 2260042 T3 | 11/2006 |
| ES | 2285497 T3 | 11/2007 |
| ES | 2288621 T3 | 1/2008 |
| ES | 2289542 T3 | 2/2008 |
| ES | 2315505 T3 | 4/2009 |
| GB | 1147210 A | 4/1969 |
| GB | 1567727 A | 5/1980 |
| GB | 2047095 A | 11/1980 |
| GB | 2057878 A | 4/1981 |
| GB | 2238478 A | 6/1991 |
| HR | 20070456 T3 | 6/2007 |
| HR | 20070272 T3 | 11/2007 |
| JP | S36-022895 | 11/1961 |
| JP | S55162714 A | 12/1980 |
| JP | S5659708 A | 5/1981 |
| JP | S56169622 A | 12/1981 |
| JP | S62240061 A | 10/1987 |
| JP | H0249719 A | 2/1990 |
| JP | 03-501737 A | 4/1991 |
| JP | H0517566 A | 1/1993 |
| JP | H06507645 A | 9/1994 |
| JP | 08053331 A | 2/1996 |
| JP | 8-505076 A | 6/1996 |
| JP | H09508410 A | 8/1997 |
| JP | H1057450 A | 3/1998 |
| JP | H10251149 A | 9/1998 |
| JP | 2000513333 A | 10/2000 |
| JP | 2002524150 A | 8/2002 |
| JP | 2002-275175 A | 9/2002 |

(56) References Cited

FOREIGN PATENT DOCUMENTS

| | | | |
|---|---|---|---|
| JP | 2003113119 A | 4/2003 |
| JP | 2003125706 A | 5/2003 |
| JP | 2003526598 A | 9/2003 |
| JP | 2004143071 A | 5/2004 |
| JP | 2004530676 A | 10/2004 |
| JP | 2005506965 A | 3/2005 |
| JP | 2005515152 A | 5/2005 |
| JP | 2005534664 A | 11/2005 |
| JP | 2007501201 A | 1/2007 |
| JP | 2007501202 A | 1/2007 |
| JP | 2007513147 A | 5/2007 |
| JP | 2007533692 A | 11/2007 |
| JP | 2008024603 A | 2/2008 |
| JP | 2008504327 A | 2/2008 |
| JP | 2008528654 A | 7/2008 |
| JP | 2009523833 A | 6/2009 |
| JP | 2009524626 A | 7/2009 |
| JP | 2009531453 A | 9/2009 |
| JP | 2009536927 A | 10/2009 |
| JP | 2009537456 A | 10/2009 |
| JP | 2010505949 A | 2/2010 |
| JP | 2010527285 A | 8/2010 |
| JP | 2010534204 A | 11/2010 |
| JP | 2011504455 A | 2/2011 |
| JP | 2011506493 A | 3/2011 |
| JP | 2011510034 A | 3/2011 |
| JP | WO 2011/059074 A1 | 5/2011 |
| JP | 2012515735 A | 7/2012 |
| JP | 2012528845 A | 11/2012 |
| JP | 2013523804 A | 6/2013 |
| JP | 2013155124 A | 8/2013 |
| JP | 2013536810 A | 9/2013 |
| JP | 2014505736 A | 3/2014 |
| JP | 2014528437 A | 10/2014 |
| JP | 6085307 B2 | 2/2017 |
| JP | 2013523780 A | 6/2017 |
| KR | 1020060069832 A | 6/2006 |
| KR | 20070039041 A | 4/2007 |
| KR | 20070111510 A | 11/2007 |
| KR | 20090085312 A | 8/2009 |
| KR | 20100111303 A | 10/2010 |
| KR | 20110016921 A | 2/2011 |
| MX | 2007000008 A | 3/2007 |
| MX | 2007000009 A | 3/2007 |
| MX | 2007009393 A | 8/2007 |
| MX | 2010008138 A | 8/2010 |
| MX | 2010012039 A | 11/2010 |
| NO | 20061054 A | 3/2006 |
| NO | 20070578 A | 1/2007 |
| NO | 20074412 A | 11/2007 |
| NZ | 528302 A | 2/2007 |
| PT | 1699440 E | 12/2004 |
| PT | 1658054 E | 5/2006 |
| PT | 1658055 E | 7/2007 |
| PT | 1515702 E | 12/2008 |
| RU | 2131244 C1 | 6/1999 |
| RU | 2198197 C2 | 2/2003 |
| RU | 2220715 C2 | 1/2004 |
| RU | 2328275 C2 | 5/2004 |
| RU | 2396944 C2 | 7/2004 |
| RU | 2326654 C2 | 9/2005 |
| RU | 2339365 C2 | 12/2007 |
| RU | 2354357 C2 | 12/2007 |
| RU | 2007103712 A | 9/2008 |
| RU | 2007103707 A | 11/2008 |
| RU | 2007132975 A | 4/2009 |
| RU | 2567723 C2 | 11/2015 |
| SI | 1515702 T1 | 4/2009 |
| SI | 1699440 T1 | 11/2009 |
| SK | 10612003 A3 | 1/2004 |
| SU | 1759445 A1 | 9/1992 |
| TW | 1254634 B | 5/2006 |
| WO | WO 1980/000841 A1 | 5/1980 |
| WO | WO 1989/005624 A1 | 6/1989 |
| WO | WO 1990/003776 A1 | 4/1990 |
| WO | WO 1993/006723 A1 | 4/1993 |
| WO | WO 93/10765 A1 | 6/1993 |
| WO | WO 1993/010758 A1 | 6/1993 |
| WO | WO 1993/011749 A1 | 6/1993 |
| WO | WO 1993/023017 A1 | 11/1993 |
| WO | WO 1994/006414 A1 | 3/1994 |
| WO | WO 1994/008567 A1 | 4/1994 |
| WO | WO 1995/017174 A1 | 6/1995 |
| WO | WO 1995/020947 A1 | 8/1995 |
| WO | WO 1995/022319 A1 | 8/1995 |
| WO | WO 1995/030422 A1 | 11/1995 |
| WO | WO 1996/000066 A1 | 1/1996 |
| WO | WO 1996/003979 A1 | 2/1996 |
| WO | WO 1996/014058 A1 | 5/1996 |
| WO | WO 1997/000673 A1 | 1/1997 |
| WO | WO 1997/033566 A2 | 9/1997 |
| WO | WO 1997/049384 A1 | 12/1997 |
| WO | WO 1998/035655 A3 | 2/1998 |
| WO | WO 1998/020073 A2 | 5/1998 |
| WO | WO 1998/028698 A1 | 7/1998 |
| WO | WO 1998/035655 A2 | 8/1998 |
| WO | WO 1998/051758 A1 | 11/1998 |
| WO | WO 1999/012864 A1 | 3/1999 |
| WO | WO 1999/032120 A1 | 7/1999 |
| WO | WO 1999/044591 A1 | 9/1999 |
| WO | WO 1999/045887 A2 | 9/1999 |
| WO | WO 1999/048481 A1 | 9/1999 |
| WO | WO 00/15261 A1 | 3/2000 |
| WO | WO 2000/013647 A1 | 3/2000 |
| WO | WO 2000/033835 A1 | 6/2000 |
| WO | WO 2000/040205 A2 | 7/2000 |
| WO | WO 2001/008661 A2 | 2/2001 |
| WO | WO 2001/012230 A1 | 2/2001 |
| WO | WO 2001/015667 A1 | 3/2001 |
| WO | WO 2001/052651 A2 | 7/2001 |
| WO | WO 2001/058451 A1 | 8/2001 |
| WO | WO 2001/097783 A1 | 12/2001 |
| WO | WO 2002/026061 A1 | 4/2002 |
| WO | WO 2002/026062 A1 | 4/2002 |
| WO | WO 2002/026928 A1 | 4/2002 |
| WO | WO 2002/035991 A2 | 5/2002 |
| WO | WO 2002/071860 A1 | 9/2002 |
| WO | WO 2002/088217 A1 | 11/2002 |
| WO | WO 2002/094254 A2 | 11/2002 |
| WO | WO 2003/006723 A1 | 1/2003 |
| WO | WO 2003/007802 A2 | 1/2003 |
| WO | WO 2003/013433 A2 | 2/2003 |
| WO | WO 2003/013476 A1 | 2/2003 |
| WO | WO 2003/013479 A1 | 2/2003 |
| WO | WO 2003/013538 A1 | 2/2003 |
| WO | WO 2003/015531 A2 | 2/2003 |
| WO | WO 2003/018015 A1 | 3/2003 |
| WO | WO 2003/024426 A1 | 3/2003 |
| WO | WO 2003/024430 A1 | 3/2003 |
| WO | WO 2003/026624 A1 | 4/2003 |
| WO | WO 2003/026743 A2 | 4/2003 |
| WO | WO 2003/028698 A1 | 4/2003 |
| WO | WO 2003/028990 A1 | 4/2003 |
| WO | WO 2003/031546 A1 | 4/2003 |
| WO | WO 2003/035029 A1 | 5/2003 |
| WO | WO 2003/035053 A1 | 5/2003 |
| WO | WO 2003/035054 A1 | 5/2003 |
| WO | WO 2003/035177 A2 | 5/2003 |
| WO | WO 2003/039561 A1 | 5/2003 |
| WO | WO 2003/049689 A2 | 6/2003 |
| WO | WO 2003/053417 A2 | 7/2003 |
| WO | WO 2003/068392 A1 | 8/2003 |
| WO | WO 2003/070191 A1 | 8/2003 |
| WO | WO 2003/092648 A1 | 11/2003 |
| WO | WO 2003/094812 A1 | 11/2003 |
| WO | WO 2003/105808 A1 | 12/2003 |
| WO | WO 2004/004693 A1 | 1/2004 |
| WO | WO 2004/043967 A2 | 2/2004 |
| WO | WO 2004/026262 A2 | 4/2004 |
| WO | WO 2004/026263 A2 | 4/2004 |
| WO | WO 2004/026280 A2 | 4/2004 |
| WO | WO 2004/037222 A2 | 5/2004 |
| WO | WO 2004/037230 A1 | 5/2004 |
| WO | WO 2004/037259 A1 | 5/2004 |

(56) References Cited

FOREIGN PATENT DOCUMENTS

| | | |
|---|---|---|
| WO | WO 2004/037260 A1 | 5/2004 |
| WO | WO 2004/043449 A1 | 5/2004 |
| WO | WO 2004/066910 A2 | 8/2004 |
| WO | WO 2004/078212 A1 | 9/2004 |
| WO | WO 2004/084869 A1 | 10/2004 |
| WO | WO 2004/093801 A2 | 11/2004 |
| WO | WO 2004/093819 A2 | 11/2004 |
| WO | WO 2004/098567 A2 | 11/2004 |
| WO | WO 2004/100894 A2 | 11/2004 |
| WO | WO 2005/016313 A1 | 2/2005 |
| WO | WO 2005/016314 A1 | 2/2005 |
| WO | WO 2005/032524 A2 | 4/2005 |
| WO | WO 2005/041968 A2 | 5/2005 |
| WO | WO 2005/053587 A1 | 6/2005 |
| WO | WO 2005/053656 A1 | 6/2005 |
| WO | WO 2005/055981 A2 | 6/2005 |
| WO | WO 2005/060942 A1 | 7/2005 |
| WO | WO 2005/063214 A1 | 7/2005 |
| WO | WO 2005/065646 A2 | 7/2005 |
| WO | WO 2005/066183 A1 | 7/2005 |
| WO | WO 2005/079760 A1 | 9/2005 |
| WO | WO 2005/102286 A1 | 11/2005 |
| WO | WO 2005/102294 A2 | 11/2005 |
| WO | WO 2005/102294 A3 | 11/2005 |
| WO | WO 2005/105036 A1 | 11/2005 |
| WO | WO 2006/002883 A1 | 1/2006 |
| WO | WO 2006/002884 A1 | 1/2006 |
| WO | WO 2006/002886 A1 | 1/2006 |
| WO | WO 2006/002884 B1 | 3/2006 |
| WO | WO 2006/039692 A2 | 4/2006 |
| WO | WO 2006/058249 A2 | 6/2006 |
| WO | WO 2006/082097 A1 | 8/2006 |
| WO | WO 2006/082099 A1 | 8/2006 |
| WO | WO 2006/105615 A1 | 10/2006 |
| WO | WO 2006/128471 A2 | 12/2006 |
| WO | WO 2007/005716 A2 | 1/2007 |
| WO | WO 2007/008752 A2 | 1/2007 |
| WO | WO 2007/014061 A2 | 2/2007 |
| WO | WO 2007/048233 A1 | 5/2007 |
| WO | WO 2007/053698 A2 | 5/2007 |
| WO | WO 2007/085024 A2 | 7/2007 |
| WO | WO 2007/085024 A3 | 7/2007 |
| WO | WO 2007/093642 A2 | 8/2007 |
| WO | WO 2007/103105 A2 | 9/2007 |
| WO | WO 2007/103286 A2 | 9/2007 |
| WO | WO 2007/112273 A2 | 10/2007 |
| WO | WO 2007/112285 A2 | 10/2007 |
| WO | WO 2007/112286 A2 | 10/2007 |
| WO | WO 2007/131357 A1 | 11/2007 |
| WO | WO 2007/138466 A2 | 12/2007 |
| WO | WO 2008/023261 A1 | 2/2008 |
| WO | WO 2008/033523 A1 | 3/2008 |
| WO | WO 2008/045060 A1 | 4/2008 |
| WO | WO 2008/069641 A2 | 6/2008 |
| WO | WO 2008/086804 A2 | 7/2008 |
| WO | WO 2008/107149 A2 | 9/2008 |
| WO | WO 2008/107149 A3 | 9/2008 |
| WO | WO 2008/109462 A2 | 9/2008 |
| WO | WO 2008/132707 A1 | 11/2008 |
| WO | WO 2008/142627 A2 | 11/2008 |
| WO | WO 2008/148798 A2 | 12/2008 |
| WO | WO 2009/005803 A1 | 1/2009 |
| WO | WO 2009/014534 A1 | 1/2009 |
| WO | WO 2009/034541 A2 | 3/2009 |
| WO | WO 2009/034541 A3 | 3/2009 |
| WO | WO 2009/034541 A9 | 3/2009 |
| WO | WO 2009/035474 A1 | 3/2009 |
| WO | WO 2009/051819 A1 | 4/2009 |
| WO | WO 2009/076764 A1 | 6/2009 |
| WO | WO 2009/092601 A1 | 7/2009 |
| WO | WO 2009/110005 A2 | 9/2009 |
| WO | WO 2009/112273 A2 | 9/2009 |
| WO | WO 2009/135680 A1 | 11/2009 |
| WO | WO 2010/022193 A2 | 2/2010 |
| WO | WO 2010/037854 A2 | 4/2010 |
| WO | WO 2010/044842 A1 | 4/2010 |
| WO | WO 2010/057036 A2 | 5/2010 |
| WO | WO 2010/066034 A1 | 6/2010 |
| WO | WO 2010/069050 A1 | 6/2010 |
| WO | WO 2010/083843 A1 | 7/2010 |
| WO | WO 2010/083894 A1 | 7/2010 |
| WO | WO 2010/088911 A1 | 8/2010 |
| WO | WO 2010/105672 A1 | 9/2010 |
| WO | WO 2010/140007 A2 | 12/2010 |
| WO | WO 2010/140007 A9 | 12/2010 |
| WO | WO 2010/149169 A2 | 12/2010 |
| WO | WO 2011/008298 A2 | 1/2011 |
| WO | WO 2011/009602 A1 | 1/2011 |
| WO | WO 2011/009603 A1 | 1/2011 |
| WO | WO 2011/009604 A1 | 1/2011 |
| WO | WO 2011/095314 A2 | 8/2011 |
| WO | WO 2011/095314 A3 | 8/2011 |
| WO | WO 2011/124953 A2 | 10/2011 |
| WO | WO 2011/124953 A3 | 10/2011 |
| WO | WO 2011/128630 A2 | 10/2011 |
| WO | WO 2011/141241 A1 | 11/2011 |
| WO | WO 2011/154414 A1 | 12/2011 |
| WO | WO 2012/028317 A1 | 3/2012 |
| WO | WO 2012/028318 A1 | 3/2012 |
| WO | WO 2012/028319 A1 | 3/2012 |
| WO | WO 2012/061779 A1 | 5/2012 |
| WO | WO 2012/076907 A2 | 6/2012 |
| WO | WO 2012/085657 A2 | 6/2012 |
| WO | WO 2012/119727 A1 | 9/2012 |
| WO | WO 2012/166474 A1 | 12/2012 |
| WO | WO 2013/003845 A1 | 1/2013 |
| WO | WO 2013/017234 A1 | 2/2013 |
| WO | WO 2013/017242 A1 | 2/2013 |
| WO | WO 2013/025449 A1 | 3/2013 |
| WO | WO 2013/030177 A1 | 3/2013 |
| WO | WO 2013/050539 A2 | 4/2013 |
| WO | WO 2013/072395 A1 | 5/2013 |
| WO | WO 2013/084059 A1 | 6/2013 |
| WO | WO 2013/127830 A1 | 9/2013 |
| WO | WO 2013/127831 A1 | 9/2013 |
| WO | WO 2013/128276 A2 | 9/2013 |
| WO | WO 2013/156453 A1 | 10/2013 |
| WO | WO 2013/167735 A1 | 11/2013 |
| WO | WO 2014/032741 A1 | 3/2014 |
| WO | WO 2014/059512 A1 | 4/2014 |
| WO | WO 2014/140231 A1 | 9/2014 |
| WO | WO 2014/190440 A1 | 12/2014 |
| WO | WO 2014/191396 A1 | 12/2014 |
| WO | WO 2014/191397 A1 | 12/2014 |
| WO | WO 2015/004245 A1 | 1/2015 |
| WO | WO 2015/048597 A1 | 4/2015 |
| WO | WO 2015/103379 A1 | 7/2015 |
| WO | WO 2015/120201 A1 | 8/2015 |
| WO | WO 2017/178658 | 10/2017 |

OTHER PUBLICATIONS

Albertini, B. "New spray congealing atomizer for the microencapsulation of highly concentrated solid and liquid substances" European Journal of Pharmaceutics and Biopharmaceutics 69 (2008) 348-357.

Alekseeva et al, Chemical-Pharmaceutical Journal, vol. 41, No. 9, 2007, 49-52. (Full translation attached.).

Almeida, A. et al., Ethylene vinyl acetate as matrix for oral sustained release dosage forms produced via hot-melt extrusion, European Journal of Pharmaceutics and Biopharmaceutics 77 (2011) 297-305.

Almeida, A. et al., Sustained release from hot-melt extruded matrices based on ethylene vinyl acetate and polyethylene oxide, European Journal of Pharmaceutics and Biopharmaceutics 82 (2012) 526-533.

Andre et al., "O-Demethylation of Opiod Derivatives With Methane Sulfonic Acid/Methoinine: Application to the Synthesis of Naloxone and Analogues" Synthetic Comm. 22(16), pp. 2313-2327, 1992.

Apicella A.et al., Biomaterials, vol. 14, No. 2, pp. 83-90, 1993.

Application of a modelling system in the formulation of extended release hydrophilic matrices, Reprinted from Pharmaceutical Technology Europe, Jul. 2006.

(56) References Cited

OTHER PUBLICATIONS

Application of Opadry II, complete film coating system, on metformin HCl extended release matrices containing Polyox water soluble resin, Colorcon Apr. 2009.
Arnold C., "Teen Abuse of Painkiller OxyContin on the Rise," www.npr.org, Dec. 19, 2005.
Augustine, R.L., Catalytic Hydrogenation of a, B-Unsaturated Ketones. III The Effect of Quantity and Type of Catalysts, J. Org Chem. 28(1), pp. 152-155, Abstract 1963.
Avis, Kenneth, Parenteral Preparations. Chapter 85. pp. 1518-1541 In Remington's Pharmaceutical Sciences, 17th Ed, 1985.
Bailey, F.E., et al., "Some properties of poly(ethylene oxide) in aqueous solution," Journal of Applied Polymer Science, vol. 1, Issue No. 1, pp. 56-62, 1959.
Bauer et al. Lehrbuch der Pharmazeutischen Technologie. Eight Edition 2006. Stuttgart, pp. 343-352.
Bauer et al. Lehrbuch der Pharmazeutischen Technologie. Sixth Edition 1999. Stuttgart, pp. IX-XV, Table of contents. (Full English translation attached).
Bauer, Kurt H., et al., Coated Pharmaceutical Dosage Forms—Fundamentals, Manufacturing Techniques, Biopharmaceutical Aspects, Test Methods and Raw Materials, 1st edition, 1998, CRC Press, Medpharm Scientific Publishers. (Preface, Table of Content, List of Abbreviations, Explanation of Terms only).
Baum et al.,"The impact of the addition of naloxone on the use and abuse of pentazocine", Public Health Reports, Jul.-Aug., 1987, vol. 102, No. 4, p. 426-429.
Bingwen et al, 2008, p. 367. (full translation attached).
Block, Lawrence. Medicated Applications. Chapter 88. In Remington's Pharmaceutical Sciences, 17th Ed, 1985.
Borquist et al., "Simulation of the release from a multiparticulate system validated by single pellet and dose release experiements," J. Controlled Release, 97: 453-465 (2004).
Braun, et al. A study of Bite Force. Part 2: Relationship to Various cephalometric Measurements. Angel Orthodontist, vol. 65 (5) pp. 373-377, 1995.
Brown, The Dissolution Procedure: Development and Validation, heading "Study Design", "Time Points" US Pharmacopoeia (USP), vol. 31(5), General Chapter 1092, pp. 1-15, 2006.
Bruce et al, Properties of hot-melt extuded tablet formulations for the colonic delivery of 5-aminosalicylic acid, European Journal of Pharmaceutics and Biopharmaceutics, 59 (2005) 85-97.
Caraballo, Journal of Controlled Release, vol. 69, pp. 345-355, 2000.
Carbopol 71G, retrieved Mar. 10, 2014 from http://www.lubrizol.com/LifeScience/Products/Carbopol71G-NF.html.
Cawello, "Parameters for Compartment-free Pharmacokinetics—Standardization of Study Design, Data Analysis and Reporting" 1999, pp. XI-XIII (table of contents).
Chibuzor et al. "Formulation Development and Evaluation of Drug Release Kinetics from Colon-Targeted Ibuprofen Tablets Based on Eudragit RL 100-Chitosan Interpolyelectrolyte Complexes," Hindawi Publ. Corporation ISRN Pharmaceutics, vol. 2013, Article ID 838403.
Committee for Proprietary Medicinal Products. Note for Guidance on the Investigation of Bioavailability and Bioequivalence. 2001. pp. 1-18.
Coppens et al., "Hypromellose, Ethylcellulose, and Polyethylene Oxide Use in Hot Melt Extrusion"; Pharmaceutical Technology, 62-70, Jan. 2005.
Cornish, P. "Avoid the Crush": hazards of medication administration in patients with dysphagia or a feeding tube, CMA Media Inc., CMAJ. 172(7), pp. 871-872, 2005.
Costa et al. "Modeling and comparison of dissolution profiles"; European Journal of Pharmaceutical Sciences 13 (2001) 123-33.
Crowley M.M. et al., "Stability of polyethylene oxide in matrix tablets prepared by hot-melt extrusion," Biomaterials 23, 2002, pp. 4241-4248.
Crowley MM, Drug Dev Ind Pharm. Sep. 2007; 33(9):909-26. (Abstract only).

Cuesov, Drug Production Technology, Khar'kov, 1999, pp. 351-352.
Dachille et al., "High-pressure Phase Transformations in Laboratory Mechanical Mixers and Mortars", Nature, vol. 186, Apr. 2, 1960, pp. 34 and 71.
Dachille, F. et al., "High-Pressure Phase Transformation in Laboratory Mechanical Mixers and Mortars", 1960., Nature, vol. 186, pp. 1-2 (abstract).
Davies, et al; European Journal of Pharmaceutics and Biopharmaceutics, 67, 2007, pp. 268-276.
Dean, D.A., E.R. Evans, I.H. Hall, Pharmaceutical Packaging Technology, Taylor & Francis, 1st Edition, Nov. 30, 2000 (Publisher description dated Oct. 22, 2010).
Deighan, C.J. et al., Rhabdomyolysis and acute renal failure resulting from alcohol and drug abuse, Q.J. Med, vol. 93, 2000, pp. 29-33.
Dejong (Pharmaceutisch Weekblad Scientific Edition) 1987, p. 24-28.
Dexheimer, Terahertz Spectroscopy: Principles and Applications (Optical Science and Engineering Series), CRC; 1 edition 2007. (Table of content only).
Dierickx et al., "Co-extrusion as manufacturing technique for fixed-dose combination mini-matrices," European Journal of Pharmaceutics and Biopharmaceutics 81 (2012), 683-689.
Disanto, Anthony. Bioavailability and Bioequivalency Testing. Chapter 77. In Remington's Pharmaceutical Sciences, 17th Ed, 1985.
Dow Chemical Company, "Using Dow Excipients for Controlled Release of Drugs in Hydrophilic Matrix Systems", Sep. 2006, pp. 1-36.
Dow Excipients Chem. of Poly. Water Soluble-Resin 2004, pp. 1-2.
Dow Technical Data, POLYOX WSR Solid Dosage Formulation via Melt Extrusion, Feb. 2003, pp. 1-3.
Efentakis M et al. "Evaluation of High Molecular Weight Poly(Oxyethylene) (Polyox) Polymer: Studies of Flow Properties and Release Rates of Furosemide and Captopril from controlled-Release hard Gelatin Capsules", Pharmaceutical Development and Technology, 5 (3), pp. 339-346, 2000.
Eggleston, "The seat of the emetic action of various drugs," J. Pharmacol. Exp. Ther. 7, 225-253 (1915).
El-Egakey, Adel et al, "Hot extruded dosage forms Part I Technology and dissolution kinetics of polymeric matrices" Pharmacerutica Acta Helvetiae, vol. 46, pp. 31-53,Mar. 19, 1970.
El-Sherbiny I.M. et al "Preparation, characterization, swelling and in vitro drug release behaviour of poly[N-acryloylglycine-chitosan] interplymeric pH and thermally-resposive hydrogels", European Polymer Journal, vol. 41, pp. 2584-2591, 2005.
Encyclopedia of Pharmaceutical Technology, Third Edition, vol. 1, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 2, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 3 edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 4, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 5, edited by James Swarbrick PharmaceuTech, Inc., Pinehurst, North Carolinia, USA (Table of Contents only), Oct. 25, 2006.
Encyclopedia of Pharmaceutical Technology, Third Edition, vol. 6, edited by James Swarbrick PharmaceuTech, Inc., Pinehurst, North Carolinia, USA (Table of Contents only), Oct. 25, 2006.
Encyclopedia of Pharmacological Technology, Informa Healthcare, 1st Ed., 1996, vol. 14 (Table of Content only).
Erskine, Jr., Clyde. Quality Assurance and Control. Chapter 83. pp. 1487-1491 in Remington's Pharmaceutical Sciences, 17th Ed, 1985.
Eudragit NE40D web page from Evonik website; downloaded Feb. 24, 2015.
Eudragit RS PO web page from Evonik website; downloaded Feb. 24, 2015.
European Pharmacopeia 5.0; Glyceryl behenate monograph; dated Jan. 2005; downloaded Feb. 24, 2015.

(56) References Cited

OTHER PUBLICATIONS

European Pharmacopoeia 2.9.40 "Uniformity of Dosage Units", 2006, pp. 3370-3373.
European Pharmacopoeia 5.0, 2.9.8 "Resistance to Crushing of Tablets", 2005, p. 235.
European Pharmacopoeia, Third Edition Supplement 2000, Council of Europe, Strasbourg, 2000, pp. 85-107.
European Pharmacopoeia, Third Edition, Council of Europe, Strasbourg, 1997, pp. 127-152.
European Search Report and Opinion Application No. 12002708.1-1219, dated Sep. 24, 2012.
European Search Report and Opinion Application No. 14176277.3-1460, dated Dec. 15, 2014.
European Search Report and Opinion, Application No. 11006253.6-2112, dated Dec. 16, 2011.
European Search Report and Opinion, Application No. 11006254.4-2112, dated Dec. 16, 2011.
European Search Report and Opinion, Application No. 11008131.2-1219, dated Feb. 24, 2012.
European Search Report and Opinion, Application No. 11009129.5-2112, dated Apr. 10, 2012.
European Search Report and Opinion, Application No. 12001296.8-1219, dated Jun. 26, 2012.
European Search Report and Opinion, Application No. 12001301.6-1219, dated Jun. 26, 2012.
European Search Report and Opinion, Application No. 12003743.7-1219, dated Sep. 24, 2012.
European Search Report and Written Opinion for EP Application No. 13169658.5, dated Aug. 6, 2013.
European Search Report and Written Opinion for EP Application No. 13169659.3, dated Aug. 6, 2013.
European Search Report and Written Opinion for EP Application No. 13176309.9-1460, dated Oct. 9, 2013.
European Search Report and Written Opinion for EP Application No. 13197503.9-1460, dated Feb. 18, 2014.
European Search Report and Written Opinion for EP Application No. 13425151.1-1460, dated Mar. 11, 2014.
European Search Report and Written Opinion for EP Application No. 14169801.9-1455 dated Oct. 20, 2014.
Evaluation of Verapamil HCl (240 mg) Extended Release Matrix Formulation Using USP Apparatus III in Biorelevant Dissolution Media, Jul. 2009.
Evonik Industries, Eudragit Application Guidelines, 10th Edition, 2008, (Table of Contents only).
Evonik Rohm GmbH product brochure: EUDRAGIT acrylic polymers for solid oral dosage forms (2009).
Extended European Search Report and Opinion for Application No. EP 15153679.4-1455, dated Jun. 30, 2015.
Extended European Search Report and Opinion for Application No. EP 15165064.5-1455, dated Oct. 16, 2015.
Extended European Search Report and Opinion for Application No. EP 15165065.2-1455, dated Nov. 2, 2015.
Extended European Search Report and Opinion for Application No. EP 15165067.8-1455, dated Nov. 2, 2015.
Extended European Search Report and Opinion for Application No. EP 15165069.4-1455, dated Nov. 2, 2015.
Extended European Search Report and Opinion for Application No. EP 15165070.2-1455, dated Nov. 2, 2015.
Extended European Search Report and Opinion for Application No. EP 15184634.2-1455, dated Mar. 3, 2016.
Fell J.T., et al, "Determinination of Tablet Strength by the Diametral-Compression Test" Journal of Pharmaceutical Sciences, vol. 59, No. 5, May 1970, pp. 688-691.
Follonier N. et al., "Evaluation of hot-melt extrusion as a new technique for the production of polymer-based pellets for sustained release capsules containing high loadings of freely soluble drugs," Drug Development and Industrial Pharmacy, 20(8), pp. 1323-1339, 1994.
Follonier, N. et al., "Various ways of modulating the release of dltiazem hydrochloride from hot-melt extruded sustained release pellets prepared using polymeric materials" Journal of Controlled Release 36, pp. 243-250, 1995.
Formulation of Polyox ER Matrices for a Highly Soluble Active, Colorcon Jul. 2009.
Foye, W., Principles of Medicinal Chemistry; Analgesics pp. 241-242, at 241 (1989).
Foye, W., Principles of Medicinal Chemistry; Structural Features and Pharmacologic Activity, pp. 63-66 at 65 (1989).
Freed et al., "pH Control of Nucleophilic/electrophilic oxidation", International Journal of Pharmaceutics, vol. 357, pp. 180-188 (2008).
Giles R. et al. Plastic Packaging Materials. Chapter 81. pp. 1473-1477 In Remington's Pharmaceutical Sciences, 17th Ed, 1985.
Goodman and Gilman, "The Pharmacological Basis of Therapeutics, Seventh Edition", MacMillan Publishing Company, Table of Contents. 1985.
Goodman and Gilman, 1985, 7th edition, chapter 22, 491-530.
Goodman and Gilman, 1985, 7th edition, chapter 23, 533-579.
Graham N.B., Poly(Ethylene Glycol) Chemistry: Biotechnical and Biomedical Applications, p. 263-291 Chapter 17, 1992.
Griffin W, "Classification of Surface-Active Agents by HLB" Journal of the Society of Cosmetic Chemists, Atlas Powder Company, 1949, pp. 311-326.
Griffith, et al. "Tablet Crushing and the Law: The Implications for Nursing" Professional Nurse 19(1), pp. 41-42, 2003.
Gryczke et al, "Development and evaluation of orally disintegrating tablets (ODTs) containing Ibuprofen granules prepared by hot melt extrusion", Colloids and surfaces., B, Biointerfaces, Elsevier, Amsteram, NL, vol. 86, No. 2, Apr. 5, 2011, pp. 275-284.
Guidance for Industry—Bioavailability and Bioequivalence—Studies for Orally Administered Drug Products—General Considerations, FDA, BP, Announced in the Federal Register: vol. 68, No. 53/Mar. 19, 2003.
Guidance for Industry—Statistical Approaches to Establishing Bioequivalence, FDA, BP, Jan. 2001.
Handbook of Pharmaceutical Excipients, 1986, American Pharmaceutical Association, Washington, DC and London (Table of Content Only).
Handbuch der Kunststoff-Extrusionstechnik 1, "Grundlagen" in Chapter 1.2 "Klassifizierung von Extrudern", pp. 3-7. 1989. (Full english translation attached).
Hanning C.D.et al. "The Morphone Hydrogel Suppository. A New Sustained release Rectal Preparation", British Journal of Anaesthesia, 61, pp. 221-227, 1988.
Hartauer, Kerry J. "Influence of Peroxide Impurities in Povidone and Crospovidone on the Stability of Raloxife" Pharma. Dev. & Tech, 5 (3) 303-310 (2000).
Henriest D. et al. In vitro and in vivo evaluation of starch-based hot stage extruded double matrix systems. Journal of Controlled Release. 2001, vol. 75, pp. 391-400.
Hoepfner et al. Fiedler Encyclopedia of Excipients. Sixth Edition, 2007, Aulendorf, Germany; Table of Contents only.
Hong S. et al. Dissolution kinetics and physical characterization of three-layered tablet with poly(ethylene oxide) core matrix capped by Carbopol. Int .J. Pharmacol. 2008, vol. 356, pp. 121-129.
Inert gas—Wikipedia, Dec. 2009, pp. 1-3.
Investigation of a Directly Compressible Metformin HCl 500mg Extended Release Formulation Based on Hypromellose, Colorcon Jul. 2009.
James, A. "The legal and clinical implications of crushing tablet medication", Nurse Times 100(50), 28-33, 2004.
Janicki S. et al. "Slow-Release Microballs: Method of Preparation", Acta Pharm. Technol. 33 (3) 154-155, 1987.
Jannetto, P. et al, "Oxycodone: Recognition and Pharmacogenomics," Toxicology News, Mar. 2003, 1-7.
Kalant H. et al., Death in Amphetamine Users: Caues and Rates, CMA Journal, vol. 112 (Feb. 8, 1975): 299-304.
Katz N. et al. "Challenges in the development of prescription opioid abuse-deterrent formulations", Clin. J. Pain, 23(8): 648-660 (Oct. 2007).

(56) References Cited

OTHER PUBLICATIONS

Kim C.-J. "Drug Release from Compressed Hydrophilic Polyox-WSR Tablets" J Pharm. Sciences 1995, 84(3): pp. 303-306.
Kim N et al. "Preparation and Evaluation of Eudragit Gels. V. Rectal Gel Preparations for Sustained Release and Avoidance of First-Pass Metabolism of Lidocaine", Chem. Pharm Bull. 1992, 40(10), 2800-2804.
King et al. Oral Solid Dosage Forms. Chapter 90. pp. 163-1632 In Remington's Pharmaceutical Sciences, 17th Ed, 1985.
King, R, "Tablets, Capsules, and Pills" Remington's Pharmaceutical Sciences, pp. 1553-1593, Ch. 89, 1980, 16th Edition.
King, Remington's Pharmaceutical Sciences 17th ed., Chapter 78, p. 1418 (1985).
Knevel, Adelbert. Separation. Chapter 78. pp. 1432-1442 in Remington's Pharmaceutical Sciences, 17th Ed, 1985.
Kolter, K., "Compression Behaviour of Kollidon SR," APV/ APGI 2002, Florence, Apr. 11, 2002.
Kondrat, T. , "Technology dosage forms" Moscow 1991, p. 96.
Lee, Y.-S. et al., Principles of Terahertz Science and Technology (Lecture Notes in Physics), Springer; 1 edition 2008. (Table of Contents Only).
Lenindzer, A., "The molecular basis of the structure and functions of cells" Moscow 1974, p. 68.
Levina et al., "The Effect of Ultrasonic Vibration on the Compaction Characteristics of Ibuprofen" Drug Development and Industrial Pharmacy, vol. 28, No. 5, pp. 495-514, 2002.
Levina M. et al "The Effect of Ultrasonic Vibration on the Compaction Characteristics of Paracetamol", Journal of Pharmaceutical Sciences, vol. 89, No. 6, pp. 705-723, Jun. 2000.
Li et al, "Characterization of Poly(Ethylene Oxide) as a Drug Carrier in Hot-Melt Extrusion", Drug Development and Industrial Pharmacy, vol. 32, No. 8, Jan. 1, 2006, pp. 991-1002.
Lieberman, Herbert A., Pharmaceutical Dosage Forms, Tablets, Second Edition, Revised and Expanded, 1990. vol. 2 (Cover and Table of Content only).
Lintner, Carl. Stability of Pharmaceutical Products. Chapter 82. pp. 1478-1486 in Remington's Pharmaceutical Sciences, 17th Ed, 1985.
Liu J. et al., "Properties of Lipophilic Matrix Tables Containing Phenylpropanolamine Hydrochloride Prepared by Hot-Melt Extrusion", EJPB, 52 (2001), pp. 181-190.
Lockhart H. et al, "Packaging of Pharmaceuticals and Health Care Products"; Blackie Academic & Professional; First Edition 1996. (Table of contents only).
Longer et al. Sustained-Release Drug Delivery Systems. Chapter 92. pp. 1611-1661 in Remington's Pharmaceutical Sciences, 17th Ed, 1985.
Madorsky S.L. "Thermal degradation of Polyethylene Oxide and Polypropylene Oxide", Journal of Polymer Science, pp. 183-194 vol. 36, No. 3, Mar. 1959.
Maggi et al., "Dissolution behavior of hydrophilic matrix tablets containing two different polyethylene oxides (PEOs) for the controlled release of a water-soluble drug. Dimensionality study" Biomaterials, 2002, 23, 1113-1119.
Maggi L.et al, "High molecular weight polyethylene oxides (PEOs) as an alternative to HPMC in controlled release dosage form", 2000, International Journal of Pharmaceutics, 195 pp. 229-238.
Maggi, C.. Therapeutic Potential of Capsaicin-like Molecules. Life Sciences, vol. 51, pp. 1777-1781, 1992.
Mank R. et al., "Darstellung wirkstoffhaltiger Extrusionsformlinge auf der Basis von Thermoplasten. Teil 1: Untersuchung zur Wirkstoffliberation" Pharmazie 44, H. 11, pp. 773-776, 1989. English language translation of relevant paragraph provided.
Mank R., "Darstellung wirkstoffhaltiger Extrusionsformlinge auf der Basis von Thermoplasten. Teil 2: Unersuchungen zur Optimierung der Wirkstofffreigabe" Pharmazie 45, H. 8, pp. 592-593 1990. English language translation of relevant paragraph provided.
Marques, Tablet breaking force, 2008.
Matos, Dr. Rick, Ph.D—Letter Jan. 6, 2011.
Mcgary, C.W.. Jr. "Degradation of Poly(ethylene Oxide)", Journal of Polymer Science vol. XLVI, 1960, pp. 51-57.

Mcginity et al., Hot-Melt Extrusion as a Pharmaceutical Process, American Pharmaceutical Review, vol. 4 (2), pp. 25-36, 2001.
Mcginity, J.W.—Letter of Jan. 26, 2009, pp. 1-4.
Mcneill M. et al. Properties controlling the diffusion and release of water-soluble solutes from poly(ethylene oxide) hydrogels. 4. Extended constant rate release from partly-coated spheres. Journal Biomat. Sci. Polymer. Ed. 1996, vol. 7, pp. 953-63.
Mesiha M.S. et al "A Screening Study of Lubricants in Wet Powder Passes Suitable for extrusio-spheronization", Drug Development and Industrial Pharmacy, 19(8), pp. 943-959, 1993.
Metformin Hydrochloride 1000 mg Extended Release Tablets, Lubrizol Advanced Materials, Inc., Nov. 20, 2009, Previous Edition Dec. 19, 2008.
Metformin Hydrochloride 750 mg Extended Release Tablets, Lubrizol Advanced Materials, Inc., Sep. 2010.
Miles, R.E. et al., Terahertz Frequency Detection and Identification of Materials and Objects (NATO Science for Peace and Security Series B: Physics and Biophysics), Springer; 1 edition 2007. (Table of contents).
Miller "To crush or not to crush? What to consider before giving medications to a patent with a tube or who has trouble swallowing", Nursing, pp. 50-52, Feb. 2000.
Mises à jour cumulatives, Vidal, Jan./Oct. 2002 (full translation attached).
Mitchell, "Oral Dosage Forms That Should Not Be Crushed: 2000 Update" Hospital Pharmacy 35(5), 553-557, 2000.
Monolithic: retrieved from internet: http:/merriam-webster.com/dictionary/monolithic. Retrieved on Sep. 2, 2015.
Moorman-Li, R. et al, "A Review of Abuse-Deterrent Opioids for Chronic Nonmalignant Pain." Pharmacy and Therapeutics, vol. 37 No. 7, Jul. 2012, pp. 412-421.
Morissette et al. Advanced Drug Delivery Review 26 (2004), 275-300.
Moroni A. et al, "Application of Poly(Oxyethylene) Homopolymers in Sustained release Solid formulations" Drug Development and Industrial Pharmacy, 21(12) pp. 1411-1428, 1995.
Mullins, John. Ophthalmic Preparations. Chapter 87. pp. 1553-1563; in Remington's Pharmaceutical Sciences, 17th Ed, 1985.
Munjal M. et al., "Polymeric Systems for Amorphous Delta9—Tetrahydrocannabinol Produced by a Hot-Melt Method. Part II: Effect of Oxidation Mechanisms and Chemical Interactions on Stability" Journal of Pharmaceutical Sciences vol. 95 No. 11, Wiley InterScience, 2006, pp. 2473-2485.
Munsell Color Company, "The Munsell Book of Color: Glossy Collection", X-Rite, Originally published in 1966, pp. 1-7.
Nairn, J.G., Solutions, Emulsion, Suspensions and Extractives. Chapter 84. pp. 1492-1517, in Remington's Pharmaceutical Sciences, 17th Ed, 1985.
Note for Guidance on Stability Testing, EMEA, Aug. 2003, pp. 1-20.
Note for Guidance on the Investigation of Bioavailability and Bioequivalence, EMEA, London, Jul. 26, 2001 (CPMP/EWP/QWP/1401/98).
Ohnishi N. et al., Effect of the Molecular Weight of Polyethylene Glycol on the Bioavailability of Indomethacin Sustained-Release suppoositories Prepared with Solid Dispersion, Chem. Pharm. Bull, 35(8), pp. 3511-3515, 1987.
Oliveira et al., "Production and characterization of laminar coextrudates at room temperature in the absence of solvents," AAPS Annual Meeting and Exposition, Oct. 14-18, 2012, Chicago, USA.
Oxicotin: Balancing Risks and Benefits, United States Senate, Hearing, Feb. 12, 2002.
Oxycodon (Oxygesic): Missbrauch, Abhaengigkeit und toedliche Folgen durch Injection zerstossener Retardtabletten, Deutsches Ärzteblatt, vol. 36, A2326-A2326, Sep. 5, 2003.
Ozeki T. et al. "Control of Medicine Release From Solid Dispersion Through Poly(ethylene oxide)-Carboxyvinylpolymer Interaction", International Journal of Pharmaceutics, 165, 1998, pp. 239-244.
Ozeki T. et al. "Controlled Release From Solid Dispersion Composed of Poly(ethylene oxide)-Carbopol Interpolymer Complex With Various Cross-Linking Degrees of Carbopol", Journal of Controlled Release. 63, 2000. pp. 287-295.

(56) References Cited

OTHER PUBLICATIONS

Ozeki T. et al., "Control of medicine release from solid dispersion composed of the poly(ethylene oxide)-carboxyviylpolymer interpolymer complex by varying molecular wight of poly(ethylene oxide)" Journal of Controlled Release 58, pp. 87-95, 1999.
PCT International Search Report and Written Opinion for PCT Application No. PCT/EP2010/004459 dated Dec. 1, 2010.
PCT International Search Report and Written Opinion for PCT Application No. PCT/EP2009/003290 dated Jul. 9, 2009.
PCT International Search Report and Written Opinion for PCT Application No. PCT/EP2013/053894 dated Mar. 22, 2013.
PCT International Search Report and Written Opinion for PCT Application No. PCT/EP2013/057851 dated Jun. 12, 2013.
PCT International Search Report and Written Opinion for PCT Application No. PCT/EP2013/059728 dated Aug. 6, 2013.
PCT International Search Report and Written Opinion for PCT Application No. PCT/EP2014/064830 dated Aug. 6, 2014.
PCT International Search Report and Written Opinion for PCT Application No. PCT/EP2014/075618 dated Feb. 11, 2015.
PCT International Search Report and Written Opinion for PCT Application No. PCT/EP2014/0777748 dated Feb. 12, 2015.
PCT International Search Report and Written Opinion for PCT Application No. PCT/EP2015/060377 dated Jul. 23, 2015.
PCT International Search Report and Written Opinion for PCT Application No. PCT/EP2015/061343 dated Jul. 21, 2015.
PCT Second Written Opinion for PCT Application No. PCT/EP2013/053893 dated Feb. 21, 2014.
PCT Second Written Opinion for PCT Application No. PCT/EP2013/057851 dated Apr. 15, 2014.
Pentoxifylline 400 mg Extended Release Tablets, Lubrizol Advanced Materials, Inc., Mar. 3, 2011, Previous Edition Nov. 19, 2009.
Perez-Marcos, B., Usefulness of certain varieties of Carbomer in the formulation of hydrophilic furosemide matrices, International Journal of Pharmaceutics, 67 (1991) 113-121.
Pharm. Research, Official Journal of the American Association of Pharmaceutical Scientists, Sep. 1989, 6(9), S-98.
Pharm. Research, Official Journal of the American Association of Pharmaceutical Scientists, Oct. 1991, 8(10), S-192.
Phillips, G. Briggs. Sterilization. Chapter 79. pp. 1443-1454, In Remington's Pharmaceutical Sciences, 17th Ed, 1985.
Physico-mechanical Characterization of Polyox for Table Manufacture, Colorcon Jul. 2009.
Pillay V. et al. A novel approach for constant rate delivery of highly soluble bioactives from a simple monolithic system, Journal of Controlled Release. 2000, vol. 67, pp. 67-78.
Pinto, Joao F. et al.,"Evaluation of the Potential Use of Poly(ethylene oxide) as Tablet- and Extrudate-Forming Material," AAPS PharmSci, 2004; 6 (2), Article 15, pp. 1-10, (http://www.aapspharmsci.org).
Piringer, O.G.and A.L. Baner, Plastic Packaging: Interactions with Food and Pharmaceuticals, Wiley VCH, 2nd Completely Revised Edition, Feb. 13, 2008. (Table of Contents only).
Polyox water soluble resins 2003. http://www.dow.com/webapps/lit/litorder.asp?filepath=polyox/pdfs/noreg/326-00002.pdf.
POLYOX water-soluble resins (DOW Mar. 2002); see http://msdssearch.dow.com/PublishedLiteratureDOWCOM/dh_0031/0901b8038003 1a4a.pdf?filepath=/326-00001.pdf&fromPage=GetDoc).
POLYOX WSR-303, retrieved Mar. 10, 2014 from URL http://www.dow.com/dowwolff/en/industrial_solutions/polymers/polyethylene.
POLYOX, COLORCON, Application Data (Apr. 2009) downloaded from http://www.colorcon.com/literature/marketing/mr/Extended%20Release/POLYOX/English/ads_PEO_Antioxidant.pdf.
Pontier, C. et al, "Use of cycles of compression to characterize the behavior of apatitic phosphate powders," Journal of the European Ceramic Society 22 (2002), 1205-1216.
Porter, S. Coating of Pharmaceutical Dosage Forms. Chapter 91. pp. 1633-1643 In Remington's Pharmaceutical Sciences, 17th Ed, 1985.

Prapaitrakul W. et al, "Release of Chlorpheniramine Maleate from Fatty Acid Ester Matrix disks Prepared by Melt-extrusion" J. Pharm. Pharmacol. 43, pp. 377-381, 1991.
Proeschel, P.A. et al., "Task-dependence of activity / bite-force Relations and its impact on estimation of chewing force from EMG"; J. Dent. Res., vol. 81, No. 7, pp. 464-468, 2002.
Purdue News, "Purdue Pharma Provides Update on Development of New Abuse-Resistant Pain Medications; FDA Cites Patient Needs As First Priority; New Drug Application Delayed," www.headaches.about.com, Jun. 18, 2002, pp. 1-6.
Quintavalle et al., "Preparation of sustained release co-extrudates by hot-melt extrusion and mathematical modelling of in vitro/in vivo drug release profiles," European Journal of Pharmaceutical Sciences 33 (2008), 282-293.
Radko S.et al., Applied ad Theoretical Electrophoresis 5, pp. 79-88, 1995.
Ravin, L. Preformulation. Chapter 76, pp. 1409-1423, In Remington's Pharmaceutical Sciences, 17th Ed, 1985.
Remington, The Science and Practice of Pharmacy, 19th ed., vol. II, p. 1457 (1995) (providing a table of DFA-approved commercially marketed salts).
Repka M. et al., Bioadhesive Properties of Hydroxypropylcellulose Topical Films Produced by Hot-Melt Extrusion, Journal of Controlled Release, 70 (2001), pp. 341-351.
Repka MA, Drug Dev Ind Pharm. Oct. 2007; 33(10):1043. (Abstract).
Riippi M. et al., The effect of compression force on surface structure, crushing strength, friability and disintegration time of erythromycin acistrate tablets, Eur J Pharm Biopharm, vol. 46, 1998, pp. 339-345.
Rippie E.G. et al, "Regulation of Dissolution Rate by Pellet Geometry" Journal of Pharmaceutical Sciences, Vo. 58, No. 4, pp. 428-431, Apr. 1969.
Rippie, E. Powders. Chapter 89, pp. 1585-1602, In Remington's Pharmaceutical Sciences, 17th Ed, 1985.
Ritschel et al. Die Tablette: Handbuch der Entwicklung, Herstellung und Qualitatssicherung. 2nd Edition, 2002, Ch 6, pp. 515-519. (Full English translation attached).
Ritschel et al. Die Tablette: Handbuch der Entwicklung, Herstellung und Qualitatssicherung. 2nd Edition, 2002, Ch 6, pp. 69-82 and 115-136.
Ritschel et al. Die Tablette: Handbuch der Entwicklung, Herstellung und Qualitatssicherung. 2nd Edition, 2002, Table of content.
Rosiaux et al. "Ethanol-resistant ethylcellulose/guar gum coatings—Importance for formulation parameters" European Journal of Pharmaceutics and Biopharmaceutics, vol. 85, N0. 3, (Jul. 25, 2013). pp. 1250-1258.
Rowe C et al. Handbook of Pharmaceutical Excipients. Sixth Edition. 2009, Edition Cantor Verlag Aulendorf, pp. V-IX, Table of Contents.
Rowe C et al., Handbook of Pharmaceutical Excipients, 7th Edition, 2012, Table of Contents.
Saleem et al. "Formulation and Evaluation of Tramadol hydrochloride Rectal Suppositories," Indian J. Pharm Sci. Sep.-Oct. 2008; 70(5), 640-644.
Salomies et al., "Determination of Oxycodone Hydrochloride in Oral Solutions by High-Performance Thin-Layer Chromatography/Densitometry," Journal of AOAC International, 83: 1497-1501 (2000).
Satish et al. "Formulation and Characterization of Matrix and Triple Layer Matrix Tablets for Controlled Delivery of Tramadol Hydrochloride," International Journal of Pharmaceutical Sciences; 5(4) (2013) 458-464.
Sax et al., Hawley's Condensed Chemical Dictionary, 11th ed., 1987, p. 1233, definition of "wax".
Scheirs J., et al."Characterizing the Solid-State Thermal Oxidation of Poly (ethylene oxide) Powder", pp. 2014-2019, Polymer, vol. 32, No. 11, 1991.
Schier et al. "Fatality from Administration of Labetalol and Crushed Extended-Release Nifedipine" The Annals of Pharmacotherapy vol. 37, 1420-1423, Oct. 2003.
Schroeder J., et al. Granulierung hydrophober Wirkstoffe im Planetwalzenextruder, Pharm. Ind. 2003, vol. 65, No. 4, 367-372. (Full English translation attached).

(56) References Cited

OTHER PUBLICATIONS

Sciarra et al. Aerosols. Chapter 93., pp. 1662-1677, In Remington's Pharmaceutical Sciences, 17th Ed, 1985.
Search result conducted on http://www.unitconversion.org/force/newtons-to-kiloponds-convresion.html, on Jul. 5, 2011 (Conversion of 18.8 kiloponds to newtons).
Shivanand P et al., "Factors Affecting Release of KCI From Melt extruded Polyethylene Disks", Pharmaceutical Research, Oct. 1991, vol. 8, No. 10, p. S-192.
Sidhu et al., "Watch for nonpsychotropics causing psychiatric side effects," Current Psychiatry, vol. 7, No. 4, 2008, 61-74.
Siegel, P. Tonicity, Osmoticity, Osmolality, and Osmolarity. Chapter 80. pp. 1454-1472 in Remington's Pharmaceutical Sciences, 17th Ed, 1985.
Silver, J. "Painkiller OxyContin most commonly abused prescription drug on the streets of Western Pennsylvania", Pittsburg Post-Gazette, Apr. 8, 2001.
Spassov et al., Stereochemistry of Diastereomeric 3-Dialkylaminopropanols and O-Derivatives, J.f. prakt. Chemie, 323:5, 793-800 (1981).
Sprockel O.L et al. "Permeability of Cellulose Polymers: Water Vapour Transmission Rates"., J. Pharma. Pharmacol. 42, pp. 152-157, 1990.
Sreenivasa, B. et al, Design and Evaluation of Ethylene Vinyl Acetate Sintered Matrix Tablets, Indian Journal of Pharmaceutical Sciences, Sep.-Oct. 2003, 65(5): 496-502.
Stafford J., überzogene feste Formen, 1991, 347-68. (English translation attached).
Strang, Abuse of buprenorphie (Temgesic) by snorting, Letter to the editor, British Med. J., 302: 969 (1991).
Stringer J.L., et al "Diffusion of small molecular weight drugs in radiation-crosslinked poly(ethylene oxide) hydrogels", Journal of Controlled Release 42, pp. 195-202, 1996.
Summers et al; "Influence of Crystal Form on Tensile Strength of Compacts of Pharmaceutical Materials" Journal of Pharmaceutical Sciences, vol. 66, No. 8, Aug. 1977, pp. 1172-1175.
Swarbrick, Encyclopedia of Pharmaceutical Technology, Informa Healthcare, 1988, 1st edition, vol. 1, table of contents.
Swarbrick, Encyclopedia of Pharmaceutical Technology, Informa Healthcare, 1988, 1st edition, vol. 10, table of contents.
Swarbrick, Encyclopedia of Pharmaceutical Technology, Informa Healthcare, 1988, 1st edition, vol. 11, table of contents.
Swarbrick, Encyclopedia of Pharmaceutical Technology, Informa Healthcare, 1988, 1st edition, vol. 12, table of contents.
Swarbrick, Encyclopedia of Pharmaceutical Technology, Informa Healthcare, 1988, 1st edition, vol. 13, table of contents.
Swarbrick, Encyclopedia of Pharmaceutical Technology, Informa Healthcare, 1988, 1st edition, vol. 14, table of contents.
Swarbrick, Encyclopedia of Pharmaceutical Technology, Informa Healthcare, 1988, 1st edition, vol. 15, table of contents.
Swarbrick, Encyclopedia of Pharmaceutical Technology, Informa Healthcare, 1988, 1st edition, vol. 16, table of contents.
Swarbrick, Encyclopedia of Pharmaceutical Technology, Informa Healthcare, 1988, 1st edition, vol. 18, table of contents.
Swarbrick, Encyclopedia of Pharmaceutical Technology, Informa Healthcare, 1988, 1st edition, vol. 19, table of contents.
Swarbrick, Encyclopedia of Pharmaceutical Technology, Informa Healthcare, 1988, 1st edition, vol. 2, table of contents.
Swarbrick, Encyclopedia of Pharmaceutical Technology, Informa Healthcare, 1988, 1st edition, vol. 20, table of contents.
Swarbrick, Encyclopedia of Pharmaceutical Technology, Informa Healthcare, 1988, 1st edition, vol. 3, table of contents.
Swarbrick, Encyclopedia of Pharmaceutical Technology, Informa Healthcare, 1988, 1st edition, vol. 4, table of contents.
Swarbrick, Encyclopedia of Pharmaceutical Technology, Informa Healthcare, 1988, 1st edition, vol. 5, table of contents.
Swarbrick, Encyclopedia of Pharmaceutical Technology, Informa Healthcare, 1988, 1st edition, vol. 6, table of contents.
Swarbrick, Encyclopedia of Pharmaceutical Technology, Informa Healthcare, 1988, 1st edition, vol. 7, table of contents.
Swarbrick, Encyclopedia of Pharmaceutical Technology, Informa Healthcare, 1988, 1st edition, vol. 8, table of contents.
Swarbrick, Encyclopedia of Pharmaceutical Technology, Informa Healthcare, 1988, 1st edition, vol. 9, table of contents.
Tablet, www.docstoc.com (2011).
Tennant, "Simultaneous Use of Stimulants and Opioids," 2011 [online] retrieved on Jul. 7, 2016 from: http://www.practicalpainmanagement.com/treatments/pharmacological/opioids/simultaneous-use-stimulants-opioids; 7 pages.
The Merck Index, 14th Ed. (2006) No. 0006360 Nalefene.
The Merck Index, 14th Ed. (2006) No. 0006362 Naloxone.
The Merck Index, 14th Ed. (2006) No. 0006363 Naltrexone.
The Merck Index, 14th Ed. (2006) No. 0006959 Oxycodone.
Third Party Observations filed with EPO for Patent EP658055B1, Feb. 2, 2009, pp. 1-8.
Thoma V.K. et al. "Bestimmung der In-vitro-Freigabe von schwach basischen Wirkstoffen aus Ratardarzneiformen", pp. 299-301, Pharm. Ind. 51, Nr. 3, 1989.
Tikhonov, A. et al, Biopharmacy. The Manual for Students of Pharmaceutical Universities and Departments, 2003, pp. 40-41, Kharkov, Ukraine (Full English translation attached).
Tipler, et al, Physics for Scientists and Engineers, vol. I, 6th Edition, pp. 234-235, 2003.
Tompkins et al., "Human abuse liability assessment of oxycodone combined with ultra-low-dose natrexone," Psychopharma., 210: 471-480 (2010).
Tramadol Hydrochloride 100 mg Extended Release Tablets, Lubrizol Advanced Materials, Inc., Sep. 2010.
Tranquilan-Aranilla et al., "Kappa-carrageenan-polyethylene oxide hydrogel blends prepared by gamma irradiation," Radiation Physics and Chemistry vol. 55, pp. 127-131, 1999.
Turco et al. Intravenous Admixtures. Chapter 86. pp. 1542-1552, In Remington's Pharmaceutical Sciences, 17th Ed, 1985.
US Pharmacopoeia, Chapter 1217, Aug. 12, 2008.
Varma et al, Factors Affecting Mechanism and Kinetics of Drug Release from Matrix-Based Oral Controlled Drug Delivery Systems, Am. J. Drug Deliv. 2004: 2 (1): 43-57.
Verhoeven et al., "Influence of polyethylene glycol/polyethylene oxide on the release characteristics of sustained-release ethylcellulose mini-matrices produced by hot-melt extrusion: in vitro and in vivo evaluations," European Journal of Pharmaceutics and Biopharmaceutics 72 (2009) 463-470.
Verhoeven, et al. "Xanthan gum to tailor drug release of sustained-release ethylcellulose mini-matrices prepared via hotmelt extrusion: in vitro and in vivo evaluation," European Journal of Pharmaceutics and Biopharmaceutics, 63 (2006) 320-330.
Vippagunta et al. Crystalline Solids, Advanced Drug Delivery Review 48 (2001), 3-26.
Vynckier et al.,"Hot-melt co-extrusion for the production of fixed-dose combination products with a controlled release ethylcellulose matrix core," International Journal of Pharmaceutics 464 (2014), 65-74.
Wade and Weller, "Handbook of Pharmaceutical Excipients: 2nd Edition", The American Pharmaceutical Association and The Pharmaceutical Press, Washington and London, Table of Contents pp. v-vi, 1994.
Wagner, Pharmazeutische Biologie—Drogen und ihre Inhaltsstoffe—Scharfstoffdrogen, 2nd., revised edition, Gustav Fischer Verlag, Stuttgart—N.Y., 1982, pp. 82-92 (Full English Translation attached).
Wagner, Pharmazeutische Biologie—Drogen und ihre Inhaltsstoffe—Scharfstoffdrogen, 2nd., revised edition, Gustav Fischer Verlag, Stuttgart—N.Y., 1982,Table of Content.
Waltimo, et al, "A novel bite force recorder and maximal isometric bite force values for healthy young adults", Scandinavian Journal of Dental Research 1993; 101: 171-175.
Waltimo, et al, "Maximal bite force and its association with signs and symptoms of craniomandibular disorders in young Finnish non-patients", Acta Odontol Scand 53 (1995): 254-258.
Waterman et al., "Stabilization of Pharmaceuticals to Oxidative Degradation", Pharmaceutical Development and Technology, vol. 7(1), pp. 1-32, (2002).
Waters et al., "Intravenous Quetiapine-Cocaine Use ("Q-Ball")", Letter to the Editor, Am. J. Psychiatry, 164(1): pp. 173-174 (2007).

(56) References Cited

OTHER PUBLICATIONS

Weiss, U., "Derivatives of Morphine. I 14-Dihydroxydihydromorphinone," J. Am. Chem. Soc. 77, pp. 5891-5892, Nov. 20, 1955.

West, Anthony R., Solid state chemistry and its applications, Wiley, New York, 1988, pp. 358 and 365.

Wikipedia—Dextromethorphan Aug. 12, 2013 (and attached related English-language entry dated Dec. 11, 2013).

Woodburn, K.R. et al., Vascular complications of injecting drug misuse, Br. J. of Surgery, vol. 83, 1996, pp. 1329-1334.

Wu N, et al. Mathematical modeling and in vitro study of controlled drug release via a highly swellable and dissoluble polymer matrix: polyethylene oxide with high molecular weights, J Control Release. Feb. 16, 2005;102(3):569-581.

Yang et al., "Zero-Order Release Kinetics from a Self-Correcting Floatable Asymmetric Configuration Drug Delivery System", Journal of Pharmaceutical Sciences, vol. 85, No. 2, Feb. 1996, pp. 170-173.

Yang, et al; "Characterization of Compressibility and Compactibility of Poly(ethylene oxide) Polymers for Modified Release Application by Compaction Simulator"; Journal of Pharmaceutical Sciences, vol. 85, No. 10, pp. 1085-1090, Oct. 1996.

Yarbrough et al, Letters to Nature "Extraordinary effects of mortar-and-pestle grinding on microstructure of sintered alumina gel", Nature 322, pp. 347-349 (Abstract only) (Jul. 24, 1986).

Yeh et al., Stability of Morphine in Aqueous Solution III: Kinetics of Morphine Degradation in Aqueous Solution, Wiley Subscription Services, Inc., Journal of Pharmaceutical Sciences, 50(1): 35-42 (1961).

Zeeshan, F and N. Bukhari, "Development and Evaluation of a Novel Modified-Release Pellet-Based Tablet System for the Delivery of Loratadine and Pseudophedrine Hydrochloride as Model Drugs," AAPS PharmSciTech 11(2); 910-916 (available on-line May 22, 2010).

Zhang et al., "Properties of Sustained-Release Tablets Prepared by Hot-Melt Extrusion" Pharmaceutical Development and Technology, 1999, 4(2), 241-250.

Targin(R) Product Monograph. Purdue Pharma. Revised Mar. 1, 2016.

Baxter, J.L. et al., "Hydrodynamics-induced variability in the USP apparatus II dissolution test," International Journal of Pharmaceutics 292 (2005) 17-28.

Bellmann et al., "Development of an advanced in vitro model of the stomach and its evaluation versus human gastric psychology." Food Research International 88 (2016) 191-198.

Koziolek, M. et al., "Development of a bio-relevant dissolution test device simulating mechanical aspects present in the fed stomach," European Journal of Pharmaceutical Sciences 57 (2014) 250-256.

Remington, Chapter 45, pp. 996-1035. (Full Translation Attached).

De Brabander C., et al., "Development and evaluation of sustained release mini-matrices prepared via hot melt extrusion," Journal of Controlled Release 89 (2003), 235-247.

Sumitomo Seika Chemicals, Co., Ltd, "Certificate of Analysis," Product: Polyethylene Oxide; Grade: PEO-18NF; Feb. 2, 2016.

Sumitomo Seika Chemicals, Co., Ltd, "Certificate of Analysis," Product: Polyethylene Oxide; Grade: PEO-20NF; Feb. 3, 2016.

Sumitomo Seika Chemicals, Co., Ltd, "Certificate of Analysis," Product: Polyethylene Oxide; Grade: PEO-20NF; Jan. 23, 2012.

Sumitomo Seika Chemicals, Co., Ltd, "Certificate of Analysis," Product: Polyethylene Oxide; Grade: PEO-20NF; May 15, 2013.

Pharma Tips ([online] retrieved on Mar. 22, 2018 from http://ww.pharmatips.in/Articles/Pharmaceutics/Tablet/Co-Processed-Directly-Compressed-Adjutants.aspx May 2011: 10 pages).

Agarwal, G, et al, "Oral Sustained Release Tablets: An Overview with a Special Emphasis on Matrix Tablet," American Journal of Advanced Drug Delivery, 2017.

Brzeclo, W.,et al., "The Advent of a new Pseudoephedrine Product to Combat Methampetamine Abuse," Am J Drug Alcohol Abuse, 2013: 39(5): 284-290.

Extended European Search Report for Application No. 17173240.7 dated Nov. 28, 2017.

Jamini, M., et al, "Sustained Release Matrix Type Drug Delivery System: A Review," Journal of Drug Delivery & Therapeutics; 2012, 2(6), 142-148.

Kelly, C. et al, "Methamphetamine Synthesis Inhibition: Dissolving Metal Reductions," Johns Hopkins Univ. Applied Physics Lab., 2015, 1-10.

"Low Substituted Hydroxypropyl Celluslose", Drugs.com, from https://www.drugs.com/inactive/low-susbstitute-hydroxypropyl-cellulose-581.html (2018).

Misal, R, et al., "Matrix Tablet: A Promising Technique for Controlled Drug Delivery," Indo American Journal of Pharmaceutical Research, 2013.

Patrick, K., et al., "Pharmacology of Methylphenidate, Amphetamine Enantiomers and Pemoline in Attention-Deficit Hyperactivity Disorder,"Human Psychopharmacology, vol. 12, 527-546 (199).

Presley, B. et al., "Efficiency of Extraction and Conversion of Pseudoephedrine to Methamphetamine from Tamper-Resistant and Non-Tamper-Resistant Formulations," Journal of Pharmaceutical and Biomedical Analysis, 2018, 16-22.

Qi et al, "An Investigation into the Crystallisation Behavior of an Amorphous Cryomilled Pharmaceutical Material Above and Below the Glass Transition Temperature," Journal of Pharmaceutical Sciences, 2009, 196-208.

Houston, T.E., et al., "Bite Force and Bite Pressure: Comparison of Humans and Dogs," http://www.glapbta.com/BFBP.pdf, 2003, pp. 1-7.

Sigma-Aldrich entry for CAS No. 9010-88-2; www.sigmaaldrich.com/catalog/product/aldrich/182249?lang=en&region=US (downloaded Jun. 2018).

U.S. Appl. No. 60/287,509, filed Dec. 2, 2002, Joshi et al.
U.S. Appl. No. 60/288,211, filed Sep. 2, 2004, Oshlack et al.
U.S. Appl. No. 60/310,514, filed Apr. 3, 2003, Oshlack et al.
U.S. Appl. No. 60/310,534, filed Apr. 10, 2003, Wright et al.
U.S. Appl. No. 60/376,470, filed Jan. 15, 2004, Ayer et al.
U.S. Appl. No. 60/384,442, filed Dec. 4, 2003, Fink et al.

European Pharmacopoeia 3.0, 2.9.8 "Resistance to Crushing of Tablets", 1997, p. 135.

Goodman and Gilman, 1985, 7th edition, chapter 29, 674-715.

King, Remington's Pharmaceutical Sciences 17th ed., Chapter 78, p. 1418-1419 (1985).

Ouadros, E. et al., "Evaluation of a novel colonic delivery device in vivo," STP Pharma Sci. 5, 77-82 (1995).

Theeuwes, Felix et al., Osmotic Systems for Colon-Targeted Drug Delivery in Colonic Drug Absorption and Metabolism (Peter R. Bieck ed., 1993).

Wooten, Marvin R. et al., Intracerebral Hemorrhage and Vasculitis Related to Ephedrine Abuse, 13 Annals of Neurology 337 (1983).

Patel, Et. Al., "Poloxamers: A pharmaceutical excipient with therapeutic behaviors," PharmTech, vol. 1, No. 2, pp. 299-300 (Apr. 2009).

M. Xu et al., "Evaluation of the coat quality of sustained release pellets by individual pellet dissolution methodology," Int. J. Pharm. 478 (2015) 318-327.

Linz et al. "Cebranopadol: A Novel Potent Analgesic Nociception/ Orphanin FQ Peptide and Opioid Receptor Agonist," J Pharmacol. Exp. Ther. 2014; 349: 535-548; available online Apr. 8, 2014.

Sprockel, et. al, "A melt-extrusion process for manufacturing matrix drug delivery systems," Int. Journal of Pharmaceutics 155 (1997) 191-199.

Vezin, W. et al, "Adjustment of precompression force to reduce mixing-time dependence of tablet tensile strength," J. Pharm. Pharmacol. 1983, 35: 555-558 (Mar. 28, 1983).

Weinhold, et al. "Buprenorphine alnoe and in combination with naxolone in non-dependent humans." Drug & Alcohol Dependence 30.3 (1992): 263-274.

Extended European Search Report for Application No. EP 16182124.4-1455, dated Jan. 17, 2017.

Extended European Search Report for Application No. EP 16183922.0-1460, dated Oct. 31, 2016.

(56) References Cited

OTHER PUBLICATIONS

Fathima, N. et al. "Drug-excipient interaction and its importance in dosage form development," Journal of Applied Pharmaceutical Science 01 (06); 2011, pp. 66-71.
Meyer et al., "Awareness Topic: Mitigating the Risks of Ethanol Induced Dose Dumping from Oral Sustained/Controlled Release Dosage Forms," FDA ACPS Meeting, Oct. 2005, p. 1-4.
Remington, Chapter 45, pp. 996-1035.
Schilling, et al., "Novel application of hot-melt extrusion for the preparation of monolithic matrices containing enteric-coated particles." International Journal of Pharmaceutics 400 (2010) 34-31.
Starch 1500, Partially Pregelatinized Maize Starch, technical data from Colorcon, Feb. 2016, 6 pages.
Nickerson, B., Sample Preparation of Pharmaceutical Dosage Forms, Springer, New York (2011); Chapter 1, pp. 3-48.
PCT International Search Report and Written Opinion for PCT Application No. PCT/EP2016/052046 dated Apr. 12, 2016.
COMPAP 90 technical data sheet Mar. 2014; 1 page.
Furu et al. "use of ADHD drugs in the Nordic countries: a population-based comparison study," Acta Psychiatrica Scandinavia, May 2010.
PCT International Search Report and Written Opinion for PCT Application No. PCT/EP2017/070396 dated Sep. 8, 2017.
Efentakis et al, Effects of Excipients on Swellin and Drug Release from Compressed Matrices, in Drug Development and Industrial Pharmacy 23(1):107-112, Jan. 1997, Abstract.
USP Exert Council, US Pharmacopoeia, Chapter 1092, 2007, 1-15.
Definition Granule, Merriam-Webster, accessed online Jun. 28, 2018 (2018).
Bannwarth, Bernard, "Will Abuse-Deterrent Formulations of Opioid Analgesics be Successful in Achieving Their Purpose?", Drugs, 2012. vol. 72, pp. 1713-1723.
POLYOX Water-Soluble Resins in Pharmaceutical Applications. Dow Chemicals. Published 2004.
Dabbagh, et al. "Release of Propranolol Hydrochloride from Matrix Tablets Containing Sodium Carboxymethylcellulose and Hydroxypropylmethylcellulose"; 1999; Pharmaceutical Development and Technology, 4(3), 313-324.
Turkington, R., "Amphetamines," in Chemicals used for Illegal Purposes. A Guide for first Responders to Identify Explosives, Recreational Drugs, and Poisons, 2010, p. 247.
Decision of the United States District Court for the Southern District of New York, in In re Endo Pharmaceuticals Inc. and Grünenthal GmbH v. Amneal Pharmaceuticals, LLC et al., Findings of Fact and Conclusions of Law, District Judge Thomas P. Griesa, New York, New York, Jan. 14, 2015.
Decision of the United States District Court for the Southern District of New York, in In re Oxycontin Antitrust Litigation, Purdue Pharma LP v. Teva Pharmaceuticals, Findings of Fact and Conclusions of Law, District Judge Sidney H. Stein, New York, New York, Jan. 14, 2014.
U.S. Court of Appeals, Federal Circuit, Purdue Pharma L.P. v. Epic Pharma, LLC, 117 USPQ2d 1733 (Fed. Cir. 2016).
Al-Angari, A. et al. "The compaction properties of polyethylene glycols," J Pharm. Pharmacol. (1985) 37:151-153.
Al-Nasassrah et al. , "The effect of an increase in chain length on the mechanical properties of polyethylene glycols," European Journal of Pharmaceutics and Biopharmaceutics 46 (1998) 31-38.
Anderson, S.L. et al., "A Model for Antiplasticization in Polystyrene," Macromolecules 28:2944-54 (1995).
Back, D.M.et al., "Ethylene Oxide Polymers", in Kirk-Othmer Encyclopedia of Chemical Technology. 2000, John Wiley & Sons, Inc., vol. 10, 673-696.
Bailey, F.E., et al., "High Molecular Weight Polymers of Ethylene Oxide" Solution Properties Industrial and Engineering Chemistry, 1958. 50(1): 8-11.
Balogh, E., "Tastes in and Tastes of Paprika," in Taste: Proceedings of the Oxford Symposium on Food and Cookery 28 (Tom Jaine Ed.) 1988, pp. 25-40.

Baumann, T., "Pain Management," Pharmacotherapy: A Pathophysiologic Approach (J.T. DiPiro et al. eds., McGraw-Hill 4th ed. 1999), Ch. 56, 1014-1026.
Baumrucker, S.J., "OxyContin, the Media, and Law Enforcement", American Journal of Hospice & Palliative Care, 18:3 (May/Jun. 2001), 154-156.
Choi, S., et al., "Development of a Directly Compressible Poly(Ethylene Oxide) Matrix for the Sustained-Release of Dihydrocodeine Bitartrate", Drug Development and Industrial Pharmacy, vol. 29, No. 10, pp. 1045-1052, 2003.
Choi, S., et al., "Hydrophilic Matrix Formulations of Dihydrocodeine Bitartrate with Polyethylene Oxide by Direct Compression," Proceedings of the $29^{th}$ Annual Meeting of the Controlled Release Society, in collaboration with the Korea Society for Biomaterials, Minneapolis, $1^{st}$ Edition, 2002, 984-985.
Ciccone, P. E., "Attempted Abuse of Concerta," Letters to the Editor, J. Am. Acad. Child Adolesc. Psychiatry, 41:7 (Jul. 2002).
Controversies in ADHD: A Breakfast Symposium—Concerta.
Crowley, M. et al., Pharmaceutical Applications of Hot-Melt Extrusion: Part I. Drug Dev. & Indus. Pharmacy (2007) 33:909-926.
Crowley, M. et al., "Properties of Hot-Melt Extruded CPM Tablets Using Hydrophilic Polymers," poster presentation, (2000).
Crowley, M., "Physicochemical and Mechanical Characterization of Hot-Melt Extruded Dosage Forms." Dissertation presented to the Faculty of the Graduate School of The University of Texas at Austin. (May 2003).
Crowley, M., et al., "Evaluation of a Hot Melt Extrusion Technique using a Hydrophilic Thermal Polymer and Retardant for the Preparation of Extended Release Chlorpheniramine Maleate Tablets," in American Association of Pharmaceutical Scientists: Indianapolis, IN (2000).
CROWLEY0000001-CROWLEY0000127.
Davies, N. "Sustained Release and Enteric Coated NSAIDs: Are They Really GI Safe?" J. Pharm. & Pharmaceut. Sci., 2(1):5-14, 1999.
Declaration of Dr. James W. McGinity, dated Oct. 28, 2009; online, retrieved from: http://www.accessdata.fda.gov/dmgsatfda_docs/labeV2013/021121s032lbl.pdf.
Dimitrov, M, et al., "Study of Verapamil hydrochloride release from compressed hydrophilic Polyox-Wsr tablets." Int'l J Pharmaceutics (1999) 189:105-111.
Dittmer, D.K., et al., "Glue-Sniffing Neuropathies," Canadian Family Physician 39:1965-1971 (1993).
Donnelly, C.L., "ADHD Medications: Past and Future," Behavioral Health Management, May/Jun. 2002, 28 & 30.
Dow, "Material Safety Data Sheet: POLYOX(TM) WSR 30" (effective date: Sep. 18, 2001).
Dow, "POLYOX Water-Soluble Resins: Degradation of Water-Soluble Resins," Technical Data (Oct. 2002).
Drug Bank "Oxymorphone," 2015; online, available at: www.dmgbank.ca/chugs/db01192 printed Jul. 1, 2015.
Endo Pharmaceuticals Inc. v. Teva Pharmaceuticals USA, Inc. (S.D.N.Y 2015)—Redacted Version.
FDA News Release, "FDA approves abuse-deterrent labeling for reformulated OxyContin," Apr. 16, 2013, available at http://www.fda.gov/NewsEvents/Newsroom/Press.Announcements/ucm348252.htm.
FDA, "Notice of Determination that OxyContin Drug Products Covered by NDA 20-553 Were Withdrawn From Sale for Reasons of Safety or Effectiveness." Federal Register, vol. 78, No. 75, Apr. 18, 2013, 23273-23274.
Final Draft Labeling for Concerta Extended-Release Tablets Attachment to Approval Letter (2000); available at: http://www.accessdata.fda.gov/drugsatfda_docs/label/2000/21121lbl.pdf.
Greenhill, L.L., et al., "Practice Parameter for the Use of Stimulant Medications in the Treatment of Children, Adolescents, and Adults," J. Am. Acad. Child Adolesc. Psychiatry, 41:2 Supplement, 26S-49S (Feb. 2002).
Griffith, D., "Potential new ADHD drug creating lots of big hopes," Sacramento Bee (California), Oct. 30, 2002.
Huang, H. et al., "Preparation of Controlled Release Oral Dosage Forms by Low Temperature Melt Extrusion," AAPS PharmSci. 2000 2(S1).

(56) References Cited

OTHER PUBLICATIONS

Jaffe, S.L., "Failed Attempts At Intranasal Abuse of Concerta," Letters to the Editor, J. Am. Acad. Child Adolesc. Psychiatry, 41:1 (Jan. 2002).

Jannsen Pharmaceuticals, Inc. Concerta Labeling Revisioins, Dec. 12, 2013; online, retrieved from: http://www.accessdata.fda.gov/dmgsatfda_docs/labeV2013/021121s032lbl.pdf.

Joint Claim Construction and Prehearing Statement, dated Jul. 11, 2014. *Janssen Pharmaceuticals, Inc. and Grünenthal GMBH v. Actavis Elizabeth LLC and Alkem Laboratories Limited*, Civil Action No. 2:13-cv-04507 CCC-MF (D.N.J.), *Janssen Pharmaceuticals, Inc. and Grünenthal GMBH v. Roxane Laboratories, Inc.*, Civil Action No. 2:13-cv-06929 CCC-MF (D.N.J.), and *Janssen Pharmaceuticals, Inc. and Grünenthal GMBH v. Alkem Laboratories Limited*, Civil Action No. 2:13-cv-07803 CCC-MF (D.N.J.).

Kibbe, Coloring Agents, in Handbook of Pharmaceutical Excipients (3d ed. 2000).

Kidokoro, M. et al. ,"Properties of Tablets Containing Granulations of Ibuprofen and Acrylic Copolymers Prepared by Thermal Processes," Pharm Dev. and Tech. , 6:263-275 (2001).

Kinjo, N. et al, "Antiplasticization in the Slightly Plasticized Poly(vinyl chloride)," Polymer Journal 4(2):143-153 (1973).

Larhib, H. et al., "Compressing polyethyelene glycols: the effect of compression pressure and speed," Int 'l J Pharmaceutics (1997) 147: 199-205.

Lieberman, H., et al., Pharmaceutical Dosage Forms: Tablets, vol. 2, Ch. 5: Granulation Technology and Tablet Characterization (1990), Table of contents and 245-348.

Lyons et al., "Twitch Interpolation in the Assessment of the Maximum Force-Generating Capacity of the Jaw-Closing Muscles in Man," Arch. Oral. Biol. 41:12, 1161-1168 (1996).

Makki, A, et. Al., Eds., A Dictionary of American Idioms, 4th Ed. Barron's, New York (2004), 342-343.

Markovitz, H., et al. "Calculations of Entanglement Coupling Spacings in Linear Polymers." Journal of Physical Chemistry, 1962. 66(8): 1567-1568.

Mccrum, N., et al., Principles of Polymer Engineering. 2nd ed., New York: Oxford University Press. 447(1997), Chapter 7, 296-351.

Mcginity, J.W. et al., "Melt-Extruded Controlled-Release Dosage Forms" in Pharmaceutical Extrusion Technology, Ghebre-Sellassie, I. and Martin, C., Eds., Marcel Dekker, Inc., New York, 2003, Chapter 10, 183-208.

Mcquay, H. et a. "Methods of Therapeutic Trials," Textbook of Pain 1125-1138 (P.D. Wall & R. Melzack eds., Elsevier 4th ed. 1999), Table of Contents and 1125-1138.

Miura et al., "Comparison of Maximum Bite Force and Dentate Status Between Healthy and Frail Elderly Persons," J. Oral Rehabilitation, vol. 28 (2001), pp. 592-595.

Miyagawa, Y. et al., "Controlled-release of diclofenac sodium from wax matrix granulate," Int 'l J. Pharmaceutics (1996) 138:215-224.

National Drug Intelligence Center Information Bulletin "OxyContin Diversion and Abuse" Jan. 2001.

Payne, H. et al., Denatonium Benzoate as a Bitter Aversive Additive in Ethylene Glycol and Methanol-Based Automotive Products, SAE Technical Paper 930589, Abstract (1993).

Pilpel, N., et al. "The effect of temperature on the tensile strength and disintegration of paracetamol and oxytetracylcine tablets," J Pharm Pharmac., 29:389-392 (1971).

POLYOX Water-Soluble Resins NF in Pharmaceutical Applications, Dow Chemical Company, Aug. 2002.

Purdue Pharma LP Material Safety Data Sheet, OxyContin Tablets, 10 mg, 15 mg, 20 mg, 30 mg, 40 mg, 60 mg, Version Sep. 16, 2010; available at www.purduephruma.com/msdss/oxycontin_msds.pdf.

Rauwendaal, Chris, Phd, Responsive Expert Report of Chris Rauwendaal, Ph.D. Regarding Expert Report of Michael M. Crowley, Ph.D., dated Jul. 17, 2015.

Repka, M. et al. Pharmaceutical Applications of Hot-Melt Extrusion: Part II. Drug Dev. & Indus. Pharmacy (2007) 33:1043-1057.

Saravanan, M. et al., "The Effect of Tablet Formulation and Hardness on in Vitro Release of Cephalexin from Eudragit L100 Based Extended Release Tablets," Biol. Pharm. Bull. (2002) 25(4):541-545.

Seitz, J.A.; et al., "Evaluation of the Physical Properties of Compressed Tablets 1: Tablet Hardness and Friability," J. of Pharm. Sci. , 54:1353-1357 (1965).

Shah, et al., "Some Effects of Humidity and Heat on the Tableting Properties of Microcrystalline Cellulose Formulations 1," J. of Pharm. Sci., 57:181-182 (1967).

Singhal, et al., Handbook of Indices of Food Quality and Authenticity (1997), "Capsicum" p. 398-299.

Smith, K.L. et al. "High Molecular Weight Polymers of Ethylene Oxide—Plastic Properties." Industrial and Engineering Chemistry, 1958. 50(1): 12-16.

Tapentadol Pre-Review Report, Expert Committee on Drug Dependency Thirty-Fifth Meeting Hammamet, Tunisia, Jun. 4-8, 2012, available at http ://www.who.int/medicines/areas/quality_safety/5.2Tapentadolpre-review.pdf.

Tiwari, D., et al., "Evaluation of polyoxyethylene homopolymers for buccal bioadhesive drug delivery device formulations." AAPS Pharmsci, 1999. 1(3): Article 13.

Wilkins, J.N., "Pharmacotherapy of Schizophrenia Patients with Comorbid Substance Abuse," Schizophrenia Bulletin, 23:215-228 (1997).

World Health Org., Cancer Pain Relief With a Guide to Opioid Availability (2d ed. 1996).

Yin, T.P., et al., "Viscoelastic Properties of Polyethylene Oxide in Rubber-Like State." Journal of Physical Chemistry, 1961. 65(3): 534-538.

Zacny, J. et al. Drug & Alcohol Dependence (2003) 69:215-232.

Zhang, F., "Hot-Melt Extrusion as a Novel Technology to Prepare Sustained-Release Dosage Forms," Dissertation University of Texas at Austin, Dec. 1999.

Claffey et al, "Amphetamine Adducts of Melanin Intermediates Demonstrated by Matrix-Assisted Laser Desorption Ionization Time-of-Flight Mass Spectrometry," Chem. Res. Toxicol. 2001, 14, 1339-1344.

Evans, J.C, et. Al. "Optimal tocopherol concentrations to inhibit soybean oil oxidation,"Journal of The American Oil Chemists' Society 79.1 (2002): 47-511.

Quinn, M.E. "Alpha Tocopherol" in Handbook of Pharmaceuical Excipients, Sixth Edition (2009), 31-33.

"Jet Milling" excerpt downloaded from website Wikipedia.com on May 14, 2019.

Evekeo, (Amphetame Sulfate) for treating patients with ADHD website ([online] https://www.evekeo.com.about-evekeo: 2019:5 pages), 2019.

Lurie et al., "Chiral Resolution of Cationic Drugs of Forensic Interest," (Analytical Chemistry 1994: 66(22): 4019-4026.

Ely et al., "Lithium-Ammonia Reduction of Ephedrine to Methamphetamine: An Unusual Clandestine Synthesis," Technical Note, 1990, 720-723.

European Pharmacopeia, 7th Ed. 2.2.8 and 2.2.10, 27ff. (2010).

Jedinger, N., et al., Eur. J. Pharm, Biopharm 87 (2014), 217-226.

Kunalan et al., "Investigation of the Reaction Impurities Associated with Methylamphetamine Synthesized using the Nagai Method," Anal. Chem. 2012, 84, 5744-52.

Lee et al., "Analysis of the impurities in the metamphetamine synthesized by thee different methods from ephedrine and pseudoephedrine," Forensic Science International 161 (2006). 209-215.

Person et al., Structural Determination of the Principal Byproduct of the Lithium-Ammonia Reduction Method of Methamphetamine Manufacture, J Forensic Sci, Jan. 2005, vol. 50, No. 1, 87-95.

Pintauro, Nicholas, D., Food Flavoring Processes, Table of Content. Park Ridge, NJ and London, UK, 1976.

POLYOX, 2004, online retrieved on Oct. 15, 2018.

Romach et al. "Update on tamper-resistant drug formulations," Drug and Alcohol Dependence, 130 (2013), 13-23.

Salouros et al., Isolation and Identification of Three By-Products Found in Methylamphetamine Synthesized by the Emde Route2010, 605-615.

(56) References Cited

OTHER PUBLICATIONS

Skinner, Harry F., "Methamphetamine Synthesis via Hydriodic Acid/Red Phosphorus Reduction of Ephedrine," Forensic Science International, 48 (1990), 123-134.
BASF the chemical company, Kollicoat IR Technical information, Feb. 2013, p. 1-14 (2013).
Befort et al., "The Conserved Asparatate Residue in the Third Putative Transmember Domain," Molecular Pharmacology 1996: 49:216-223 (1996).
Domino E.F. (1991) Nicotine: A Unique Psychoactive Drug. In: Adlkofer F., Thurau K. (eds.) Effects of Nicotine on Biological Systems. APS Advances in Pharmacological Sciences. Birkhaeuser Basel (1991).
Fitzpatrick, J.; "The influence of Superdisintegrants on Immediate Release," By Pharmaceutical Technology Editions [online] retrieved from http://www.pharmatech.com/influence-superdisintegrants-immediate-release; vol. 21, issue 6 (Jun. 1, 2011).
Kolar et al., "Treatmen of adults with attention-deficit/hyperactivity disorder," Neuropsychiatric Disease and Treatment 2008:4(3):389-403.
Rasmussen, N. "America's First Amphetamine Epidemic 1929-1971," American Journal of Public Health 2008:98(6): 974-985.
Suzuki, T, "Blood-brain barrier transport of opioid analgesics," Abstract, Yakugaki Zasshi; 131(10). 1445-51 (2011).
Gaitondf, B. "General Principles of Drug Action", 1967, p. 48.

\* cited by examiner

PREPARATION OF A POWDERY PHARMACEUTICAL COMPOSITION BY MEANS OF CRYO-MILLING

This application is a continuation of International Patent Application No. PCT/EP2014/075618, filed Nov. 26, 2014, which claims priority of European Patent Application No. 13 425 151.1, filed on Nov. 26, 2013, the entire contents of which patent applications are incorporated herein by reference.

The invention relates to a method for the preparation of a powdery pharmaceutical composition comprising a pharmaceutical excipient, preferably a first pharmaceutical excipient, and a pharmaceutical component, preferably a second pharmaceutical excipient or a pharmacologically active substance, optionally together with a third constituent, preferably another pharmaceutical excipient, wherein the pharmaceutical excipient is a polyalkylene glycol, the method comprising the step of grinding a mixture of the pharmaceutical excipient and the pharmaceutical component at a temperature below ambient temperature. The powdery pharmaceutical composition is particularly useful in the manufacture of pharmaceutical dosage forms comprising at least one pharmacologically active substance. The invention further relates to a method for the manufacture of pharmaceutical dosage forms, such as tablets.

Many pharmaceutical dosage forms require homogeneous distribution of all excipients. Homogeneous distribution of excipients is required in order to maintain product quality, not only with respect to changeless drug content, but also with respect to changeless properties which are based on the presence of specific amounts of excipients such as storage stability, processability, disintegration, release profile, and the like.

Homogeneous distribution of excipients is usually achieved by vigorously mixing the excipients prior to forming the dosage form e.g. by subsequent granulation or direct compression. Blending excipients in a mixer is the method of choice for solid excipients. If one or more excipients are liquid or pasty, however, blending is more difficult to achieve, especially if the compatibility of excipients is limited, e.g. because one excipient is hydrophilic and the other excipient is hydrophobic.

Particular problems arise when the individual amounts of excipients to be mixed with one another substantially differ from one another. For example, it is rather difficult to homogenously distribute small amounts of hydrophobic liquids, e.g. 0.5 wt.-%, in a solid mixture of hydrophilic excipients.

For example, alpha-tocopherol, which is a hydrophobic oily liquid at ambient temperature, is extensively used as antioxidant in pharmaceutical dosage forms. It is known to use alpha-tocopherol as a pre-blend with other pharmaceutical excipients in order to better distribute the comparatively small amount (e.g. 0.1 to 0.2 wt.-%) of alpha-tocopherol in the overall dosage form. Pre-blends of hydrophobic alpha-tocopherol with hydrophilic polyethylene glycol are commercially available. Such products are typically manufactured by spray-congealing. A melt of polyethylene glycol is homogenized with alpha-tocopherol and is sprayed into a drying-tower that is cooled by nitrogen gas and the congealed particles are collected. Spray congealing technology is very laborious and costly.

GB-A 1,147,210 relates to a process for making a dry, free flowing, finely divided, fat-soluble vitamin-active product, comprising (1) preparing a colloidal solution of cold water dispersible, non-gelling colloid material and water; (2) dispersing in said colloidal solution a water insoluble, fat soluble vitamin active composition to form a first dispersion; (3) dispersing the latter in a water immiscible liquid dispersing medium to form a second dispersion; (4) extracting water at −10 to 0° C. from the latter with a water extraction agent until droplets of the first dispersion solidify to form particles; (5) separating the latter from the dispersing medium and water extraction agent at −10 to 0° C.; and (6) removing residual moisture from the solid particles.

U.S. Pat. No. 4,603,143 discloses the preparation of free-flowing and stable vitamin-active powders utilizing special silicon-containing materials which are predominately in the form of substantially discrete agglomerates.

U.S. Pat. No. 4,892,889 relates to a process for making a directly-compressible vitamin powder utilizing a conventional spray-dryer. The resulting powder is comprised of a fat-soluble vitamin, a water-soluble carbohydrate, and a gelatin having a bloom number between 30 and 300.

U.S. Pat. No. 6,183,781 discloses a method for producing an implantable polymer/drug matrix mass, comprising the steps of (1) forming a polymer solution/drug mixture comprising a polymer dissolved in an organic solvent and a suspended labile drug; (2) removing the solvent from the polymer solution/drug mixture, thereby forming a solid polymer/drug matrix; and (3) mechanically compressing the polymer/drug matrix, thereby forming an implantable polymer/drug matrix mass.

U.S. Pat. No. 6,261,599 and US 2004/0081694 disclose sustained release oral opioid analgesic dosage forms comprising a plurality of multiparticulates produced via melt extrusion techniques. The extruded material exits the extruder in form of an extruded strand.

DE 195 22 899 discloses a method for continuously sintering a granulate for the manufacture of compressed articles, particularly for tableted drug formulations. None of the components is melted in the extruder and no strand is extruded.

EP-A 0 043 254 discloses a pharmaceutical composition with a retarded liberation of an active material and a process for producing the same. An active material in finely divided form is mixed with both a finely divided high melting lipid or lipoid component and a finely divided low melting lipid or lipoid component, the resulting mixture is brought to a temperature which is above the melting point of the low melting component but below the melting point of the high melting component and the mixture, after melting of the low melting component, is allowed to cool to below the melting point thereof and subsequently worked up to give a finished pharmaceutical composition which has a controlled retarded liberation and which is safe, easy and not expensive to produce.

EP-A 229 652 discloses that certain acid compounds stabilize the potency of vitamin E compounds when processed into a dry particulate free-flowing form. A potency stabilized composition in a dry, particulate, free-flowing form is comprised of Vitamin E incorporated in a carrier whose potency has been stabilized with an effective amount of a certain acid compound. Such potency stabilizing acid compounds are hydroxy acids or amino acids, such as citric acid, ascorbic acid, methionine and cysteine.

EP-A 641 195 relates to a continuous method for the production of retarded pharmaceutical compositions by an extrusion process. A mixture of an active material, a low and high melting lipid or lipoid components is introduced by means of an extruder screw conveyor into a preheated extruder and brought to a temperature which is at most about 4° C. above the melting temperature of the low melting component at a pressure of about 200 to about 600 kPa (N/m²). The mass is extruded through a nozzle plate with a nozzle diameter of about 1.2 to about 4 mm and subsequently cooled, and if desired, granulated.

EP 2 246 063 relates to pharmaceutical compositions for the controlled and sustained release of active substance comprising a biodegradable polymer or copolymer. Furthermore, the reference relates to pharmaceutical compositions for the controlled and sustained release of at least one active substance such as peptides or hormones and analogues thereof and the manufacturing process of such pharmaceutical compositions.

WO 95/17174 discloses a process for making an ingestible, neutral tasting laxative composition by coating dioctyl sulfosuccinate with a material selected from the group consisting of $C_{14-18}$ fats, $C_{16-20}$ fatty acids, sucrose polyesters, $C_{14-18}$ fats and waxes, pH sensitive polymers, food gums, and combinations thereof. Preferably, two successive, different coatings are applied to the dioctyl sulfosuccinate by steps including either fluid bed coating, spray congealing, spray quenching, or spray drying.

WO 96/03979 relates to an apparatus and method for preparing solid forms with controlled release of the active ingredient according to the spray drying and spray congealing techniques by means of an atomizer utilizing the mechanical vibrations of resonant metal elements or nozzles so as to obtain very small droplets with very short spray length.

WO 98/35655 discloses a method of physically separating at least two active substances A and B in solid medicament forms, wherein a melting process is applied and active substance A is homogeneously intermingled with the higher-melting lipids or lipoid constituent and the mixture thus obtained is granulated or finely divided in another manner.

WO 2009/135680 relates to a process for preparing a powder comprising the steps of providing at least one first component being in liquid form or having a waxy consistency at ambient temperature, providing at least one second component having a melting point or melting point/range in the range from above ambient temperature to below the degradation temperature of said first component, forming a homogenous liquid mixture comprising said at least one first component and said at least one second component by stirring and heating the mixture to or keeping the mixture at a temperature in the range from above the melting point or melting point/range of said second component and below the degradation temperature of said first component, transferring the liquid mixture to at least one spray congealing unit by at least one transfer unit, which is adapted to keep the mixture in its liquid form during its transfer, spray congealing said mixture, and isolating the powder obtained upon spray congealing.

WO 2011/095314 discloses the extrusion of a mixture of melted excipients through an extruder having a certain temperature profile to allow congealing of melted solution and to exit the extruder in form of powder. However, the powder is comparatively coarse and conventional subsequent grinding steps do not provide fine powders satisfying all requirements.

Li Lei et al., Drug Development and Industrial Pharmacy, 32(8), 2006, 991-1002 relates to the characterization of poly(ethylene oxide) in hot-melt extrusion.

Andreas Gryczke et al., Colloids and Surfaces. B, Biointerfaces, 86(2), 2011, 275-284 relates to the development and evaluation of orally disintegrating tablets containing ibuprofen granules prepared by hot melt extrusion.

The aforementioned procedures are not satisfactory in every respect. With some procedures, generally only large amounts of excipients can be employed, other procedures are quite laborious and require sophisticated equipment, still other procedures yield coarse powders. There is a demand for a simple and effective method to continuously and homogenously incorporate incompatible pharmaceutical excipients in substantially differing amounts into pharmaceutical compositions. The method should minimize capital expenditures for new equipment, have no or reduced regulatory impact and should be flexible with respect to the chemical nature and amount of constituents that can be processed.

It is an object of the invention to provide methods for the preparation of powdery pharmaceutical compositions comprising a homogeneous mixture of at least two pharmaceutical excipients and having advantages over the methods of the prior art. The manufacture of the powdery pharmaceutical compositions should be possible in a continuous fashion and should encompass a limited number of method steps only.

This object has been achieved by the subject-matter of the patent claims.

The invention relates to a method for the preparation of a powdery pharmaceutical composition comprising a pharmaceutical excipient, preferably first pharmaceutical excipient, which is a polyalkylene glycol, more preferably polyethylene glycol, and a pharmaceutical component, preferably a second pharmaceutical excipient or a pharmacologically active substance (drug), more preferably alpha-tocopherol; optionally together with a third constituent, preferably another pharmaceutical excipient, wherein the pharmaceutical excipient is a polyalkylene glycol; the method comprising the step of (c) grinding a mixture of the pharmaceutical excipient and the pharmaceutical component at a temperature below ambient temperature.

It has been surprisingly found that incompatible pharmaceutical excipients and components, respectively, e.g. a hydrophilic pharmaceutical excipient, preferably first pharmaceutical excipient, which is a polyalkylene glycol, more preferably polyethylene glycol, and a hydrophobic pharmaceutical component, preferably second pharmaceutical excipient, more preferably alpha-tocopherol, can be converted into a fine powdery pharmaceutical composition in a simple grinding process below ambient temperature.

By the method according to the invention fine powders can even be obtained when the amount of the excipient and the component substantially differs from one another, e.g. when the pharmaceutical excipient is present in an amount of 99 wt.-% or more and the pharmaceutical component is present in an amount of 1 wt.-% or less, both percentages being related to the total weight of the powdery pharmaceutical composition.

It has been surprisingly found that cryo-milling of blends comprising alpha-tocopherol and polyethylene glycol (PEG) show better results than either jet milling or sizing of extruded material. The feasibility of the method according to the invention could be demonstrated by means of different mill apparatuses (i.e. plate mills, hammer mills). Cryogenic temperatures make brittle the material to be milled and this implies that the specific energy required for milling is reduced. Additionally, cryogenic milling prevents the materials from thermal damage, hinders the occurrence of undesirable chemical reactions between phases and reduces particles aggregation. Further, the method according to the invention allows the control of the particle size by a very simple operation, namely by changing the sieve net of the mill apparatus. This flexibility makes possible the manufacture of alpha-tocopherol/PEG blends with a tailored particle size-distribution, and thereby it is possible to modulate the behavior of the powders in relation with properties such as bioavailability, stability, flowability, adhesive strength, drying properties and solubility. The method according to the invention is robust and consistent to achieve particle size distribution (PSD) comparable to commercial alpha-tocopherol/PEG blends manufactured by spray-congealing, which is considered to be one of the most powerful technologies for the manufacture of solid dispersion microparticles It has also been found that cryo-milling does not affect physical-chemical characteristics of the milled composition. Cryo-milling can be applied to a wide range of alpha-tocopherol/PEG mass ratios (0.01 wt.-% to 70 wt.-%, preferably 0.1 wt.-% to 20 wt.-%, more preferably 0.5 wt. % to wt.-10%) whatever is the initial size of material. The method according to the invention is simple and cheaper than spray congealing processes. Further, the cryo-milled compositions do not affect physical characteristics (i.e. density, flowability, particle distribution) of resultant powder blends of drug products compared to the commercial alpha-tocopherol/PEG blends.

Figure 1:
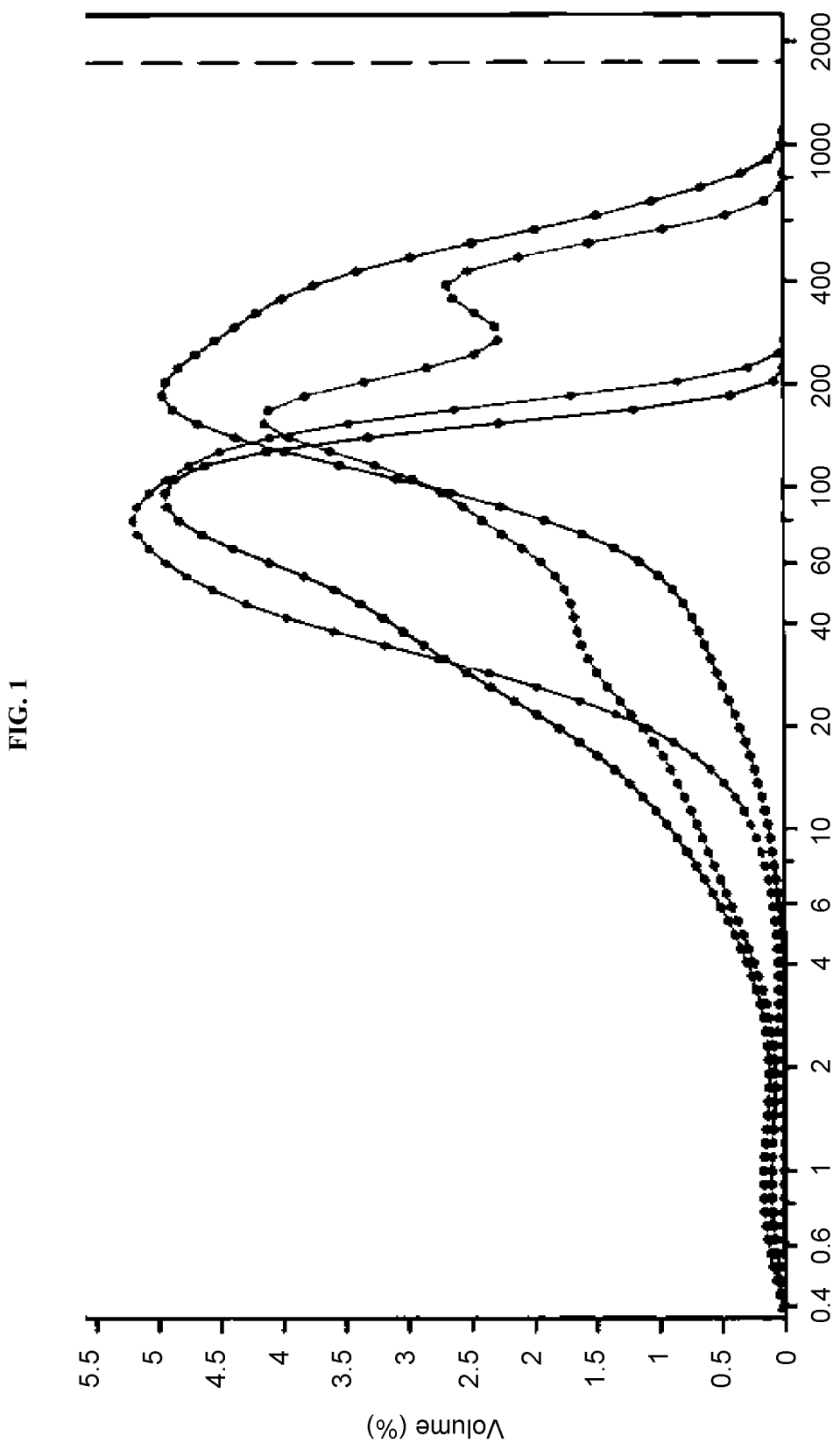
FIG. 1 compares the particle size distribution (PSD) of alpha-tocopherol/PEG with other excipients.

A first aspect of the invention relates to a method for the preparation of a powdery pharmaceutical composition comprising a pharmaceutical excipient, preferably first pharmaceutical excipient, which is a polyalkylene glycol, more preferably polyethylene glycol, and a pharmaceutical component, preferably second pharmaceutical excipient, more preferably alpha-tocopherol; the method comprising the step of (c) grinding a mixture of the pharmaceutical excipient and the pharmaceutical component at a temperature below ambient temperature.

Preferably, the grinding in step (c) is performed in form of a cryo-milling. For the purpose of the specification, the terms "grinding" and "milling" are synonymous.

Preferably, the temperature below ambient temperature is at most 0° C., or at most −5° C., or at most −10° C., or at most −15° C., or at most −20° C., or at most −25° C., or at most −30° C., or at most −35° C., or at most −40° C., or at most −45° C., or at most −50° C., or at most −55° C., or at most −60° C., or at most −65° C., or at most −70° C., or at most −75° C., or at most −80° C., or at most −85° C., or at most −90° C., or at most −95° C., or at most −100° C. Preferably, the temperature is that of liquid nitrogen (i.e. about −196° C.).

Preferably, the cryo-milling in step (c) of the method according to the invention is performed until the desired particle size and particle size distribution of the powdery pharmaceutical composition is achieved. The duration depends upon the equipment and the process parameters and can be determined by routine experimentation.

Cryo-milling in step (c) can be performed continuously or discontinuously.

Preferably, the pharmaceutical composition is subjected to cryo-milling in step (c) for at least about 10 seconds, or at least about 20 seconds, or at least about 30 seconds, or at least about 1 minute.

When cryo-milling in step (c) is performed continuously, the above time intervals refer to the mean residence time of the material within the mill.

In principle, many different mill apparatuses that are known to the skilled person can be used for cryo-milling, although some of them appear to better adapt to cryogenic conditions. Plate mills and hammer mills are preferred.

Typically, the mill is a cryo-mill, i.e. a mill capable of operating at low temperatures and being equipped with a suitable cooling system.

Preferably, the cryo-mill is equipped with a milling chamber comprising means for providing mechanical impact on the material to be milled, sometimes also referred to as "grinding jar". Depending upon the type of the cryo-mill, said mechanical impact may be provided in different forms that are known to the skilled person and that all have in common that the particle size of fine material is reduced through attrition and compressive forces at the grain size level. Suitable mills include but are not limited to ball mills, rod mills, autogenous mills, SAG mills, pebble mills, high pressure grinding rolls, Buhrstone mills, vertical shaft impactor mills (VSI mills), tower mills. Preferred mills are ball mills, colloid mills, conical mills, disintegrators, disk mills, edge mills, gristmills, hammer mills, jet mills, pellet mills, planetary mills, plate mills, stirred mills, and vibratory mills.

Further, the cryo-mill is preferably equipped with a sieve that allows material of the desired particle size to exit the milling chamber but keeps the coarser material within the milling chamber so that it is subjected to additional mechanical impact.

Still further, the cryo-mill is preferably equipped with a feeding device supplying the cryo-mill with starting material to be milled. Both the feeding device and the milling chamber are preferably equipped with isolating protections and integrated cooling, e.g. suitable pipeline to allow refrigeration with liquid nitrogen. The grinding jar is preferably continuously cooled with liquid nitrogen from the integrated cooling system before and during the grinding process. The sample is thus embrittled and volatile components are preserved. The liquid nitrogen preferably circulates through the system and is continuously replenished from an autofill system in the exact amount which is required to maintain the temperature at about −196° C.

In a preferred embodiment, cryo-milling is performed by means of a plate mill, e.g. a Hosokawa—Alpine (Germany). The mill preferably comprises a stainless steel milling chamber equipped with high speed rotating elements (plate beater) that apply a centrifugal force guiding the fed coarse material against a radial sieve of appropriate open sieve net. The milled material is then directly collected into a suitable container. Coarse material is preferably loaded by means of a feeding device directly in the center of the milling chamber.

In another preferred embodiment, cryo-milling is performed by means of a hammer mill, e.g. a Nuova Guseo (Italy). The mill preferably comprises a stainless steel milling chamber equipped with an horizontal rotor shaft which carries grinding elements (hammers) rotating at variable speed depending on the mill size. Coarse material is grinded by impact and attrition and finally forced through a radial sieve of appropriate open sieve net. Preferably, the milled material is then directly collected into a suitable container. The mill is preferably loaded by the top by means of an appropriate feeding device.

Milling may be performed continuously or batch-wise.

For the purpose of the specification, a "pharmaceutical composition" is any composition that is adapted for administration to an animal, typically oral administration of a human being.

The pharmaceutical composition according to the invention comprises a pharmaceutical excipient, preferably first pharmaceutical excipient, which is a polyalkylene glycol, more preferably polyethylene glycol, and a pharmaceutical component, preferably second pharmaceutical excipient, more preferably alpha-tocopherol.

For the purpose of specification, a "polyalkylene glycol" has a molecular weight of up to 50,000 g/mol, preferably up to 20,000 g/mol, whereas a "polyalkylene oxide" has a molecular weight of more than 50,000 g/mol, preferably more than 20,000 g/mol.

For the purpose of the specification the term "pharmaceutical component" encompasses both, pharmacologically active substances (drugs) as well as pharmaceutical excipients. Thus, preferably, the pharmaceutical component is selected from pharmacologically active substances and pharmaceutical excipients.

Pharmaceutical excipients are known to the skilled person (cf. e.g. R. C. Rowe et al., Handbook of Pharmaceutical Excipients, Pharmaceutical Press; 6th edition 2009; E.-M. Hoepfner et al., Fiedler—Encyclopedia of Excipients, Editio Cantor, 6th edition 2008).

For the purpose of the specification, a "pharmaceutical excipient" is preferably to be regarded as any pharmacologically inactive substance typically used as a carrier for the active ingredients of a medication. The pharmaceutical excipient may have a physiological effect, e.g. like a vitamin, but not a pharmacological effect, like a drug. Typical examples of pharmaceutical excipients include antiadherents, binders, coating materials, disintegrants, fillers, diluents, flavours, colorants, glidants, lubricants, preservatives, sorbents, sweeteners, and the like. Any of the foregoing excipients can be divided into sub-groups. For example, preservatives can be divided into antioxidants, buffers, antimicrobial substances and the like; whereas binders can be divided into solution binders and dry binders. Several excipients simultaneously exhibit different properties so that they can serve different purposes. For example, polyethylene glycol can be used as binder, plasticizer and the like.

Pharmacologically active substances are also known to the skilled person. In this regard, it can be referred to e.g. the Anatomical Therapeutic Chemical (ATC) classification system of the WHO.

In a preferred embodiment, the pharmaceutical component is a pharmacologically active substance (drug). Under these circumstances, the pharmaceutical composition according to the invention comprises the pharmacologically active substance already.

In another preferred embodiment, the pharmaceutical component is a second pharmaceutical excipient. Under these circumstances, the pharmaceutical composition according to the invention comprises at least two pharmaceutical excipients, namely the above pharmaceutical excipient (=first pharmaceutical excipient) and the pharmaceutical component (=second pharmaceutical excipient).

When the pharmaceutical component is a pharmacologically active substance, this is preferably selected from the group consisting of hormones and related compounds, such as estrogens, gestagens, androgens, anti-estrogens, anti-gestagens, anti-androgens; and analgesics, such as opioids, preferably selected from the group consisting of tramadol, tapentadol, oxycodone, oxymorphone, hydrocodone, hydromorphone, morphin; and the physiologically acceptable salts thereof.

When the pharmaceutical component is a second pharmaceutical excipient, the pharmaceutical composition according to the invention does not necessarily have to comprise a pharmacologically active substance (drug). Rather, the pharmaceutical composition may exclusively consist of two or more pharmaceutical excipients. Under these circumstances, the pharmaceutical composition is preferably adapted for being further processed into a pharmaceutical dosage form by addition of a pharmacologically active substance and optionally, further pharmaceutical excipients. Thus, in a preferred embodiment, the pharmaceutical composition can be regarded as an intermediate in the preparation of a pharmaceutical dosage form, which intermediate as such does not yet contain the pharmacologically active substance of the pharmaceutical dosage form.

In a preferred embodiment, the mixture comprises a third constituent, preferably another, i.e. additional pharmaceutical excipient.

When the mixture comprises a third constituent beside the pharmaceutical excipient and the pharmaceutical component, said third constituent is preferably an additional pharmaceutical excipient, more preferably a polymer, still more preferably a polyalkylene oxide, yet more preferably a polyethylene oxide having a weight average molecular weight of at least 1 Mio g/mol, most preferably a polyethylene oxide having a weight average molecular weight of at least 4 Mio g/mol.

In a preferred embodiment, the pharmaceutical composition essentially consists of a pharmaceutical excipient, preferably first pharmaceutical excipient, which is a polyalkylene glycol, more preferably polyethylene glycol, and a pharmaceutical component, preferably second pharmaceutical excipient, more preferably alpha-tocopherol, but does not contain any further ingredients, i.e. neither further pharmaceutical excipients nor pharmacologically active substances. In another preferred embodiment, the pharmaceutical composition essentially consists of a pharmaceutical excipient, preferably first pharmaceutical excipient, which is a polyalkylene glycol, more preferably polyethylene glycol, a pharmaceutical component, preferably second pharmaceutical excipient, more preferably alpha-tocopherol, and a third constituent, preferably an additional pharmaceutical excipient, more preferably a polymer, still more preferably a polyethylene oxide, but does not contain any further ingredients, i.e. neither further pharmaceutical excipients nor pharmacologically active substances.

The pharmaceutical excipient and the pharmaceutical component are not particularly limited.

Preferably, the pharmaceutical excipient, preferably first pharmaceutical excipient, is hydrophilic and the pharmaceutical component, preferably second pharmaceutical excipient, is hydrophobic, or vice versa. When the pharmaceutical composition comprises a third constituent, this is preferably hydrophilic as well.

A skilled person knows how to distinguish hydrophobic substances from hydrophilic substances. For the purpose of the specification, hydrophilic substances preferably have a solubility in pure water at 20° C. of at least 10 g/l, more preferably at least 50 g/l, still more preferably at least 100 g/l, yet more preferably at least 200 g/l, most preferably at least 300 g/l and in particular at least 400 g/l. For the purpose of the specification, hydrophobic substances preferably have a solubility in pure water at 20° C. of at most 1 g/l, more preferably at most 0.5 g/l, still more preferably at most 1.0 g/l, yet more preferably at most 0.05 g/l, most preferably at most 0.01 g/l and in particular at most 0.005 g/l.

In a preferred embodiment, the pharmaceutical excipient, preferably first pharmaceutical excipient, has a melting point/range within the range of 60±30° C., more preferably 60±25° C., still more preferably 60±20° C., yet more preferably 60±15° C., most preferably 60±10° C., and in particular 60±5.0° C.

In a preferred embodiment, the pharmaceutical component, preferably second pharmaceutical excipient, has a melting point/range within the range of 2.0±30° C., more preferably 2.0±25° C., still more preferably 2.0±20° C., yet more preferably 2.0±15° C., most preferably 2.0±10° C., and in particular 2.0±5.0° C.

In a preferred embodiment, the pharmaceutical component, preferably second pharmaceutical excipient, has a density (at 20° C.) within the range of 0.950±0.040 g/cm³, more preferably 0.950±0.030 g/cm³, still more preferably 0.950±0.025 g/cm³, yet more preferably 0.950±0.020 g/cm³, most preferably 0.950±0.015 g/cm³, and in particular 0.950±0.010 g/cm³.

In a preferred embodiment,
the pharmaceutical excipient, preferably first pharmaceutical excipient, is a polymer, more preferably a linear polymer, still more preferably a water-soluble polymer, yet more preferably a polyalkylene glycol, most preferably a polyethylene glycol; and/or
the pharmaceutical component, preferably second pharmaceutical excipient, is an antioxidant, preferably a tocopherol component, more preferably alpha-tocopherol.

For the purpose of the specification, the term "polyalkylene glycol" comprises e.g. polyethylene glycol, polypropylene glycol, blends thereof and copolymers thereof.

For the purpose of the specification, "tocopherol component" refers to alpha-tocopherol (vitamin E) and its derivatives such as tocopherol acetate.

In a preferred embodiment, the pharmaceutical excipient, preferably first pharmaceutical excipient, is a polyalkylene glycol, preferably a polyethylene glycol, having a weight average molecular weight within the range of from 6,000±5,000 g/mol, more preferably 6,000±4,000 g/mol, still more preferably 6,000±3,000 g/mol, yet more preferably 6,000±2,000 g/mol, most preferably 6,000±1,500 g/mol, and in particular 6,000±1,000 g/mol.

Preferably, the pharmaceutical composition does not contain any pharmacologically active substance (besides the tocopherol component).

In a preferred embodiment, the relative weight ratio of the pharmaceutical excipient, preferably first pharmaceutical excipient, which is a polyalkylene glycol, more preferably polyethylene glycol, to the pharmaceutical component, preferably second pharmaceutical excipient, more preferably alpha-tocopherol, is within the range of from 1000:1 to 1:1, more preferably 900:1 to 5:1, still more preferably 800:1 to 10:1, yet more preferably 700:1 to 15:1, most preferably 600:1 to 20:1, and in particular 500:1 to 25:1.

In a preferred embodiment, the relative weight ratio of the pharmaceutical excipient, preferably first pharmaceutical excipient, which is a polyalkylene glycol, more preferably polyethylene glycol, to the pharmaceutical component, preferably second pharmaceutical excipient, more preferably alpha-tocopherol, is at most 1000:1, more preferably at most 900:1, still more preferably at most 800:1, yet more preferably at most 700:1, most preferably at most 600:1 and in particular at most 500:1.

In another preferred embodiment, the relative weight ratio of the pharmaceutical excipient, preferably first pharmaceutical excipient, which is a polyalkylene glycol, more preferably polyethylene glycol, to the pharmaceutical component, preferably second pharmaceutical excipient, more preferably alpha-tocopherol, is at least 1:1, more preferably at least 5:1, still more preferably at least 10:1, yet more preferably at least 20:1, most preferably at least 30:1 and in particular at least 50:1.

When the pharmaceutical composition comprises a third constituent, preferably another pharmaceutical excipient, the relative weight ratio of the pharmaceutical excipient, preferably first pharmaceutical excipient, which is a polyalkylene glycol, more preferably polyethylene glycol, to said third constituent, preferably another pharmaceutical excipient, preferably polyethylene oxide, is within the range of from 99:1 to 1:5, more preferably 50:1 to 1:4, still more preferably 30:1 to 1:3, yet more preferably 20:1 to 1:2, most preferably 15:1 to 1:1 and in particular 10:1 to 2:1.

Preferably, the content of the pharmaceutical excipient, preferably first pharmaceutical excipient, which is a polyalkylene glycol, more preferably polyethylene glycol, in the pharmaceutical composition is at least 50 wt.-% or at least 55 wt.-%, still more preferably at least 60 wt.-% or at least 65 wt.-%, yet more preferably at least 70 wt.-% or at least 75 wt.-%, most preferably at least 80 wt.-%, at least 82.5 wt.-%, at least 85 wt.-% or at least 87.5 wt.-%, and in particular at least 90 wt.-%, at least 91 wt.-%, at least 92 wt.-%, at least 93 wt.-%, at least 94 wt.-%, at least 95 wt.-%, at least 96 wt.-%, at least 97 wt.-%, at least 98 wt.-%, or at least 99 wt.-%, based on the total weight of the pharmaceutical composition.

Preferably, the content of the optionally present third constituent, preferably another pharmaceutical excipient, more preferably polyethylene oxide, in the pharmaceutical composition is at least 0.1 wt.-% or at least 0.2 wt.-%, still more preferably at least 0.5 wt.-% or at least 1.0 wt.-%, yet more preferably at least 2.0 wt.-% or at least 5.0 wt.-%, most preferably at least 7.5 wt.-%, at least 10 wt.-%, at least 12.5 wt.-% or at least 15 wt.-%, and in particular at least 20 wt.-%, at least 25 wt.-%, at least 30 wt.-%, at least 35 wt.-%, at least 40 wt.-%, at least 45 wt.-%, at least 50 wt.-%, at least 55 wt.-%, at least 60 wt.-%, or at least 65 wt.-%, based on the total weight of the pharmaceutical composition.

Preferably, the content of the pharmaceutical component, preferably second pharmaceutical excipient, more preferably alpha-tocopherol, in the pharmaceutical composition is at most 50 wt.-% or at most 45 wt.-%, more preferably at most 40 wt.-% or at most 35 wt.-%, still more preferably at most 30 wt.-% or at most 25 wt.-%, yet more preferably at most 20 wt.-%, at most 17.5 wt.-%, at most 15 wt.-% or at most 12.5 wt.-%, most preferably 10 wt.-%, at most 9.0 wt.-%, at most 8.0 wt.-%, at most 7.0 wt.-%, or at most 6.0 wt.-%, and in particular at most at most 5.0 wt.-%, at most 4.0 wt.-%, at most 3.0 wt.-%, at most 2.0 wt.-%, or at most 1.0 wt.-%, based on the total weight of the pharmaceutical composition.

In a preferred embodiment, the content of the pharmaceutical component, preferably pharmacologically active ingredient, is at most 10 wt.-% or at most 9.0 wt.-%, more preferably at most 8.0 wt.-% or at most 7.0 wt.-%, still more preferably at most 6.0 wt.-% or at most 5.0 wt.-%, yet more preferably at most 4.5 wt.-%, at most 4.0 wt.-%, at most 3.5 wt.-% or at most 3.0 wt.-%, most preferably 2.5 wt.-%, at most 2.0 wt.-%, at most 1.5 wt.-%, at most 1.0 wt.-%, or at most 0.75 wt.-%, and in particular at most at most 0.5 wt.-%, at most 0.25 wt.-%, at most 0.1 wt.-%, at most 0.05 wt.-%, at most 0.01 wt.-%, at most 0.005 wt.-% or at most 0.001 wt.-%, based on the total weight of the pharmaceutical composition.

In a preferred embodiment, the content of the pharmaceutical component, preferably second pharmaceutical excipient, more preferably alpha-tocopherol, in the pharmaceutical composition is within the range of 14.0±5.0 wt.-%, more preferably 14.0±4.0 wt.-%, still more preferably 14.0±3.0 wt.-%, yet more preferably 14.0±2.0 wt.-%, most preferably 14.0±1.0 wt.-%, and in particular 14.0±0.5 wt.-%, based on the total weight of the pharmaceutical composition.

In another preferred embodiment, the content of the pharmaceutical component, preferably second pharmaceutical excipient, more preferably alpha-tocopherol, in the pharmaceutical composition is within the range of 12.0±5.0 wt.-%, more preferably 12.0±4.0 wt.-%, still more preferably 12.0±3.0 wt.-%, yet more preferably 12.0±2.0 wt.-%, most preferably 12.0±1.0 wt.-%, and in particular 12.0±0.5 wt.-%, based on the total weight of the pharmaceutical composition.

In still another preferred embodiment, the content of the pharmaceutical component, preferably second pharmaceutical excipient, more preferably alpha-tocopherol, in the pharmaceutical composition is within the range of 10.0±5.0 wt.-%, more preferably 10.0±4.0 wt.-%, still more preferably 10.0±3.0 wt.-%, yet more preferably 10.0±2.0 wt.-%, most preferably 10.0±1.0 wt.-%, and in particular 10.0±0.5 wt.-%, based on the total weight of the pharmaceutical composition.

In yet another preferred embodiment, the content of the pharmaceutical component, preferably second pharmaceutical excipient, more preferably alpha-tocopherol, in the pharmaceutical composition is within the range of 9.0±5.0 wt.-%, more preferably 9.0±4.0 wt.-%, still more preferably 9.0±3.0 wt.-%, yet more preferably 9.0±2.0 wt.-%, most preferably 9.0±1.0 wt.-%, and in particular 9.0±0.5 wt.-%, based on the total weight of the pharmaceutical composition.

In a preferred embodiment, the content of the pharmaceutical component, preferably second pharmaceutical excipient, more preferably alpha-tocopherol, in the pharmaceutical composition is within the range of 8.0±5.0 wt.-%, more preferably 8.0±4.0 wt.-%, still more preferably 8.0±3.0 wt.-%, yet more preferably 8.0±2.0 wt.-%, most preferably 8.0±1.0 wt.-%, and in particular 8.0±0.5 wt.-%, based on the total weight of the pharmaceutical composition.

In another preferred embodiment, the content of the pharmaceutical component, preferably second pharmaceutical excipient, more preferably alpha-tocopherol, in the pharmaceutical composition is within the range of 7.0±5.0 wt.-%, more preferably 7.0±4.0 wt.-%, still more preferably 7.0±3.0 wt.-%, yet more preferably 7.0±2.0 wt.-%, most preferably 7.0±1.0 wt.-%, and in particular 7.0±0.5 wt.-%, based on the total weight of the pharmaceutical composition.

In still another preferred embodiment, the content of the pharmaceutical component, preferably second pharmaceutical excipient, more preferably alpha-tocopherol, in the pharmaceutical composition is within the range of 6.0±5.0 wt.-%, more preferably 6.0±4.0 wt.-%, still more preferably 6.0±3.0 wt.-%, yet more preferably 6.0±2.0 wt.-%, most preferably 6.0±1.0 wt.-%, and in particular 6.0±0.5 wt.-%, based on the total weight of the pharmaceutical composition.

In yet another preferred embodiment, the content of the pharmaceutical component, preferably second pharmaceutical excipient, more preferably alpha-tocopherol, in the pharmaceutical composition is within the range of 5.0±2.5 wt.-%, more preferably 5.0±2.0 wt.-%, still more preferably 5.0±1.5 wt.-%, yet more preferably 5.0±1.0 wt.-%, most preferably 5.0±0.5 wt.-%, and in particular 5.0±0.25 wt.-%, based on the total weight of the pharmaceutical composition.

In another preferred embodiment, the content of the pharmaceutical component, preferably second pharmaceutical excipient, more preferably alpha-tocopherol, in the pharmaceutical composition is within the range of 4.0±2.5 wt.-%, more preferably 4.0±2.0 wt.-%, still more preferably 4.0±1.5 wt.-%, yet more preferably 4.0±1.0 wt.-%, most preferably 4.0±0.5 wt.-%, and in particular 4.0±0.25 wt.-%, based on the total weight of the pharmaceutical composition.

In still another preferred embodiment, the content of the pharmaceutical component, preferably second pharmaceutical excipient, more preferably alpha-tocopherol, in the pharmaceutical composition is within the range of 3.0±2.5 wt.-%, more preferably 3.0±2.0 wt.-%, still more preferably 3.0±1.5 wt.-%, yet more preferably 3.0±1.0 wt.-%, most preferably 3.0±0.5 wt.-%, and in particular 3.0±0.25 wt.-%, based on the total weight of the pharmaceutical composition.

In yet another preferred embodiment, the content of the pharmaceutical component, preferably second pharmaceutical excipient, more preferably alpha-tocopherol, in the pharmaceutical composition is within the range of 2.0±1.5 wt.-%, more preferably 2.0±1.25 wt.-%, still more preferably 2.0±1.0 wt.-%, yet more preferably 2.0±0.75 wt.-%, most preferably 2.0±0.5 wt.-%, and in particular 2.0±0.25 wt.-%, based on the total weight of the pharmaceutical composition.

In another preferred embodiment, the content of the pharmaceutical component, preferably second pharmaceutical excipient, more preferably alpha-tocopherol, in the pharmaceutical composition is within the range of 1.0±0.8 wt.-%, more preferably 1.0±0.6 wt.-%, still more preferably 1.0±0.5 wt.-%, yet more preferably 1.0±0.4 wt.-%, most preferably 1.0±0.3 wt.-%, and in particular 1.0±0.2 wt.-%, based on the total weight of the pharmaceutical composition.

The pharmaceutical composition is powdery. A "powder" is typically defined as an assembly of dry particles dispersed in air. For the purpose of the specification, "powdery" preferably means that the pharmaceutical composition is a dry bulk solid consisting of a large number of fine or very fine particles that may flow freely when shaken or tilted, i.e. that are not cemented together. Preferably, the texture is smooth in touch. In a preferred embodiment, the powdery pharmaceutical composition is free-flowing.

In a preferred embodiment, the powdery pharmaceutical composition is a homogeneous mixture of the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol and the optionally present third constituent. For the purpose of the specification, "homogeneous" preferably means that the standard deviation (SD) as a measure of blend uniformity (BU) of the powdery pharmaceutical composition is at most 5.0 SD %, more preferably at most 4.5 SD %, still more preferably at most 4.0 SD %, yet more preferably at most 3.5 SD %, most preferably at most 3.0 SD % and in particular at most 2.5 SD %. Methods to determine blend uniformity of powders are known to the skilled person. For example, a suitable method is near infrared spectroscopy (NIR), other methods are described in the Eur. Ph.

Preferably, the particle size (grain size) of the powdery pharmaceutical composition is comparatively fine.

In a preferred embodiment, at least 90 wt.-% of the powdery pharmaceutical composition passes sieve size 4.75 mm, 3.35 mm, 2.81 mm, 2.38 mm, or 2.00 mm; more preferably 1.68 mm, 1.40 mm, 1.20 mm, 1.00 mm, or 0.853 mm; still more preferably 0.710 mm, 0.599 mm, 0.500 mm, 0.422 mm, or 0.354 mm; yet more preferably 0.297 mm, 0.251 mm, 0.211 mm, 0.178 mm, or 0.152 mm; most preferably 0.125 mm, 0.104 mm, 0.089 mm, 0.075 mm, or 0.066 mm; and in particular 0.053 mm, 0.044 mm, or 0.037 mm.

In a particularly preferred embodiment, at least 90 wt.-% of the powdery pharmaceutical composition passes sieve size 1.00 mm, 0.95 mm, 0.90 mm or 0.85 mm.

In a preferred embodiment, the powdery pharmaceutical composition is free flowing and preferably, has an average particle size of at most 100 µm, more preferably at most 90 µm, still more preferably at most 80 µm, yet more preferably at most 70 µm, most preferably at most 60 µm and in particular at most 50 µm. Method to determine the average particle size of powders are known to the skilled person. A suitable method is for example laser light scattering or sieve analysis.

In a preferred embodiment, the powdery pharmaceutical composition is characterized by a d 10 value of 17±10 µm, more preferably 17±8 µm, still more preferably 17±6 µm, yet more preferably 17±5 µm, even more preferably 17±4 µm, most preferably 17±3 µm and in particular 17±2 µm.

In a preferred embodiment, the powdery pharmaceutical composition is characterized by a d 50 value of 80±30 µm, more preferably 80±25 µm, still more preferably 80±20 µm, yet more preferably 80±15 µm, even more preferably 80±10 µm, most preferably 80±8 µm and in particular 80±6 µm.

In a preferred embodiment, the powdery pharmaceutical composition is characterized by a d 90 value of 190±70 µm, more preferably 190±60 µm, still more preferably 190±50 µm, yet more preferably 190±40 µm, even more preferably 190±30 µm, most preferably 190±20 and in particular 190±10 µm.

When the method according to the invention involves preceding step (b) (see below), the powder which has exited the extruder is further grinded so that the particle size and particle size distribution of the final powdery pharmaceutical composition obtained in step (c) does not correspond to the particle size and particle size distribution of the powder that has exited the extruder in step (b).

Preferably, the method according to the invention additionally comprises the preceding step of (b) extruding a mixture of the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, in an extruder at a temperature profile allowing a liquid melt of the mixture to congeal in the extruder and to exit the extruder in form of a powder.

In optional step (b) of the method according to the invention, a mixture of the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, optionally together with a third constituent, preferably another pharmaceutical excipient, is extruded.

Typically, extrusion is regarded as a process used to create objects of a fixed cross-sectional profile. A material is pushed or drawn through a die of the desired cross-section. Two main advantages of this process over other manufacturing processes is its ability to create very complex cross-sections and work materials that are brittle, because the material only encounters compressive and shear stresses. It also forms finished parts with an excellent surface finish.

For the purpose of the invention, however, extrusion is preferably performed in an unusual fashion, namely so that the product, i.e. the extrudate, is a powder. This can be achieved by carefully adapting the extrusion parameters, e.g. screw geometry, extrusion temperature, screw speed, throughput, pressure and the like. Preferably, the extruder is not equipped with an extrusion die so that the pressure exerted to the mixture within the extruder is comparatively low. Preferably, the extruder is equipped neither with extrusion die nor with an adapter (e.g. Y-pipe).

For the purpose of the specification the term "extrudate" refers to any material exiting the extruder, e.g. an extruded strand or a powder.

Preferably, the pressure just ahead of the exit (outlet orifice) of the extruder does not exceed 25 bar or 20 bar, more preferably 15 bar or 10 bar, still more preferably 8.0 bar or 6.0 bar, yet more preferably 5.0 bar or 4.0 bar, most preferably 3.0 bar or 2.0 bar, and in particular 1.5 bar or 1.0 bar. The pressure just ahead of the exit of the extruder can be measured by conventional means and many commercialized extruders are already equipped with a respective manometer at the proper position. In a preferred embodiment, however, no pressure can be measured at all and the extrusion is performed under conditions imparting as minimal pressure as possible, preferably at most 1.0 bar, more preferably at most 0.8 bar, still more preferably at most 0.6 bar, yet more preferably at most 0.4 bar, most preferably at most 0.2 bar, and in particular at most 0.1 bar.

Preferably, the design of the screw elements and the extrusion conditions are adjusted to ensure that the extruded mass, in particular after its congealing, is not compacted or, if compaction cannot be completely avoided, the degree of compaction is as low as possible. A skilled person knows how to adjust such mild extrusion conditions, e.g. by regulating the screw speed.

Preferably, the extruder has an inner diameter of 10 mm to 100 mm, more preferably 12 mm to 90 mm, still more preferably 14 mm to 80 mm, most preferably 15 mm to 70 mm and in particular 15 mm to 60 mm. In a preferred embodiment, the extruder has an inner diameter of 18±10 mm, more preferably 18±8 mm, still more preferably 18±6 mm, yet more preferably 18±4 mm, most preferably 18±2 mm, and in particular 18±1 mm. In another preferred embodiment, the extruder has an inner diameter of 27±10 mm, more preferably 27±8 mm, still more preferably 27±6 mm, yet more preferably 27±4 mm, most preferably 27±2 mm, and in particular 27±1 mm. In yet another preferred embodiment, the extruder has an inner diameter of 50±10 mm, more preferably 50±8 mm, still more preferably 50±6 mm, yet more preferably 50±4 mm, most preferably 50±2 mm, and in particular 50±1 mm.

Preferably, the extruder has a length of 30 cm to 250 cm, more preferably 40 cm to 240 cm, still more preferably 50 cm to 230 cm, most preferably 60 cm to 220 cm and in particular 70 cm to 210 cm.

In a preferred embodiment, the ratio of extruder length in mm and extruder diameter in mm is within the range of 25±15, more preferably 25±10, still more preferably 25±8, yet more preferably 25±6, most preferably 25±4, and in particular 25±2.

In another preferred embodiment, the ratio of extruder length in mm and extruder diameter in mm is within the range of 30±15, more preferably 30±10, still more preferably 30±8, yet more preferably 3 0±6, most preferably 30±4, and in particular 30±2.

In still another preferred embodiment, the ratio of extruder length in mm and extruder diameter in mm is within the range of 40±15, more preferably 40±10, still more preferably 40±8, yet more preferably 40±6, most preferably 40±4, and in particular 40±2.

Preferably, the screw geometry is adapted so that the congealed material within the extruder is exerted a sufficient impact in order to yield a powdery pharmaceutical composition exiting the extruder. Thus, the extrusion parameters of the method according to the invention are preferably in contrast to the extrusion parameters of conventional methods where it is generally desired to manufacture a non-powdery extrusion strand having a smooth and excellent surface finish.

Typically, the screw geometry may be modified by varying the screw elements from which the screw is assembled. Conventional screw extruders are typically equipped with an extrusion axis adapted to carry a number of screw elements. Depending upon the extruder design and the design of the individual screw elements, the extrusion axis may carry about 10 to about 50 or more identical or different screw elements. In twin screw extruders (counter-rotating or co-rotating) the design of the individual screw elements must be such that contra-rotation or co-rotation about the two parallel extrusion axes is possible.

Preferably, each screw is equipped with (assembled from) at least 5, more preferably at least 10, most preferably 15 and in particular at least 20 identical or different screw elements.

The manufactures of screw extruders usually commercialize quite a number of different extrusion elements that can be employed in their extruders depending upon the individual demands of the extrusion technique. Examples of commercially available screw elements include screw transport elements, kneading elements, blank elements and the like. A skilled person is aware of typical screw elements.

Each screw element serves a particular purpose and a skilled person knows what screw element to choose in order to serve a particular purpose.

For example, a main purpose of screw transport elements is to effect transportation of the extruded material within the extruder from the inlet to the outlet and optionally, to impart the necessary pressure in front of the extrusion die. Screw transport elements can typically be divided in sub-types differing in their number of windings (threads) per standard length. For example, a screw transport element having two windings (threads) along a length of e.g. 100 mm differs from a screw transport element having three windings (threads) along the same length.

In contrast, a main purpose of kneading elements is to effect a vigorous mixing of the constituents of the extruded material without any substantial transportation. Kneading elements can typically also be divided in sub-types differing in their design and relative angle of kneaders. For example, a kneading element having two consecutive kneaders that are off-set 90° about the extrusion axis differs from a kneading element having two consecutive kneaders that are off-set 60° about the extrusion axis.

The design of the extrusion screws in the method according to the invention is not particularly limited. Preferably, however, each extrusion screw is equipped with (assembled from) a plurality of screw elements. Preferably, each extrusion screw comprises at least two different types of screw elements, more preferably at least three different types, still more preferably at least four different types, whereas every type of screw element may be represented by a single or a plurality of screw elements (i.e., of the same type). Screw elements of the same type may be located next to one another or in alternating, regular or irregular order and sequence with screw elements of other type(s), respectively.

In a preferred embodiment, each extrusion screw comprises at least having one screw element with a pitch (axial distance for one revolution of screw flight expressed as ratio to screw diameter (D)) within the range of 1.25±1.0 D, more preferably 1.25±0.75 D, still more preferably 0.5±0.4 D, 1.0±0.5 D or 1.75±0.5 D, yet more preferably 0.5±0.3 D, 1.0±0.4 D or 1.75±0.4 D, and most preferably 0.5±0.25 D, 1.0±0.25 D or 1.75±0.25 D.

In a preferred embodiment of the method according to the invention, each extrusion screw is equipped with (assembled from) at least two different types of screw transport elements differing, optionally inter alia, in their number of windings (threads) per standard length, whereas in at least a portion of the extrusion screw the type of screw transport elements having the lower number of windings (threads) is located upstream with respect to the screw transport elements having the higher number of windings (threads).

In another preferred embodiment of the method according to the invention, each extrusion screw is equipped with (assembled from) at least two different types of screw transport elements differing, optionally inter alia, in their chamber volume per standard length, whereas in at least a portion of the extrusion screw the type of screw transport elements having the smaller chamber volume is located upstream with respect to the screw transport elements having the larger chamber volume. For the purpose of the specification, the chamber volume is to be regarded as the space between the screw elements and the extruder wall, i.e. the inner hollow space that guides the extruded mass through the extruder.

Preferably, each extrusion screw is equipped with (assembled from) at least two different types of screw transport elements (a) and (b), whereas each type of screw transport element is represented by one or more individuals. In a preferred embodiment, the number of windings (threads) per standard length of elements (b) exceeds the number of windings (threads) of elements (a). In another preferred embodiment, the chamber volume per standard length of elements (b) exceeds the chamber volume of elements (a). In still another preferred embodiment, the pitch of elements (b) exceeds the pitch of elements (a). In yet another preferred embodiment, the conveying speed of elements (b) exceeds the conveying speed of elements (a). In another preferred embodiment, the volumetric displacement of elements (b) exceeds the volumetric displacement of elements (a). Preferably, a sequence of four consecutive elements that are independently chosen from screw transport elements of type (a) and screw transport elements of type (b) forms a portion of the extrusion screw.

In a preferred embodiment, the length of the extrusion screw corresponds to the length of the extruder so that the entire extrusion screw is mounted by the extruder block. In another preferred embodiment the length of the extrusion screw is such that it protrudes from the extruder block, typically by several cm, e.g. about 2.5, 5 or 7.5 cm.

The method according to the invention comprises the extrusion of a mixture of the pharmaceutical excipient and the pharmaceutical component in an extruder at a temperature profile allowing a liquid melt of the mixture to congeal in the extruder and to exit the extruder in form of a powder. Thus, when the extruder is a screw extruder, its extrusion axis or axes, respectively, comprise an upstream portion that serves the purpose of extruding the not yet congealed mixture and a downstream portion that serves the purpose of extruding the congealed mixture.

In a preferred embodiment of the method according to the invention, the screw elements forming said downstream portion of the extrusion screw comprise screw elements imparting a relatively high mechanical impact on the congealed mixture in order to yield a powdery pharmaceutical composition. Thus, as far as the design of the extrusion elements in this downstream portion is concerned, extrusion conditions are comparatively harsh.

Preferably, parallel to the temperature profile in the extruder that allows the liquid melt of the mixture to congeal in the extruder and to exit the extruder in form of a powder, there is an extrusion screw profile increasing the mechanical impact exerted by the extrusion elements further supporting that the extruded material exits the extruder in form of a powder.

The extruder is preferably equipped with at least two heating elements that can be adjusted to different temperatures independently. Preferably, the extruder comprises at least three, more preferably at least four, still more preferably at least five, yet more preferably at least six, most preferably at least seven and in particular at least eight of such heating elements adjustable to different temperatures independently.

These heating elements allow adjusting the desired temperature profile within the extruder.

Preferably, the extruder is equipped with at least four consecutive heating elements $H_1$, $H_2$, $H_3$ and $H_4$ which are set at the corresponding temperatures $T_1$, $T_2$, $T_3$ and $T_4$, respectively. $H_1$ is located upstream with respect to $H_2$ to $H_4$, $H_2$ is located upstream with respect to $H_3$ and $H_4$ and $H_3$ is located upstream with respect to $H_4$. Preferred embodiments of the relationship $T_1$ to $T_4$ are summarized here below:
$T_1=T_2=T_3=T_4$; $T_1>T_2=T_3=T_4$; $T_1=T_2>T_3=T_4$;
$T_1=T_2=T_3>T_4$; $T_1<T_2=T_3=T_4$; $T_1=T_2<T_3=T_4$;
$T_1=T_2=T_3<T_4$; $T_1>T_2>T_3=T_4$; $T_1>T_2=T_3>T_4$;
$T_1=T_2>T_3>T_4$; $T_1<T_2<T_3=T_4$; $T_1<T_2=T_3<T_4$;
$T_1=T_2<T_3<T_4$; $T_1>T_2>T_3>T_4$; or $T_1<T_2<T_3<T_4$.

Preferably, in step (b) of the method according to the invention, extrusion is performed by means of a screw extruder, preferably a twin screw extruder having contra-rotating or co-rotating screws. It is also possible to perform extrusion by means of a planetary gear extruder (planetary roller extruder). Suitable extruders are known to the skilled person and commercially available. A suitable twin screw extruder is for example commercialized by Leistritz, type ZSE 18PH 40 D.

A skilled person recognizes, however, that the gist of the method according to the invention can also be realized by equivalent means typically employed in order to process viscous or highly viscous masses, wherein processing typically involves heating, mixing, cooling, shearing, and/or the like. Exemplified means include roll coolers or barrel coolers, cool belts, granulators, coaters, etc.

In the course of the extrusion process, the extruded material is typically transported along the longitudinal axis of the extruder from the inlet (feeding point) to the outlet (exit). Material movement is typically effected by the rotation of the screws and by the new starting material entering the inlet of the extruder. For the purpose of the specification, two locations along the longitudinal axis of the extruder may be qualified as "upstream" and "downstream" with respect to the direction of extrusion. The location upstream is closer to the inlet of the extruder than the location downstream and vice versa, the location downstream is closer to the exit of the extruder than the location upstream.

The temperature profile within the extruder is adjusted to ensure that a liquid melt of the mixture is allowed to congeal in the extruder before it exits the extruder. Thus, according to the method of the invention, at least at one upstream location within the extruder the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, optionally together with a third constituent, preferably another pharmaceutical excipient, are present in the molten state. Melting is typically achieved by adjusting the temperature profile so that at said upstream location the temperature of the mixture (extruded material) is sufficiently high.

This does not necessarily mean that the temperature of the mixture (extruded material) in the extruder at said one upstream location must be above the melting points/ranges of both, the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, and the optionally present third constituent, preferably another pharmaceutical excipient. Depending upon the nature and the amount of the excipients it may be sufficient that the temperature is above the melting point/range of just one of the two or three ingredients so that it forms a liquid melt in which the other is (are) dissolved.

Preferably, however, the temperature of the mixture (extruded material) in the extruder at said one upstream location is above the melting points/ranges of both, the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, and the optionally present third constituent.

The liquid melt may be formed, i.e. generated, within the extruder by initially heating the mixture (extruded material) having a temperature below its melting point/range to a temperature above its melting point/range so that a liquid melt is formed. Alternatively, however, the liquid melt may already be fed into the extruder, i.e. the liquid melt of the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, optionally together with a third constituent, preferably another pharmaceutical excipient, may be formed outside the extruder and then be supplied to the inlet of the extruder so that the starting material enters the extruder already in molten liquid state. Preferably, said liquid state is maintained for a while in the course of the extrusion process.

In the course of the extrusion process and as a consequence of the temperature profile, the liquid melt is allowed to congeal in the extruder. The liquid melt congeals, i.e. solidifies to a solid material by cooling. Thus, according to the method of the invention, at least at one downstream location within the extruder the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, optionally together with a third constituent, preferably another pharmaceutical excipient, are present in the congealed, i.e. solidified state. Congealing is typically achieved by adjusting the temperature profile so that at said downstream location the temperature of the mixture (extruded material) is sufficiently low.

This does not necessarily mean that the temperature of the mixture (extruded material) in the extruder at said one downstream location must be below the melting points/ranges of both, the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, and the optionally present third constituent. Depending upon the nature and the amount of the excipients it may be sufficient that the temperature is below the melting point/range of just one of the two ingredients so that it solidifies with the other ingredient being dissolved in it.

Preferably, when the congealed mixture exits the extruder, it has a temperature of at least 5° C., preferably at least 10° C., more preferably at least 15° C., still more preferably at least 20° C., yet more preferably at least 25° C., most preferably at least 30° C. and in particular at least 35° C., below the melting point/temperature of the pharmaceutical excipient, preferably first pharmaceutical excipient, which is a polyalkylene glycol, more preferably polyethylene glycol, and/or the pharmaceutical component, preferably second pharmaceutical excipient, more preferably alpha-tocopherol and/or the optionally present third constituent.

In a preferred embodiment of the method according to the invention, in step (b) the temperature profile comprises a temperature gradient of temperature $T_1$ to temperature $T_2$, where $T_1 > T_2$ and where $T_1$ is above the melting point/range of the pharmaceutical excipient, preferably first pharmaceutical excipient, which is a polyalkylene glycol, more preferably polyethylene glycol, and/or the pharmaceutical component, preferably second pharmaceutical excipient, more preferably alpha-tocopherol and/or the optionally present third constituent; and/or $T_2$ is below the melting point/range of the pharmaceutical excipient, preferably first pharmaceutical excipient, which is a polyalkylene glycol, more preferably polyethylene glycol and/or pharmaceutical component, preferably second pharmaceutical excipient, more preferably alpha-tocopherol, and/or the optionally present third constituent.

$T_1$ and $T_2$ are preferably adjusted be means of the heating elements of the extruder. Preferably $T_1$ and $T_2$ correspond to the temperatures at which the heating elements are heated.

Preferably, $T_1$ is within the range of from 25° C. to 115° C., or 30° C. to 110° C., more preferably 35° C. to 105° C., or 40° C. to 100° C., still more preferably 45° C. to 95° C., or 50° C. to 90° C., yet more preferably 55° C. to 85° C., most preferably 60° C. to 80° C., and in particular 65° C. to 75° C.; and/or $T_2$ is within the range of from −20° C. to 50° C., more preferably −10° C. to 40° C., still more preferably −5° C. to 35° C., yet more preferably 0° C. to 30° C., most preferably 5° C. to 25° C., and in particular 10° C. to 20° C.

In a preferred embodiment, $T_1$ is at least 0.5° C. or at least 1.0° C., more preferably at least 1.5° C. or at least 2.0° C., still more preferably at least 2.5° C. or at least 3.0° C., yet more preferably at least 3.5° C. or at least 4.0° C., most preferably at least 4.5° C. or at least 5.0° C., and in particular at least 5.5° C. or at least 6.0° C. above the melting point of the pharmaceutical excipient, preferably first pharmaceutical excipient, which is a polyalkylene glycol, more preferably polyethylene glycol, and/or the pharmaceutical component, preferably second pharmaceutical excipient, more preferably alpha-tocopherol and/or the optionally present third constituent.

In another preferred embodiment, $T_1$ is at least 5° C. or at least 10° C., more preferably at least 15° C. or at least 20° C., still more preferably at least 25° C. or at least 30° C., yet more preferably at least 35° C. or at least 40° C., most preferably at least 45° C. or at least 50° C., and in particular at least 55° C. or at least 60° C. above the melting point of the pharmaceutical excipient, preferably first pharmaceutical excipient, which is a polyalkylene glycol, more preferably polyethylene glycol, and/or the pharmaceutical component, preferably second pharmaceutical excipient, more preferably alpha-tocopherol and/or the optionally present third constituent.

In a preferred embodiment, $T_2$ is at least 1.0° C. or at least 2.0° C., more preferably at least 3.0° C. or at least 4.0° C., still more preferably at least 5.0° C. or at least 6.0° C., yet more preferably at least 7.0° C. or at least 8.0° C., most preferably at least 9.0° C. or at least 10° C., and in particular at least 11° C. or at least 12° C. above the melting point of the pharmaceutical excipient, preferably first pharmaceutical excipient, which is a polyalkylene glycol, more preferably polyethylene glycol, and/or the pharmaceutical component, preferably second pharmaceutical excipient, more preferably alpha-tocopherol and/or the optionally present third constituent.

In another preferred embodiment, $T_2$ is at least 2.5° C. or at least 5.0° C., more preferably at least 7.5° C. or at least 10° C., still more preferably at least 12.5° C. or at least 15° C., yet more preferably at least 17.5° C. or at least 20° C., most preferably at least 25° C. or at least 30° C., and in particular at least 35° C. or at least 40° C. below the melting point of the pharmaceutical excipient, preferably first pharmaceutical excipient, which is a polyalkylene glycol, more preferably polyethylene glycol, and/or the pharmaceutical component, preferably second pharmaceutical excipient, more preferably alpha-tocopherol and/or the optionally present third constituent.

In a preferred embodiment, the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, and the optionally present third constituent, are fed into the extruder in form of a liquid melt having a sufficiently high temperature, preferably within the range of $T_1 \pm 10°$ C., more preferably $T_1 \pm 8.0°$ C., still more preferably $T_1 \pm 6.0°$ C., yet more preferably $T_1 \pm 4.0°$ C., most preferably $T_1 \pm 2.0°$ C., and in particular $T_1 \pm 1.0°$ C.

The congealed mixture then exits the extruder in form of a powder. This means that in the extruder the liquid melt does not only congeal into a solid material but is further comminuted into a powder, at least to a certain extent.

In a preferred embodiment, the method according to the invention comprising steps (b) and (c) comprises the preceding step of
(a) mixing the pharmaceutical excipient, preferably first pharmaceutical excipient, which is a polyalkylene glycol, more preferably polyethylene glycol, with the pharmaceutical component, preferably second pharmaceutical excipient, more preferably alpha-tocopherol, and the optionally present third constituent, outside the extruder and then feeding the resultant mixture into the extruder; or
feeding the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, and the optionally present third constituent, into the extruder at different feeding points, where the feeding point for the pharmaceutical excipient, preferably first pharmaceutical excipient, which is a polyalkylene glycol, more preferably polyethylene glycol, is located upstream with respect to the feeding point for the pharmaceutical component, preferably second pharmaceutical excipient, more preferably alpha-tocopherol, or vice versa.

Step (a) precedes step (b), i.e. step (b) is performed after step (a) has been completed.

Preferably, in step (a) the pharmaceutical component, preferably second pharmaceutical excipient, more preferably alpha-tocopherol, is dissolved in the molten pharmaceutical excipient, preferably first pharmaceutical excipient, which is a polyalkylene glycol, more preferably polyethylene glycol and/or the optionally present third constituent, or vice versa.

In another preferred embodiment, the method according to the invention comprises the subsequent step of
(d) grading the powder.

Typically, the method according to the invention does not comprise any spray congealing or spray drying step. It has been surprisingly found that by the method according to the invention laborious steps that require sophisticated equipment and process control can be omitted without deteriorating product quality. Thus, in a particularly preferred embodiment, besides extrusion, the method according to the invention does not comprise any separate grinding, spray congealing or spray drying steps.

The method according to the invention can be performed batch-wise or continuously.

Preferably, the method is performed continuously and a mixture of the pharmaceutical excipient, preferably first pharmaceutical excipient, which is a polyalkylene glycol, more preferably polyethylene glycol, and the pharmaceutical component, preferably second pharmaceutical excipient, more preferably alpha-tocopherol, and the optionally present third constituent, is automatically dosed into the extruder, preferably in form of a melt. First preliminary tests revealed that continuous dosing can be realized by standard equipment.

A further aspect of the invention relates to a method for the manufacture of a pharmaceutical dosage form comprising the method according to the invention as described above. Preferably, the pharmaceutical dosage form has a breaking strength of at least 400 N, more preferably at least 500 N, still more preferably at least 600 N, yet more preferably at least 700 N, most preferably at least 800 N and in particular at least 900 N. Dosage forms exhibiting such a high breaking strength are known from the prior art. In this regard it can be referred to e.g. WO 2005/016313, WO 2005/016314, WO 2005/063214, WO 2005/102286, WO 2006/002883, WO 2006/002884, WO 2006/002886, WO 2006/082097, WO 2006/082099, WO 2008/107149 and WO2009/092601.

Preferably, the method for the manufacture of a pharmaceutical dosage form comprises the step of formulating the powdery pharmaceutical composition comprising the first pharmaceutical excipient and the second pharmaceutical excipient and the optionally present third constituent, as described above together with
a pharmacologically active substance, preferably an opioid, and/or
a high molecular weight polyalkylene oxide, preferably polyethylene oxide, preferably having a weight average molecular weight of a least 200,000 g/mol, more preferably at least 500,000 g/mol, still more preferably at least 750,000 g/mol, yet more preferably at least 1,000,000 g/mol and in particular within the range of from 1,000,000 g/mol to 10,000,000 g/mol; and/or
a cellulose ether, preferably hydroxypropylmethyl cellulose or hydroxypropylcellulose.

Thus, in the method for the manufacture of a pharmaceutical dosage form according to the invention, the powdery pharmaceutical composition is preferably employed as intermediate.

Preferably, the powdery pharmaceutical composition does not substantially alter the release of the pharmacologically active substance from the pharmaceutical dosage form, i.e. the in vitro release profile of the pharmaceutical dosage form is not substantially influenced by the presence of the powdery pharmaceutical composition. In this regard, "substantially" preferably means 2%, more preferably 1%, i.e. the presence of the powdery pharmaceutical composition preferably does not alter the in vitro release profile by more than 2% compared to a dosage form not containing the powdery pharmaceutical composition.

In a preferred embodiment, the total amount of the (first) pharmaceutical excipient contained in the pharmaceutical dosage form originates from the powdery pharmaceutical composition, i.e. preferably no further (first) pharmaceutical excipient is added in the course of manufacturing the pharmaceutical dosage form from the powdery pharmaceutical composition.

In a preferred embodiment, the pharmaceutical dosage form contains the pharmaceutical composition in such an amount that the content of the (first) pharmaceutical excipient is within the range of from 1.0 to 20 wt.-%, more preferably 2.0 to 18 wt.-%, still more preferably 4.0 to 16 wt.-%, yet more preferably 6.0 to 14 wt.-%, most preferably 7.0 to 13 wt.-%, and in particular 8.0 to 12 wt.-%, relative to the total weight of the pharmaceutical dosage form.

The invention is further illustrated by the following examples which, however, are not to be construed as limiting its scope.

EXAMPLE 1—EXTRUSION—MANUFACTURE OF PRE-BLEND alpha-tocopherol-polyethylene glycol 6000 pre-blends were manufactured by means of a twin-screw extruder, type Leistritz ZSE27.

All trials were carried out with a screw configuration without kneading elements.

Only trials of 4% alpha-tocopherol concentration with high screw speed (trial 10 and trial 11) were tested with another screw configuration, because with a lower screw speed the extruder throughput was too low. These trials are identified with "bis".

| Factors | Level − | Level 0 | Level + |
|---|---|---|---|
| alpha-tocopherol content [wt.-%] | 4 | 14 | 14 |
| Feed rate [kg/h] | 2 | 4 | 6 |
| Screw speed [rpm] | 30 | 80 | 130 |

In a $2^3$ full factorial design, the following three parameters were varied: alpha-tocopherol content, feed rate, and screw speed. The experimental design thus consisted of 8 runs plus three center point runs for a total of 11 runs. A total of 4 kg of alpha-tocopherol/PEG blend were manufactured in each run.

The experimental design of trails 1 to 11 is summarized in the table here below:

| trial | batch | alpha-tocopherol concentration [%] | feed rate [kg/h] | speed [rpm] |
|---|---|---|---|---|
| 1 | 1 | 14% | 4 | 80 |
| 2 | | | 2 | 130 |
| 3 | | | 6 | 30 |
| 4 | | | 4 | 80 |
| 5 | | | 6 | 130 |
| 6 | | | 2 | 30 |
| 7 | | | 4 | 80 |
| 8 | 2 | 4% | 6 | 30 |
| 9 | | | 2 | 30 |
| 10 | | | 2 | 130 |
| 11 | | | 6 | 130 |

No significant differences among the trials could be observed. A coarse and waxy material was obtained that was difficult to characterize.

The following particle size distribution (PSD) was determined after 500 μm screening:

| alpha-tocopherol/PEG 4% | Yield after screening (<500 μm % w) |
|---|---|
| Trial 8 | 65.0 |
| Trial 8 (repeated) | 67.6 |
| Trial 9 | 34.0 |
| Trial 10 | 30.9 |
| Trial 10bis | 34.0 |
| Trial 11 | 36.0 |
| Trial 11bis | 32.7 |

The particle size distribution (PSD) comparison of alpha-tocopherol/PEG with other excipients is also shown in FIG. 1.

Trials 8 and 9 (alpha-tocopherol/PEG 4%) were repeated. alpha-tocopherol/PEG 4% trials led to fine particle size, especially in Trial 8 and in Trial 8 (repeated). Only a few coarse particles were visible.

Trial 8 showed a finer particle size than the other trials. 65 wt.-% of particle had an average diameter of less than 500 μm. Trial 8 was repeated at the end of the design of experiments confirming the results. The yield was too low for industrial application. Under these conditions, it was not possible to achieve acceptable powder state at concentration of 14 wt.-% of alpha-tocopherol.

Subsequently, cryo-milling equipments of two manufacturers were tested:

Hosokawa—Alpine (Germany) (Example 2)

Nuova Guseo (Italy) (Example 3)

EXAMPLE 2—CRYO-MILLING OF PRE-BLEND—HOSOKAWA—ALPINE

The pre-blends of Example 1 comprising alpha-tocopherol/PEG were subsequently subjected to cry-milling in order to obtain fine powders pharmaceutical compositions.

Pre-Blends:

| alpha-tocopherol/PEG 6000 14% | 14% material is coarse and waxy, consisting of aggregates of different size |
|---|---|
| alpha-tocopherol/PEG 6000 4% | 4% material consists of fine particle size, with few coarse particles visible |

Milling trials were performed on 100-UPZ (Hosokawa Alpine) varying the follows process parameters: rotation speed of the plate beater (rpm), temperature, feed rate (kg/h). Only two trials of 14% concentration (trial 9 and 10) were performed with 100 AFG Jet-Mill Micronizer (Hosokawa Alpine).

The material was charged in a screw feeding device. The material fell in a liquid nitrogen bath, and was cooled down to temperatures around −120° C. A whirling screw system transported the brittle material under liquid nitrogen to the grinding system, equipped with a plate rotating beater and a 0.5 mm sieve.

Milling in Hosokawa Alpine: Trials Performed on Alpha-Tocopherol/PEG 4%:

| trial | machine | apparatus | feed rate (kg/h) | temperature (from-to) | alpha-tocopherol content (batch) |
|---|---|---|---|---|---|
| 1 | 100UPZ - 14000 RPM | liquid nitrogen; plate beater; sieve 0.5 mm | 7.5 | −60° C./−70° C. | 4% |
| 2 | 100UPZ - 18000 RPM | liquid nitrogen; plate beater; sieve 0.5 mm | 5.0 | −100° C./−120° C. | 4% |
| 3 | 100UPZ - 18000 RPM | liquid nitrogen; plate beater; sieve 0.5 mm | 12 | −57° C./−62° C. | 4% |
| 4 | 100UPZ - 18000 RPM | liquid nitrogen; plate beater; sieve 0.5 mm | 20 | −70° C./−80° C. | 4% |
| 5 | 100UPZ - 18000 RPM | liquid nitrogen; plate beater; sieve 0.5 mm | 30 | −30° C./−40° C. | 4% |

The better trial in terms of feed rate was trial 5, performed on alpha-tocopherol/PEG 4%. This batch, produced in the preliminary design of experiments, had a less fine particle size compared to the batches of trials 1 to 4, but better flow property. There were no significant differences among electric current consumption of the system before and after the addition of materials: this indicates that the system can work without trouble even at high feed rate. The standard screw feeding device allows the loading of material. There was no deposit in the milling tools.

Milling in Hosokawa Alpine: Trials Performed on Alpha-Tocopherol/PEG 14%:

| Trial | Machine | Apparatus | Feed rate (Kg/h) | Temperature (from-to) | alpha-tocopherol content (batch) |
|---|---|---|---|---|---|
| 6 | 100UPZ - 14000 RPM | liquid nitrogen; plate beater; sieve 0.5 mm | 13.6 | −10° C./−25° C. | 14% |
| 7 | 100UPZ - 14000 RPM | liquid nitrogen; plate beater; sieve 0.5 mm | 20 | −10° C./−25° C. | 14% |
| 8 | 100UPZ - 14000 RPM | liquid nitrogen; plate beater; sieve 0.5 mm | 17 | −10° C./−25° C. | 14% |
| 9 | 100AFG 1000 | nozzles 1.9 mm 6 bar | 1.4 | n/a | 14% |
| 10 | 100AFG 2000 | nozzles 1.9 mm 6 bar | 0.4 | n/a | 14% |

Severe dosing problems on the screw feeder were observed, due the material dimension and the low melting temperature. Feeding was possible with a vibrating feeding system. There were no significant differences among electric current consumption of the system before and after the addition of materials: this indicates that the system can work without trouble even at high feed rate. There was no deposit in the milling tools.

After milling, a fine white powder was obtained.

Flowablity test failed for nozzles 6 mm and 10 mm with stirrer on or off, as the reference (commercial spray-congealed blend). Bulk density was comparable among the trials and with the reference (commercial spray-congealed blend). Tapped density was not considered a significant parameter, due the clogging that happens for the reference material. DSC profiles of material before and after milling were similar and there were no significant differences with the DSC profile of the reference (commercial spray-congealed blend).

The bulk densities are displayed in the table here below:

| alpha-tocopherol/PEG 4% | content of alpha-tocopherol | Density Bulk g/ml |
|---|---|---|
| Trial 1 | 4 wt.-% | 0.502 |
| Trial 2 | | 0.511 |
| Trial 3 | | 0.494 |
| Trial 4 | | 0.475 |
| Trial 5 | | 0.486 |
| Trial 6 | 14 wt.-% | 0.440 |
| Trial 7 | | 0.439 |
| Trial 8 | | 0.433 |
| Trial 9 | | 0.505 |
| Trial 10 | | 0.404 |
| alpha-tocopherol/PEG 14% commercial blend | | 0.438 |

Figure 2:
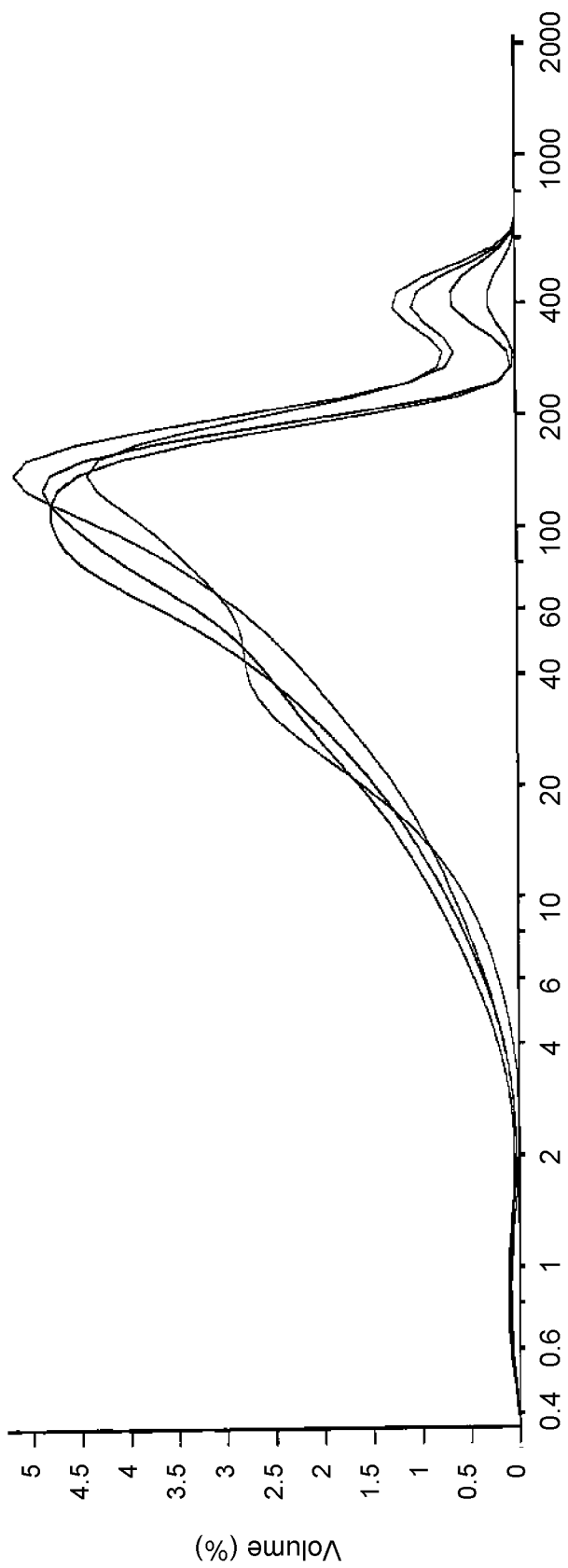
FIG. 2 shows the particle size distribution (PSD) of Trials 6, 7 and 8 in comparison to that of a commercial vitamin E/PEG 6000 blend.

The particle size distribution (PSD) of Trials 6, 7 and 8 in comparison to that of the commercial alpha-tocopherol/PEG 6000 blend is shown in FIG. 2.

| alpha-tocopherol/PEG 14% | d 10 (μm) | d 50 (μm) | d 90 (μm) |
|---|---|---|---|
| Trial 6 | 15.1 | 72.8 | 167.0 |
| Trial 7 | 13.0 | 70.2 | 162.7 |
| Trial 8 | 16.41 | 89.7 | 209.2 |
| alpha-tocopherol/PEG 14% commercial blend | 18.86 | 80.49 | 220.2 |

Figure 3:
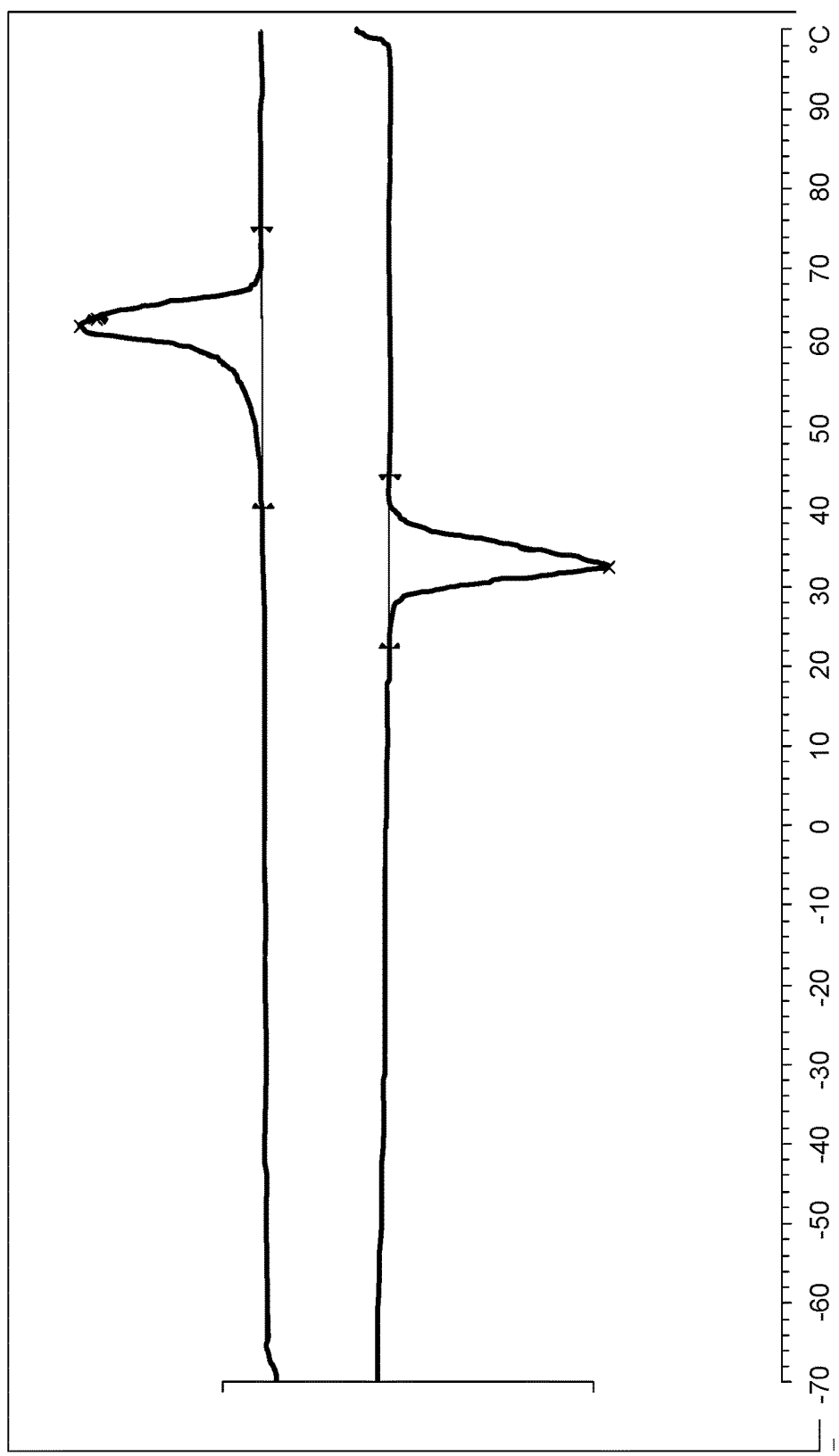
FIG. 3 shows a DSC of the commercial vitamin E/PEG 6000 blend.

A DSC of the commercial alpha-tocopherol/PEG 6000 blend is shown in FIG. 3.

Figure 4:
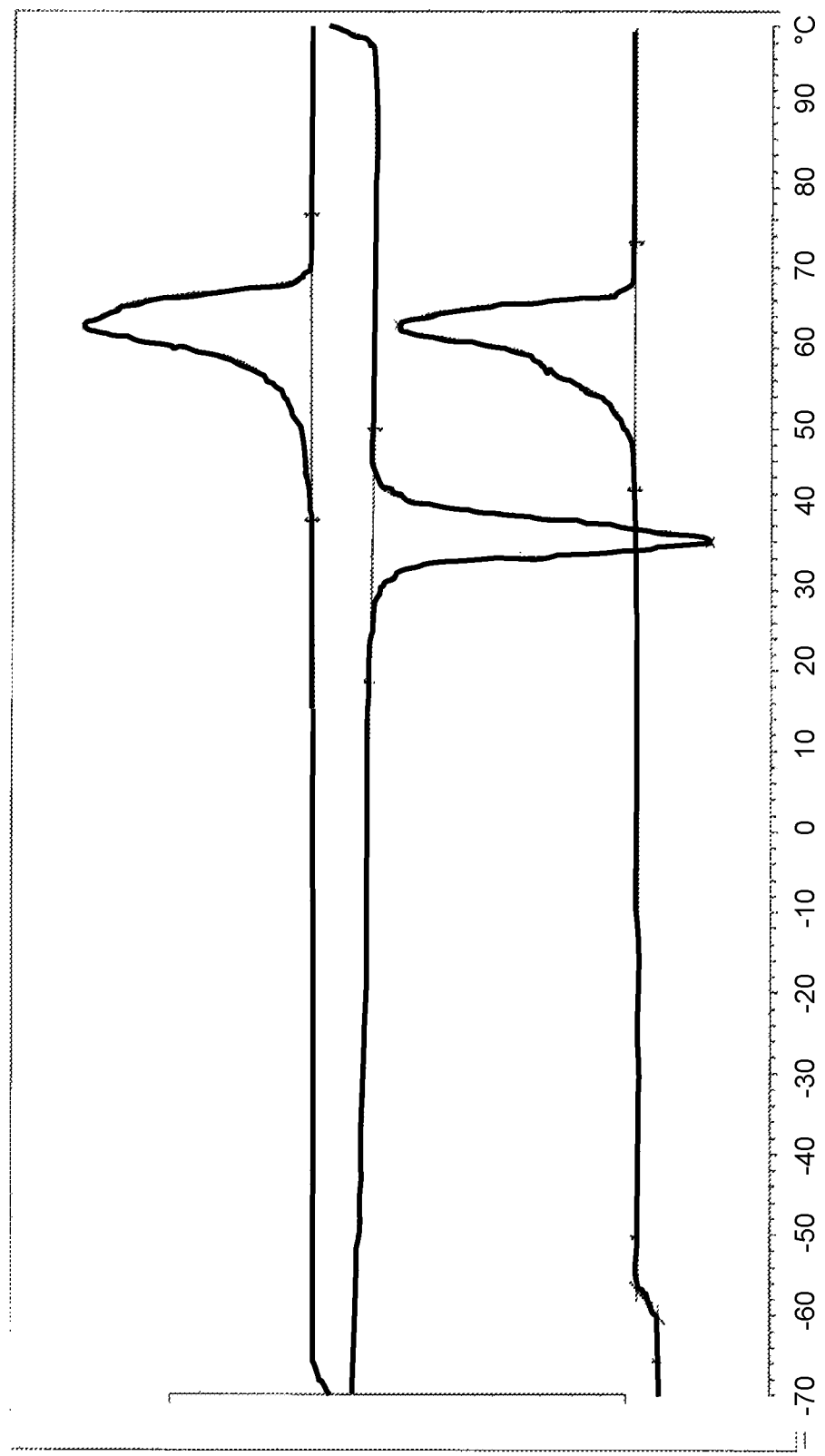
FIG. 4 shows a DSC of Vitamin E/PEG 4% material after cryo-milling.

DSC of alpha-tocopherol/PEG 4% material after cryo-milling is shown in FIG. 4.

Figure 5:
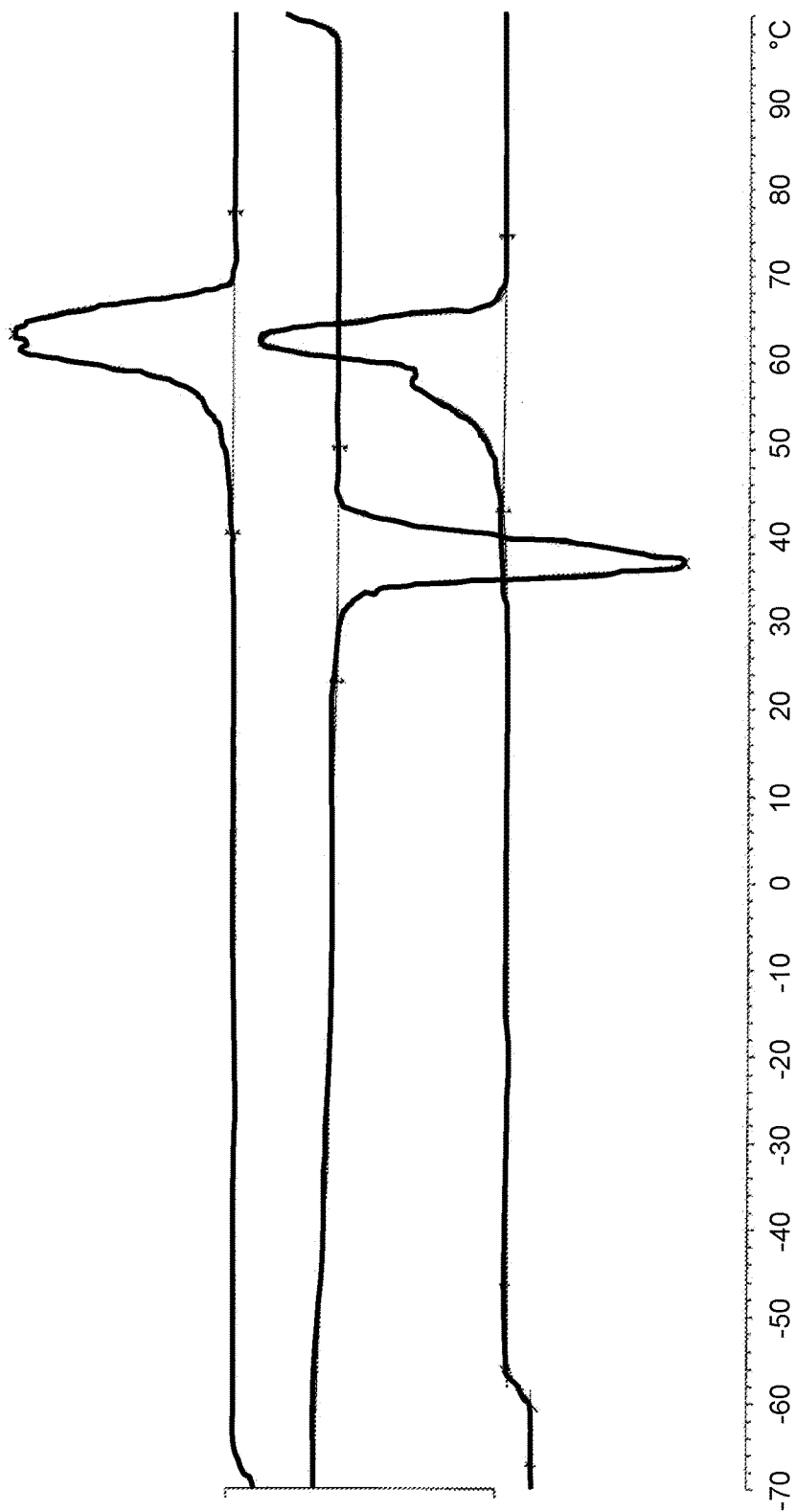
FIG. 5 shows a DSC of Vitamin E/PEG 14% material after cryo-milling.

DSC of alpha-tocopherol/PEG 14% material after cryo-milling is shown in FIG. 5.

EXAMPLE 3—CRYO-MILLING OF PRE-BLEND—NUOVA GUSEO

The pre-blended material of Example 1 was charged in a throttle feeding device. The material was embrittled in contact with liquid nitrogen. The cooled material fell into the grinding system, equipped with a rotating plate beater and a 0.5 and 0.8 mm sieve.

Milling trials were performed varying the follows process parameters: rotation speed (rpm), net size, and temperature. The first trial (trial 1) was performed with a screw feeding device, with severe dosing problems, due the material dimension and the low melting temperature. The parameters used in the other trials are summarized in the table:

| Trial | Rpm | Net size (mm) | Temperature (° C.) |
|---|---|---|---|
| 2 | 5000 | 0.8 | −60 |
| 3 | 6000 | 0.8 | −60 |
| 4 | 7000 | 0.8 | −58 |
| 5 | 5000 | 0.5 | −60 |
| 6 | 6000 | 0.5 | −54 |
| 7 | 7000 | 0.5 | −50 |
| 8 | 7000 | 0.5 | −30 |
| 9 | 7000 | 0.5 | −15 |

After milling, a fine white-yellow powder was obtained. Flowablity test failed for nozzles 6 mm and 10 mm with stirrer on or off, as for the reference (commercial spray-congealed blend). Bulk densities were similar among the trials and compared to the reference (commercial spray-congealed blend). Tapped density was not considered a significant parameter, due the clogging of the material, as well as for the reference (commercial spray-congealed blend):

| alpha-tocopherol/PEG 14% | Density Bulk g/ml |
|---|---|
| Trial 1 | 0.500 |
| Trial 2 | 0.518 |
| Trial 3 | 0.501 |
| Trial 4 | 0.491 |
| Trial 5 | 0.498 |
| Trial 6 | 0.485 |
| Trial 7 | 0.466 |
| Trial 8 | 0.466 |
| Trial 9 | 0.478 |
| alpha-tocopherol/PEG 14% commercial blend | 0.438 |

Figure 6:
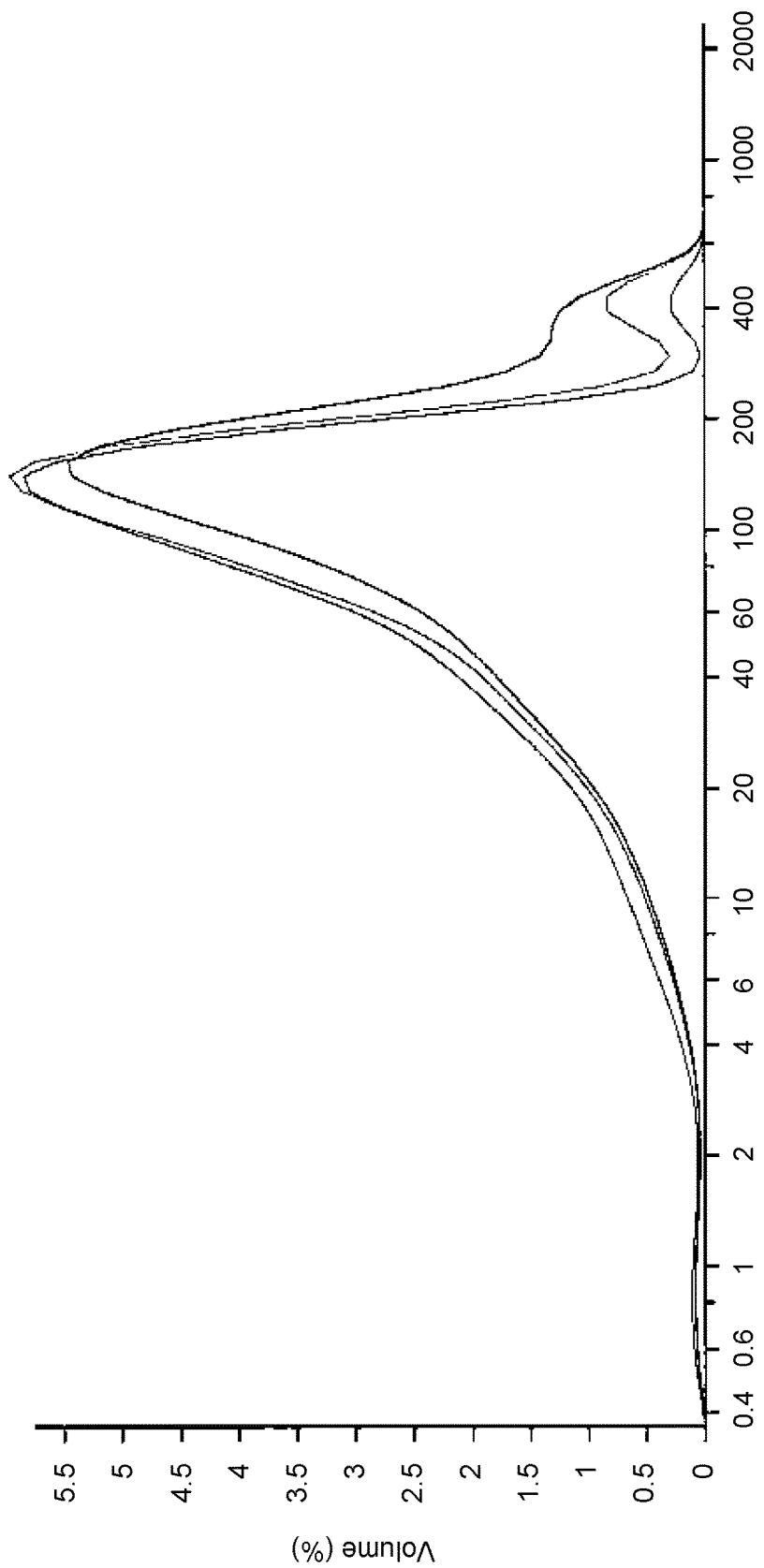
FIG. 6 shows the influence of the temperature on the particle size distribution (PSD).

The influence of the temperature on the particle size distribution (PSD) is shown in FIG. 6.

| | d 10 (μm) | d 50 (μm) | d 90 (μm) |
|---|---|---|---|
| alpha-tocopherol/PEG 14% Trial 7 | 15.2 | 86.1 | 174.4 |
| alpha-tocopherol/PEG 14% Trial 8 | 19.6 | 96.5 | 195.0 |
| alpha-tocopherol/PEG 14% Trial 9 | 21.1 | 109.0 | 251.2 |

Figure 7:
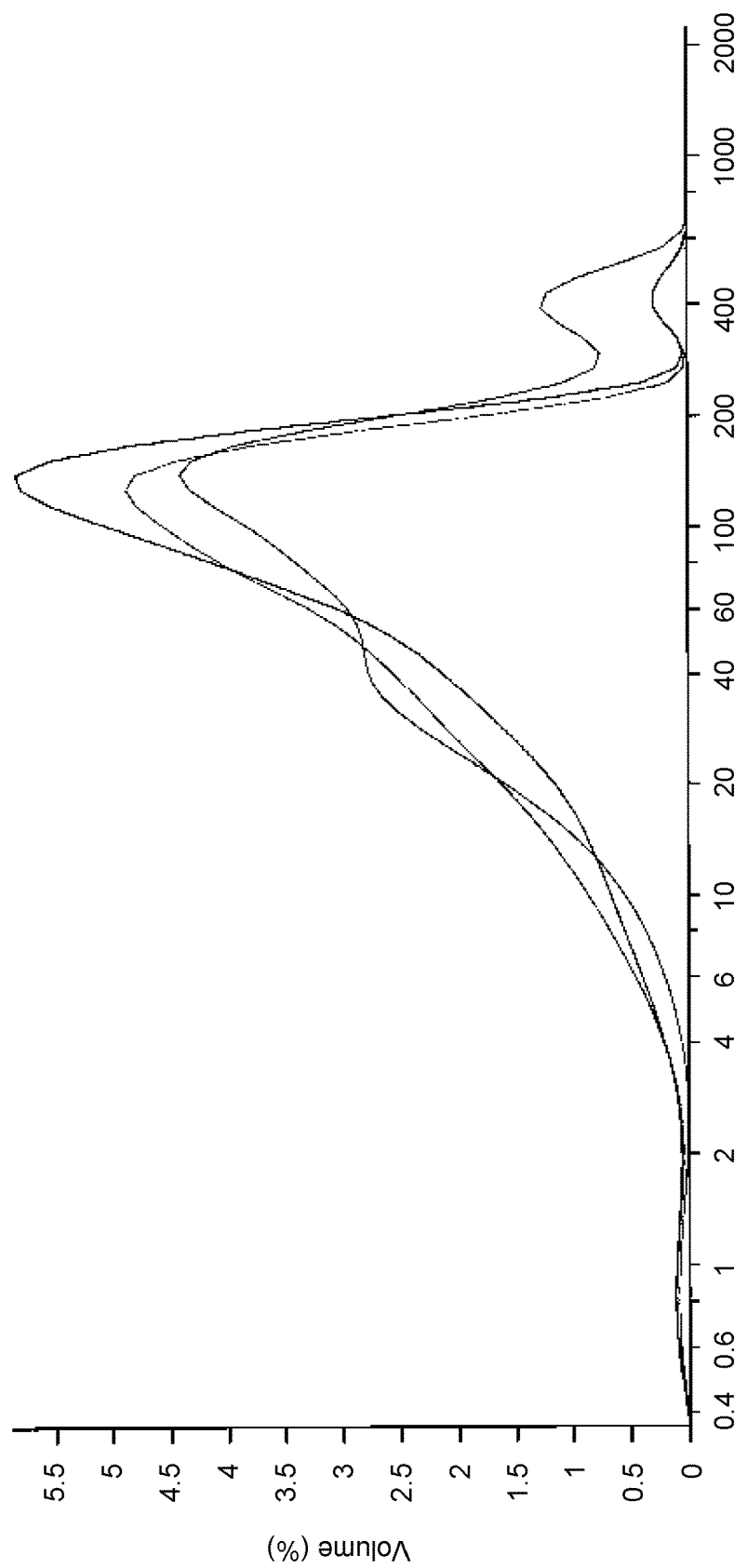
FIG. 7 shows the influence of the cryo-milling technology on the particle size distribution (PSD).

The influence of the cryo-milling technology on the particle size distribution (PSD) is shown in FIG. 7.

|  | d 10 (μm) | d 50 (μm) | d 90 (μm) |
|---|---|---|---|
| alpha-tocopherol/PEG 14% commercial blend | 18.9 | 80.5 | 220.2 |
| alpha-tocopherol/PEG 14% Trial 7 Hosokawa | 19.6 | 96.5 | 195.0 |
| alpha-tocopherol/PEG 14% Trial 7 Nuova Guseo | 15.2 | 86.1 | 174.4 |

Relative Alpha-Tocopherol Content within Blend Before and after Cryo-Milling:

| Mill manufacturer | alpha-tocopherol content | Relative alpha-tocopherol content Before milling | Relative alpha-tocopherol content After milling |
|---|---|---|---|
| Hosokawa | 4% | 93.7% | 93.5-95.5% |
|  | 14% | 111.1% | 111.2-111.3% |
| Nuova Guseo | 14% | 98.5% | 95.3-97.4% |

As can be concluded from the above data, with cryo-milling process the alpha-tocopherol did not degrade.

EXAMPLE 4—ALPHA-TOCOPHEROL/PEG BLENDING TRIALS 4.1 The cryo-milled blends obtained in Examples 2 and 3, respectively, were blended with other ingredients of a drug product formulation. Content uniformity of distribution of alpha-tocopherol within the blend as well as physical characteristics (i.e. flowability, density, particle size distribution (PSD)) were investigated.

Experimental Design 3 blending trials (same qualitative and quantitative composition) with:

Reference 14% alpha-tocopherol/PEG commercial blend

14% alpha-tocopherol/PEG material (cryo-milled by means of Hosokawa, Example 2)

14% alpha-tocopherol/PEG material (cryo-milled by means of Nuova Guseo, Example 3)

The total batch size was 48 kg.

The following blends were prepared:

|  | 25 mg | 50 mg | 100 mg | 100 mg BIS | 150 mg | 200 mg | 250 mg |
|---|---|---|---|---|---|---|---|
| API | 29.12 | 58.24 | 116.48 | 116.48 | 174.72 | 232.96 | 291.20 |
| [mg/tbl] | 7.28% | 14.56% | 29.12% | 29.12% | 38.83% | 35.84% | 41.60% |
| PEG | 225.16 | 225.16 | 187.12 | 179.32 | 166.83 | 260.39 | 245.00 |
| [mg/tbl] | 56.29% | 56.29% | 46.78% | 44.83% | 37.07% | 40.06% | 35.00% |
| HPMC | 85.12 | 56.00 | 56.00 | 56.00 | 63.00 | 91.00 | 98.00 |
| [mg/tbl] | 21.28% | 14.00% | 14.00% | 14.00% | 14.00% | 14.00% | 14.00% |
| PEG 6000 | 56.31 | 56.31 | 37.54 | 45.34 | 42.24 | 61.01 | 60.80 |
| [mg/tbl] | 14.08% | 14.08% | 9.39% | 11.34% | 9.39% | 9.39% | 8.69% |
| alpha-toc/PEG | 4.29 | 4.29 | 2.86 | 2.86 | 3.21 | 4.64 | 5.00 |
| [mg/tbl] | 1.07% | 1.07% | 0.72% | 0.72% | 0.71% | 0.71% | 0.71% |

Figure 8:
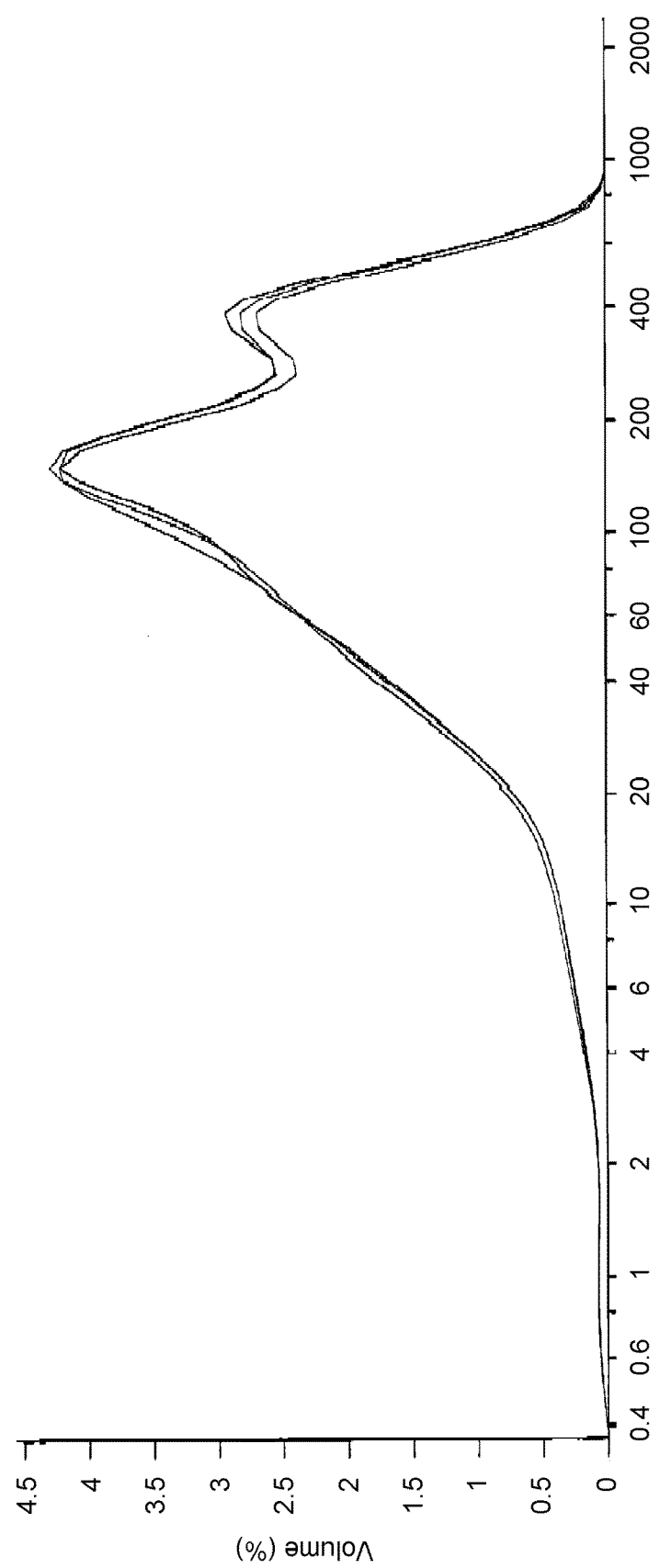
FIG. 8 shows a comparison of particle size distribution (PSD) after blending.

A comparison of particle size distribution (PSD) after blending is shown in FIG. 8.

|  | d 10 (μm) | d 50 (μm) | d 90 (μm) |
|---|---|---|---|
| alpha-tocopherol/PEG 14% commercial blend | 24.73 | 130.10 | 407.10 |
| alpha-tocopherol/PEG 14% Hosokawa material | 22.97 | 122.00 | 391.30 |
| alpha-tocopherol/PEG 14% Nuova Guseo aterial | 25.15 | 129.70 | 404.10 |

Densities and flowabilities are summarized in the table here below:

|  | Density | | | Flowability |
|---|---|---|---|---|
|  | Bulk g/ml | Tapped g/ml (2500 taps) | Carr Index % | Stirrer 1 s/100 g |
| alpha-tocopherol/PEG 14% commercial blend | 0.455 | 0.583 | 21.82 | 153.5 |
| alpha-tocopherol/PEG 14% Hosokawa material | 0.447 | 0.582 | 23.21 | 156.3 |
| alpha-tocopherol/PEG 14% Nuova Guseo material | 0.450 | 0.581 | 22.52 | 161.1 | alpha-tocopherol content uniformities are summarized in the table here below:

|  | tamper resistant formulation containing 100 mg Tapentadol and alpha-tocopherol/PEG 14% commercial blend alpha-Tocopherol | tamper resistant formulation containing 100 mg Tramadol and alpha-tocopherol/PEG 14% commercial blend alpha-Tocopherol (%) | tamper resistant formulation containing 100 mg Tramadol and alpha-tocopherol/PEG 14% inventive blend alpha-Tocopherol (%) |
|---|---|---|---|
| Top 1 | 97.5 | 94.5 | 98.6 |
| Middle 1 | 96.9 | 102.2 | 99.3 |
| Bottom 1 | 95.8 | 95.0 | 98.2 |
| Top 2 | 101.0 | 93.7 | 101.0 |
| Middle 2 | 97.9 | 98.9 | 97.3 |
| Bottom 2 | 95.7 | 96.1 | 99.3 |
| Top 3 | 101.7 | 94.7 | 99.8 |
| Middle 3 | 96.9 | 95.2 | 97.8 |
| Bottom 3 | 95.8 | 96.8 | 99.5 |
| Middle 4 | 96.0 | 94.7 | 96.4 |
| Average | 97.4 | 96.2 | 98.7 |
| RSD % | 2.2 | 2.7 | 1.4 |

Weight uniformities in cut rods are summarized in the table here below:

|  | alpha-tocopherol/PEG 14% commercial blend (mg/cut rods) | | alpha-tocopherol/PEG 14% inventive blend (mg/cut rods) | |
|---|---|---|---|---|
| Time (min) | Average weight | Weight RSD | Average weight | Weight RSD |
| Start | 669.3 | 0.55% | 668.9 | 0.43% |
| 20 | 666.5 | 0.45% | 669.7 | 0.37% |
| 40 | 666.4 | 0.50% | 670.6 | 0.60% |
| 60 | 669.2 | 0.45% | 669.3 | 0.39% |
| 80 | 667.4 | 0.45% | 669.0 | 0.45% |
| 100 | 667.7 | 0.37% | 666.0 | 0.50% |
| 120 | 667.1 | 0.37% | 669.8 | 0.30% |
| 140 | 667.0 | 0.40% | 668.0 | 0.49% |

Extrusion speed for both batches: 16.8 kg/h alpha-tocopherol content uniformities in cut rods are summarized in the table here below:

| Time (min) | Estimated cut-rods manufactured (#) | alpha-tocopherol/ PEG 14% commercial blend (%) | alpha-tocopherol/ PEG 14% inventive blend (%) |
|---|---|---|---|
| Start | 0 | 90.4 | 92.7 |
| 8 | 3350 | 90.4 | 93.7 |
| 16 | 6700 | 90.7 | 93.7 |
| 32 | 13400 | 91.2 | 93.1 |
| 48 | 20100 | 90.6 | 93.4 |
| 64 | 26800 | 89.4 | 92.2 |
| 80 | 33500 | 91.0 | 94.2 |
| 96 | 40200 | 90.7 | 93.0 |
| 112 | 46900 | 90.6 | 93.1 |
| 128 | 53600 | 90.9 | 93.4 |
| Average |  | 90.6 | 93.3 |
| St. Dev. |  | 0.48865 | 0.56421 |
| CV % |  | 0.5 | 0.6 |

Extrusion speed for both batches: 16.8 kg/h

The above experimental data demonstrate that the properties of the blends according to the invention are at least as good as the properties of a commercially available product that has been manufactured by a procedure which is significantly more laborious and expensive than the method according to the invention.

The invention claimed is:

1. A method for preparing a powdery pharmaceutical composition comprising a pharmaceutical excipient and a pharmaceutical component, wherein the pharmaceutical excipient is polyethylene glycol having a molecular weight of up to 50,000 g/mol; the method comprising the steps of:
    (a)(i) mixing the pharmaceutical excipient with the pharmaceutical component outside an extruder and then feeding the pharmaceutical excipient and the pharmaceutical component as mixed into the extruder;
    or
    (ii) feeding the pharmaceutical excipient and the pharmaceutical component into the extruder at different feeding points, where either (1) the feeding point for the pharmaceutical excipient is located upstream with respect to the feeding point for the pharmaceutical component, or (2) the feeding point for the pharmaceutical component is located upstream with respect to the feeding point for the pharmaceutical excipient;
    (b) extruding a mixture of the pharmaceutical excipient and the pharmaceutical component in the extruder at a temperature profile allowing a liquid melt of the mixture to congeal in the extruder and to exit the extruder in form of a powder extrudate; and
    (c) grinding the powder extrudate at a temperature below ambient temperature, wherein the temperature below ambient temperature is at most −10° C.

2. The method according to claim 1, wherein step (c) is performed using a cryo-mill, which is equipped with a cooling system and a milling chamber capable of providing mechanical impact on the material to be milled.

3. The method according to claim 2, wherein the cryo-mill is equipped with a sieve that allows material of the desired particle size to exit the milling chamber but keeps the coarser material within the milling chamber.

4. The method according to claim 2, wherein the cryo-mill is selected from the group consisting of ball mills, colloid mills, conical mills, disintegrators, disk mills, edge mills, gristmills, hammer mills, jet mills, pellet mills, planetary mills, plate mills, stirred mills, and vibratory mills.

5. The method according to claim 1, wherein in step (a) the pharmaceutical component is dissolved in the molten pharmaceutical excipient, or the pharmaceutical excipient is dissolved in the molten pharmaceutical component.

6. The method according to claim 1, which further comprises after step (d):
(d) grading the powder.

7. The method according to claim 1, wherein in step (b) the temperature profile comprises a temperature gradient of temperature $T_1$ to temperature $T_2$, where $T_1 > T_2$ and where
  $T_1$ is above the melting point/range of the pharmaceutical excipient and/or the pharmaceutical component; and/or
  $T_2$ is below the melting point/range of the pharmaceutical excipient and/or the pharmaceutical component.

8. The method according to claim 1, wherein the powdery pharmaceutical composition has an average particle size of at most 100 µm.

9. The method according to claim 1, wherein the pharmaceutical excipient is hydrophilic and the pharmaceutical component is hydrophobic, or the pharmaceutical component is hydrophilic and the pharmaceutical excipient is hydrophobic.

10. The method according to claim 1, wherein the pharmaceutical component is a second pharmaceutical excipient.

11. The method according to claim 10, wherein
  the second pharmaceutical excipient is alpha-tocopherol.

12. The method according to claim 11, wherein the relative weight ratio of the polyethylene glycol to the alpha-tocopherol is within the range of from 1000:1 to 5:1.

* * * * *